(12) United States Patent
Arora et al.

(10) Patent No.: US 7,202,332 B2
(45) Date of Patent: Apr. 10, 2007

(54) METHODS FOR PREPARING INTERNALLY CONSTRAINED PEPTIDES AND PEPTIDOMIMETICS

(75) Inventors: Paramjit Arora, New York, NY (US); Ross Chapman, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 11/128,722

(22) Filed: May 13, 2005

(65) Prior Publication Data

US 2006/0014675 A1 Jan. 19, 2006

Related U.S. Application Data

(60) Provisional application No. 60/574,964, filed on May 27, 2004.

(51) Int. Cl.
*A61K 38/00* (2006.01)
(52) U.S. Cl. ........................ 530/333; 530/317
(58) Field of Classification Search ...................... None
See application file for complete search history.

(56) References Cited

U.S. PATENT DOCUMENTS

| 5,446,128 A | 8/1995 | Kahn |
| 5,710,245 A | 1/1998 | Kahn |
| 5,859,184 A | 1/1999 | Kahn et al. |

OTHER PUBLICATIONS

Andrews & Tabor, "Forming Stable Helical Peptides Using Natural and Artifical Amino Acids," *Tetrahedron* 55:11711-11743 (1999).
Angel & Karin, "The Role of Jun, Fos and the AP-1 Complex in Cell-proliferation and Transformation," *Biochim. Biophys. Acta* 1072:129-157 (1991).
Austin et al., "A Template for Stabilization of a Peptide α-Helix: Synthesis and Evaluation of Conformational Effects by Circular Dichroism and NMR," *J. Am. Chem. Soc.* 119:6461-6472 (1997).
Banerji et al., "Synthesis of Cyclic β-Turn Mimics from L-Pro-Phe/Phe-L-Pro Derived Di- and Tripeptides via Ring Closing Metathesis: The Role of Chirality of the Phe Residue During Cyclization," *Tetrahedron Lett.*. 43:6473-6477 (2002).
Bierzynski et al., "A Salt Bridge Stabilizes the Helix Formed by Isolated C-Peptide of RNase A," *Proc. Nat'l Acad. Sci. USA* 79:2470-2474 (1982).
Blackwell & Grubbs, "Highly Efficient Synthesis of Covalently Cross-linked Peptide Helices by Ring-closing Metathesis," *Angew. Chem. Int. Ed.* 37(23):3281-3284 (1998).
Bracken et al., "Synthesis and Nuclear Magnetic Resonance Structure Determination of an α-Helical, Bicyclic, Lactam-bridged Hexapeptide," *J. Am. Chem. Soc.* 116:6431-6432 (1994).
Burfield & Smithers, "Desiccant Efficiency in Solvent Drying. 3. Dipolar Aprotic Solvents," *J. Org. Chem.* 43(20):3966-3968 (1978).
Cabezas & Satterthwait, "The Hydrogen Bond Mimic Approach: Solid-phase Synthesis of a Peptide Stabilized as an α-Helix with a Hydrazone Link," *J. Am. Chem. Soc.* 121:3862-3875 (1999).

Chakrabartty et al., "Helix Capping Propensitien in Peptides Parallel Those in Proteins," *Proc. Nat'l Acad. Sci. USA* 90:11332-11336 (1993).
Chakrabartty et al., "Helix Propensities of the Amino Acids Measured in Alanine-based Peptides without Helix-stabilizing Sidechain Interactions, " *Protein Sci.* 3:843-852 (1994).
Chapman et al., "A Highly Stable Short α-Helix Constrained by a Main-chain Hydrogen-bond Surrogate," *J. Am. Chem. Soc.* 126:12252-12253 (2004).
Chen et al., "Determination of the Secondary Structures of Proteins by Circular Dichroism and Optical Rotatory Dispersion," *Biochemistry* 11(22): 4120-4131 (1972).
Chen et al., "Structure of the DNA-binding Domains from NFAT, Fos and Jun Bound Specifically to DNA," *Nature* 392:42-48 (1998).
Chène, P., "Inhibiting the p53-MDM2 Interaction: An Important Target For Cancer Therapy," *Nat. Rev. Cancer* 3:102-109 (2003).
Chène et al., "Study of the Cytotoxic Effect of a Peptidic Inhibitor of the p53-hdm2 Interaction in Tumor Cells," *FEBS Lett.* 529:293-297 (2002).
Chin & Schepartz, "Design and Evolution of a Miniature Bcl-2 Binding Protein," *Angew. Chem. Int. Ed.* 40(20):3806-3809 (2001).
Chin et al., "Circular Dichroism Spectra of Short, Fixed-nucleus Alanine Helices," *Proc. Nat'l Acad. Sci. USA* 99(24):15416-15421 (2002).
Cory et al., "The Bcl-2 Family: Roles in Cell Survival and Oncogenesis," *Oncogene* 22:8590-8607 (2003).
Daugherty & Gellman, "A Fluorescence Assay for Leucine Zipper Dimerization: Avoiding Unintended Consequences of Fluorophore Attachment," *J. Am. Chem. Soc.* 121:4325-4333 (1999).
Degterev et al., "Identification of Small-molecule Inhibitors of Interaction between the BH3 Domain and Bcl-$x_L$," *Nature Cell Biol.* 3:173-182 (2001).
Eckert & Kim, "Mechanism of Viral Membrane Fusion and Its Inhibition," *Annu. Rev. Biochem.* 70:777-810 (2001).
Felix et al., "Synthesis, Biological Activity and Conformational Analysis of Cyclic GRF Analogs," *Int. J. Pept. Protein Res.* 32:441-454 (1988).
García-Echeverría et al., "Discovery of Potent Antagonists of the Interaction between Human Double Minute 2 and Tumor Suppressor p53," *J. Med. Chem.* 43:3205-3208 (2000).
Geistlinger & Guy, "An Inhibitor of the Interaction of Thyroid Hormone Receptor β and Glucocorticoid Interaction Protein I," *J. Am. Chem. Soc.* 123:1525-1526 (2001).
Gemperli et al., "Paralog-selective Ligands for Bcl-2 Proteins," *J. Am. Chem. Soc.* 127:1596-1597 (2005).
Ghadiri & Choi, "Secondary Structure Nucleation in Peptides. Transition Metal Ion Stabilzed α-Helices," *J. Am. Chem Soc.* 112:1630-1632 (1990).
Glover & Harrison, "Crystal Structure of the Heterodimeric bZIP Transcription Factor c-Fos-c-Jun Bound to DNA," *Nature* 373:257-261 (1995).

(Continued)

*Primary Examiner*—Cecilia J. Tsang
*Assistant Examiner*—Thomas S. Heard
(74) *Attorney, Agent, or Firm*—Nixon Peabody LLP

(57) ABSTRACT

The present invention relates to a method for preparing a peptide having a stable, internally constrained alpha-helical, beta-sheet/beta-turn, $3_{10}$-helical, or pi-helical region and a method of stabilizing an alpha-helical, beta-sheet/beta-turn, $3_{10}$-helical, or pi-helical region within a peptide structure. The resulting peptides and methods of using them are also disclosed.

8 Claims, 16 Drawing Sheets

OTHER PUBLICATIONS

Hoveyda et al., "Ru Complexes Bearing Bidentate Carbenes: From Innocent Curiosity to Uniquely Effective Catalysts for Olefin Metathesis," *Org. Biomolec. Chem.* 2:8-23 (2004).

Jackson et al., "General Approach to the Synthesis of Short α-Helical Peptides," *J. Am. Chem. Soc.* 113:9391-9392 (1991).

Kaul & Balaram, "Stereochemical Control of Peptide Folding," *Bioorg. Med. Chem.* 7:105-117 (1999).

Kelso et al., "A Cyclic Metallopeptide Induces αHelicity in Short Peptide Fragments of Thermolysin," *Angew. Chem. Int. Ed.* 42(4):421-424 (2003).

Kelso et al., "α-Turn Mimetics: Short Peptide α-Helices Composed of Cyclic Metallopentapeptide Modules," *J. Am. Chem. Soc.* 126:4828-4842 (2004).

Kemp et al., "Studies of N-Terminal Templates for α-Helix Formation. Synthesis and Conformational Analysis of Peptide Conjugates of (2S,5S,8S,11S)-1-Acetyl-1,4-diaza-3-keto-5-carboxy-10-thiatricyclo[2.8.1.0$^{4,8}$]-tridecane (Ac-Hel$_1$-OH)," *J. Org. Chem.* 56:6683-6697 (1991).

Kemp et al., "Studies of N-Terminal Templates for α-Helix Formation. Synthesis and Conformational Analysis of (2S,5S,8S,11S)-1-Acetyl-1,4-diaza-3-keto-5-carboxy-10-thiatricyclo[2.8.1.0$^{4,8}$]-tridecane (Ac-Hel$_1$-OH),"*J. Org. Chem.* 56:6672-6682 (1991).

Kilby et al., "Potent Suppression of HIV-1 Replication in Humans by T-20, a Peptide Inhibitor of gp4-Mediated Virus Entry," *Nat. Med.* 4(11):1302-1307 (1998).

Kritzer et al., "Helical β-Peptide Inhibitors of the p53-hDM2 Interaction," *J. Am. Chem. Soc.* 126:9468-9469 (2004).

Kussie et al, "Structure of the MDM2 Oncoprotein Bound to the p53 Tumor Suppressor Transactivation Domain," *Science* 274:948-953 (1996).

Kutzki et al., "Development of a Potent Bcl-x$_L$ Antagonist Based on α-Helix Mimicry," *J. Am. Chem. Soc.* 124:11838-11839 (2002).

Letai et al., "Distinct BH3 Domain Either Sensitize or Activate Mitochondrial Apoptosis, Serving as Prototype Cancer Therapeutics," *Cancer Cell* 2:183-192 (2002).

Lifson & Roig, "On the Theory of Helix-coil Transition in Polypeptides," *J. Chem. Phys.* 34(6):1963-1974 (1961).

Litowski & Hodges, "Designing Heterodimeric Two-stranded α-Helical Coiled-coils: Effects of Hydrophobicity and α-Helical Propensity on Protein Folding, Stability, and Specifity," *J. Biol. Chem.* 277(40):37272-37279 (2002).

Lyu & Wemmer, "Capping Interactions in Isolated α Helices: Position-dependent Substitution Effects and Structure of a Serine-capped Peptide Helix," *Biochemistry* 32:421-425 (1993).

Lyu et al., "α-Helix Stabilization by Natural and Unnatural Amino Acids with Alkyl Side Chains," *Proc. Nat'l Acad. Sci. USA* 88:5317-5320 (1991).

Marqusee & Baldwin, "Helix Stabilization by Glu$^-$ · · · Lys$^+$ Salt Bridges in Short Peptides of *De Novo* Design," *Proc. Nat'l Acad. Sci. USA* 84:8898-8902 (1987).

McNamara et al., "Peptides Constrained by an Aliphatic Linkage between Two C$^α$ Sites: Design, Synthesis and Unexpected Conformational Properties of an *i* ,(*i* +4)-Linked Peptide," *J. Org. Chem.* 66:4585-4594 (2001).

Miller & Scanlan, "oNBS-SPPS: A New Method for Solid-phase Peptide Synthesis," *J. Am. Chem. Soc.* 120:2690-2691 (1998).

Nelson & Kallenbach, "Persistance of the α-Helix Stop Signal in the S-Peptide in Trifluoroethanol Solutions," *Biochemistry* 28:5256-5261 (1989).

O'Neil & DeGrado, "A Thermodynamic Scale for the Helix-forming Tendencies of the Commonly Occuring Amino Acids," *Science* 250:646-651 (1990).

O'Shea et al., "Mechanism of Specificity in the Fos-Jun Oncoprotein Heterodimer," *Cell* 68:699-708 (1992).

Ōsapay & Taylor, "Multicyclic Polypeptide Model Compounds. 2. Synthesis and Conformational Properties of a Highly α-Helical Uncosapeptide Constrained by Three Side-chain to Side-chain Lactam Bridges," *J. Am. Chem. Soc.* 114:6966-6973 (1992).

Pangborn et al., "Safe and Convenient Procedures for Solvent Purification," *Organometallics* 15:1518-1520 (1996).

Petros et al., "Rationale for Bcl-x$_L$/Bad Peptide Complex Formation from Structure, Mutagenesis, and Biophysical Studies," *Protein Sci.* 9:2528-2534 (2000).

Phelan et al., "A General Method for Constraining Short Peptides to an α-Helical Conformation," *J. Am. Chem. Soc.* 119(3):455-460 (1997).

Qian & Schellman, "Helix-coil Theories: A Comparative Study for Finite Length Polypeptides," *J. Phys. Chem.* 96:3987-3994 (1992).

Roehrl et al., "General Framework for Development and Data Analysis of Competitive High-throughput Screens for Small-molecule Inhibitors of Protein-Protein Interactions by Fluorescence Polarization," *Biochemistry* 43:16056-16066 (2004).

Roehrl et al., "Discovery of Small-molecule Inhibitors of the NFAT-Calcineurin Interaction by Competive High-throughput Fluorescence Polarization Screening," *Biochemistry* 43:16067-16075 (2004).

Ruan et al., "Metal Ion Enhanced Helicity in Synthetic Peptides Containing Unnatural, Metal-ligating Residues," *J. Am. Chem. Soc.* 112:9403-9404 (1990).

Rutledge et al., "A View to a Kill: Ligands for Bcl-2 Family Proteins," *Curr. Opin. Chem. Biol.* 6:479-485 (2002).

Sattler et al., "Structure of Bcl-x$_L$-Bak Peptide Complex: Recognition between Regulators of Apoptosis," *Science* 275:983-986 (1997).

Schafmeister et al., "An All-hydrocarbon Cross-linking System for Enhancing the Helicity and Metabolic Stability of Peptides," *J. Am. Chem. Soc.* 122:5891-5892 (2000).

Shepard et al., "Single Turn Peptide Alpha Helices with Exceptional Stability in Water," *J. Am. Chem. Soc.* 127:2974-2983 (2005).

Sia et al., "Short Constrained Peptides the Inhibit HIV-1 Entry," *Proc. Nat'l Acad. Sci. USA* 99(23):14664-14669 (2002).

Still et al., "Rapid Chromatographic Technique for Preparative Separations with Moderate Resolution," *J. Org. Chem.* 43(14):2923-2925 (1978).

Trnka & Grubbs, "The Development of L$_2$X$_2$Ru=CHR Olefin Metathesis Catalysts: An Organometallic Success Story," *Acc. Chem. Res.* 34:18-29 (2001).

Turner et al., "Mitsunobu Glycosylation of Nitrobenzenesulfonamides: Novel Route to Amadori Rearrangement Products," *Tetrahedron Lett.* 40:7039-7042 (1999).

Tyndall et al., "Proteases Universally Recognize Beta Strands in Their Active Sites," *Chem. Rev.* 105:973-999 (2005).

Vassilev et al., "*In Vivo* Activation of the p53 Pathway by Small-molecule Antagonisits of MDM2," *Science* 303:844-848 (2004).

Walensky et al., "Activation of Apoptosis *in Vivo* by a Hydrocarbon-stapled BH3 Helix," *Science* 305:1466-1470 (2004).

Wild et al., "Peptides Corresponding to a Predictive α-Helical Domain of Human Immunodeficiency Virus Type 1 gp41 are Potent Inhibitors of Virus Infection," *Proc. Nat'l Acad. Sci. USA* 91:9770-9774 (1994).

Yang et al., "Synthesis and Helical Structure of Lactam Bridged BH3 Peptides Derived from Pro-apoptotic Bcl-2 Family Proteins," *Bioorg. Med. Chem. Lett.* 14:1403-1406 (2004).

Yin et al., "Terphenyl-based Helical Mimetics That Disrupt the p53/HDM2 Interaction," *Angew. Chem. Int. Ed.* 44:2704-2707 (2005).

Zhang et al., "Development of a High-throughput Fluorescence Polarization Assay for Bcl-x$_L$," *Anal. Biochem.* 307:70-75 (2002).

Zimm & Bragg, "Theory of the Phase Transition between Helix and Random Coil in Polypeptide Chains," *J. Chem. Phys.* 31(2):526-535 (1959).

Arora, "A General Method for the Stabilization of Peptide Secondary Structures," *Bioorganic Gordon Conference* (2003) (poster).

Arora, "Design, Synthesis, and Properties of the Hydrogen Bond Surrogate-based Artificial Alpha-helices," *American Chemical Society Meeting, San Diego* (Mar. 2005). (oral).

Arora, "Hydrogen Bond Surrogate Approach for the Synthesis of Short α-Helical Peptides," *American Chemical Society Meeting, Philadelphia* (Aug. 2004) (abstract of oral presentation).

Chapman et al., "A Hydrogen Bond Surrogate Approach for the Synthesis of Short Alpha-helical Peptides," *Bioorganic Gordon Conference* (2004) (poster).

Chapman et al., "A Hydrogen Bond Surrogate Approach for the Synthesis of Short Alpha-helical Peptides," *Sixteenth International Symposium on Chirality, New York* (Jul. 2004) (poster).

Chapman et al., "Design, Synthesis, and Properties of the Hydrogen Bond Surrogate-based Artificial Alpha-helices," *Bioorganic Gordon Conference* (2005) (poster).

Dimartino et al., "A General Approach for the Stabilization of Peptide Secondary Structures," *American Chemical Society Meeting, New York* (Sep. 2003) (abstract).

Dimartino et al., "A General Approach for the Stabilization of Peptide Secondary Structures," *American Society Meeting, New York* (Sep. 2003) (poster).

Wang et al., "Recognition of a Protein Receptor with the Hydrogen Bond Surrogate-based Artificial Alpha-helices," *American Chemical Society Meeting, San Diego* (Mar. 2005) (poster).

Wang et al., "Recognition of a Protein Receptor with the Hydrogen Bond Surrogate-based Artificial Alpha-helices," *Chemical Biology Symposium, Hunter College* (Jan. 2005) (poster).

Figures 1A-C

Figure 12. Hydrogen-Bonding Patterns Define Peptide Secondary Structures

Figures 15A-C

SEQUENCE LISTING

<160> NUMBER OF SEQ ID NOS: 34

<210> SEQ ID NO 1
<211> LENGTH: 16
<212> TYPE: PRT
<213> ORGANISM: Artificial Sequence -continued

```
<220> FEATURE:
<223> OTHER INFORMATION: Description of Artificial Sequence: Synthetic
      oligomer

<400> SEQUENCE: 1

Gly Gln Val Gly Arg Gln Leu Ala Ile Ile Gly Asp Asp Ile Asn Arg
 1               5                  10                  15

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 2

Gly Gln Val Gly Arg Gln Leu Ala Ile Ile
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 3

Gly Arg Gln Leu Ala Ile Ile Gly Asp Asp Ile Asn Arg
 1               5                  10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 4

Lys Glu Thr Ala Ala Ala Lys Phe Glu Arg Glu His Met Asp Ser
 1               5                  10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 5

Met Lys Gln Leu Glu Asp Lys
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 6

Val Glu Glu Leu Leu Ser Lys
 1               5
```

```
<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 7

Gln Tyr His Leu Glu Gln Glu
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 8

Val Ala Arg Leu Lys Lys Leu
  1               5

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 9

Met Lys Gln Leu Glu Asp Lys Val Glu Glu Leu Leu Ser Lys
  1               5                  10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 10

Val Glu Glu Leu Leu Ser Lys Gln Tyr His Leu Glu Gln Glu
  1               5                  10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 11

Gln Tyr His Leu Glu Gln Glu Val Ala Arg Leu Lys Lys Leu
  1               5                  10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      oligomer
```

```
<220> FEATURE:
<221> NAME/KEY: PEPTIDE
<222> LOCATION: (4)
<223> OTHER INFORMATION: X at position 4 is N, H, A,  E

<400> SEQUENCE: 12

Glu Pro Gly Xaa Leu Val Arg
 1               5

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence:  Synthetic
      oligomer

<400> SEQUENCE: 13

Thr Arg Gln Ala Arg Arg Asn Arg Arg Arg Arg Trp Arg Glu Arg Gln
 1               5                  10                  15

Arg

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence:  Synthetic
      oligomer

<400> SEQUENCE: 14

Ser Gln Glu Thr Phe Ser Asp Leu Trp Lys Leu Leu Pro Glu Asn Asn
 1               5                  10                  15

Val

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence:  Synthetic
      oligomer

<400> SEQUENCE: 15

Gln Gln Leu Glu Glu Asp Leu Lys Gly Tyr Leu Asp Trp Ile Thr Gln
 1               5                  10                  15

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence:  Synthetic
      oligomer

<400> SEQUENCE: 16

Arg Ile Ala Arg Leu Glu Glu Lys Val Lys
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence:  Synthetic
      oligomer
```

-continued

```
<400> SEQUENCE: 17

Glu Leu Ala Ser Thr Ala Asn Ala Leu Arg Glu
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 18

Gln Val Ala Gln Leu Lys Gln Lys Val Ala
1               5                   10

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 19

Glu Leu Ala Ser Thr Ala Asn Ala Leu Arg Glu Gln Val Ala Gln Leu
1               5                   10                  15

Lys Gln Lys Val Ala Ala Tyr
            20

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 20

Arg Ile Ala Arg Leu Glu Glu Lys Val Lys Thr Leu Lys Ala Gln Asn
1               5                   10                  15

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 21

Glu Val Ala Gln Leu Glu Asp Glu Lys Ser Ala Leu Gln
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 22

Trp Ala Ala Trp Asp Arg Glu Ile Asn Asn Tyr Thr
1               5                   10
```

```
<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence:  Synthetic
      oligomer

<400> SEQUENCE: 23

Trp Ala Ala Trp Asp Arg Glu Ile Asn
 1               5

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence:  Synthetic
      oligomer

<400> SEQUENCE: 24

Pro Arg Gly Thr Arg Gly Lys Gly Arg Arg Ile Arg Arg
 1               5                  10

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence:  Synthetic
      oligomer
<220> FEATURE:
<221> NAME/KEY: PEPTIDE
<222> LOCATION: (9)
<223> OTHER INFORMATION: X at position 9 is any amino acid
<220> FEATURE:
<221> NAME/KEY: PEPTIDE
<222> LOCATION: (10)
<223> OTHER INFORMATION: X at position 10 is any amino acid
<220> FEATURE:
<221> NAME/KEY: PEPTIDE
<222> LOCATION: (11)
<223> OTHER INFORMATION: X at position 11 is any amino acid
<220> FEATURE:
<221> NAME/KEY: PEPTIDE
<222> LOCATION: (12)
<223> OTHER INFORMATION: X at position 12 is any amino acid

<400> SEQUENCE: 25

Val Lys Lys Ile Thr Val Ser Ile Xaa Xaa Xaa Xaa Ile Ser Val Thr
 1               5                  10                  15

Ile Lys Lys Val
            20

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence:  Synthetic
      oligomer
<220> FEATURE:
<221> NAME/KEY: PEPTIDE
<222> LOCATION: (8)
<223> OTHER INFORMATION: X at position 8 is any amino acid
<220> FEATURE:
<221> NAME/KEY: PEPTIDE
<222> LOCATION: (9)
<223> OTHER INFORMATION: X at position 9 is any amino acid
```

```
<400> SEQUENCE: 26

Pro Gln Phe Asn Leu Arg Thr Xaa Xaa Thr Arg Leu Asn Phe Gln Pro
 1               5                  10                  15

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 27

Arg Gln Leu Ala Ile Ile Gly Asp Asp Ile Asn Arg
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      oligomer
<220> FEATURE:
<221> NAME/KEY: PEPTIDE
<222> LOCATION: (9)
<223> OTHER INFORMATION: Lysine at position 9 is acetylated

<400> SEQUENCE: 28

Arg Gln Leu Ala Ile Ile Gly Asp Lys Ile Asn Arg
 1               5                  10

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 29

Ser Asp Leu Trp Lys Leu Leu Pro
 1               5

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      oligomer

<400> SEQUENCE: 30

Ala Arg Leu Glu Glu Lys Val Lys Thr Leu Lys Ala Gln Asn Ser
 1               5                  10                  15

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      oligomer
```

```
<400> SEQUENCE: 31

Ser Thr Ala Asn Ala Leu Arg Glu Gln Val Ala Gln Leu Lys Gln Lys
 1               5                  10                  15
Val

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence:  Synthetic
      oligomer

<400> SEQUENCE: 32

Trp Met Glu Trp Asp Arg Glu Ile Asn Asn Tyr Thr
 1               5                  10

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence:  Synthetic
      oligomer

<400> SEQUENCE: 33

Asn Trp Phe Asn Ile
 1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:  Synthetic
      oligomer

<400> SEQUENCE: 34

Gly Glu Ala Ala Ala Ala Glu Ala
 1               5
```

METHODS FOR PREPARING INTERNALLY CONSTRAINED PEPTIDES AND PEPTIDOMIMETICS

This application claims the benefit of U.S. Provisional Patent Application Ser. No. 60/574,964, filed May 27, 2004, which is hereby incorporated by reference in its entirety.

The present invention was made, at least in part, with funding received from the National Institutes of Health, grant number GM073943. The U.S. government may have certain rights in this invention.

FIELD OF THE INVENTION

This invention is directed generally to methods for preparing internally constrained peptides and peptidomimetics.

BACKGROUND OF THE INVENTION

Protein secondary structures include β-sheets/β-turns, π-helices, $3_{10}$-helices, and α-helices.

The α-helix is the most common element of protein secondary structure and participates widely in fundamental biological processes, including highly specific protein-protein and protein-nucleic acids interactions. Molecules that can predictably and specifically disrupt these interactions would be invaluable as tools in molecular biology, and, potentially, as leads in drug development (Kelso et al., *J. Am. Chem. Soc.* 126:4828–4842 (2004); Schafmeister et al., *J. Am. Chem. Soc.*, 122:5891–5892 (2000); Austin et al., *J. Am. Chem. Soc.* 119:6461–6472 (1997); Phelan et al., *J. Am. Chem. Soc.* 119:455–460 (1997); Osapay et al., *J. Am. Chem. Soc.* 114:6966–6973 (1992); Kemp et al., *J. Org. Chem.* 56:6672–6682(1991); Jackson et al., *J. Am. Chem. Soc.* 113:9391–9392 (1991); Ghadiri et al., *J. Am. Chem. Soc.* 112:1630–1632 (1990); Felix et al., *Int. J. Pept. Protein Res.* 32:441–454 (1988)). Exposed α-helices on the surfaces of proteins are also often involved in recognition of other biomolecules. Peptides composed of less than fifteen residues corresponding to these α-helical regions typically do not remain helical once excised from the protein environment. Short peptides (<15 residues) that can adopt α-helical structure are expected to be useful models for the design of bioactive molecules and for studying aspects of protein folding.

Several strategies have been reported for the preparation of stabilized α-helices (Andrews et al., "Forming Stable Helical Peptides Using Natural and Artificial Amino Acids," *Tetrahedron* 55:11711–11743 (1999)). These methods include incorporation of nonnatural amino acids (Lyu et al., "Alpha-helix Stabilization by Natural and Unnatural Amino Acids with Alkyl Side Chains," *Proc. Nat'l Acad. Sci.* 88:5317–5320 (1991); Kaul et al., "Stereochemical Control of Peptide Folding," *Bioorg. Med. Chem.* 7:105–117 (1999)), capping motifs (Austin et al., "Template for Stabilization of a Peptide Alpha-helix: Synthesis and Evaluation of Conformational Effects by Circular Dichroism and NMR," *J. Am. Chem. Soc.* 119:6461–6472 (1997); Lyu et al., "Capping Interactions in Isolated Alpha Helices: Position-dependent Substitution Effects and Structure of a Serine-capped Peptide Helix," *Biochemistry* 32:421–425 (1993); Chakrabartty et al., "Helix Capping Propensities in Peptides Parallel Those in Proteins," *Proc. Nat'l Acad. Sci. U.S.A.* 90:11332–11336 (1993); Kemp et al., "Studies of N-Terminal Templates for Alpha-helix Formation—Synthesis and Conformational-analysis of (2s,5s,8s,11s)-1-acetyl-1,4-diaza-3-keto-5-carboxy-10-thiatricyclo[2.8.1.0(4,8)]tridecane (Ac-Hel1-Oh)," *J. Org. Chem.* 56:6683–6697 (1991)), salt-bridges (Bierzynski et al., "A Salt Bridge Stabilizes the Helix Formed by Isolated C-Peptide of RNase A," *Proc. Nat'l Acad. Sci. U.S.A.* 79:2470–2474 (1982)), metal ion chelation (Kelso et al., *J. Am. Chem. Soc.*, 126:4828–4842 (2004); Kelso et al., "A Cyclic Metallopeptide Induces Alpha Helicity in Short Peptide Fragments of Thermolysin," *Angew. Chem. Int. Ed. Engl.* 42:421–424 (2003); Ruan et al., "Metal-ion Enhanced Helicity in Synthetic Peptides Containing Unnatural, Metal-ligating Residues," *J. Am. Chem. Soc.* 112:9403–9404 (1990); Ghadiri, *J. Am. Chem. Soc.,* 112:1630–1632 (1990)), and covalent side chain linkers such as disulfide (Jackson et al., "A General Approach to the Synthesis of Short Alpha-helical Peptides," *J. Am. Chem. Soc.* 113:9391–9392 (1991)), lactam (Phelan et al., "A General Method for Constraining Short Peptides to an Alpha-helical Conformation," *J. Am. Chem. Soc.* 119:455–460 (1997); Bracken et al., *J. Am. Chem. Soc.* 116:6431–6432 (1994); Osapay et al., *J. Am. Chem. Soc.,* 114:6966–6973 (1992); Felix et al., *Int. J. Pept. Protein Res.* 32:441–454 (1988)), and hydrocarbon bridges (Schafmeister et al., "An All-hydrocarbon Cross-linking System for Enhancing the Helicity and Metabolic Stability of Peptides," *J. Am. Chem. Soc.* 122:5891–5892 (2000); Blackwell et al., "Highly Efficient Synthesis of Covalently Cross-linked Peptide Helices by Ring-closing Metathesis," *Angew. Chem. Int. Ed. Engl.* 37:3281–3284 (1998)). Stabilization of the α-helix structure with these strategies is typically context dependent (Geistlinger et al., "An Inhibitor of the Interaction of Thyroid Hormone Receptor Beta and Glucocorticoid Interacting Protein," *J. Am. Chem. Soc.* 123:1525–1526 (2001); McNamara et al., "Peptides Constrained by an Aliphatic Linkage between Two C(alpha) Sites: Design, Synthesis, and Unexpected Conformational Properties of an i,(i+4)-Linked Peptide," *Org. Chem.* 66:4585–4594 (2001)). More importantly, however, these strategies typically block solvent-exposed surfaces of the target α-helices, or restrict or replace important side chain functionalities from the putative α-helices.

Thus, there remains a need for identifying a general method for the synthesis of highly stable internally-constrained peptide structures, such as short α-helical peptides, with strict preservation of the helix surfaces. The present invention is directed to overcoming these and other deficiencies in the art.

SUMMARY OF THE INVENTION

One aspect of the present invention relates to a method of preparing a compound of Formula II:

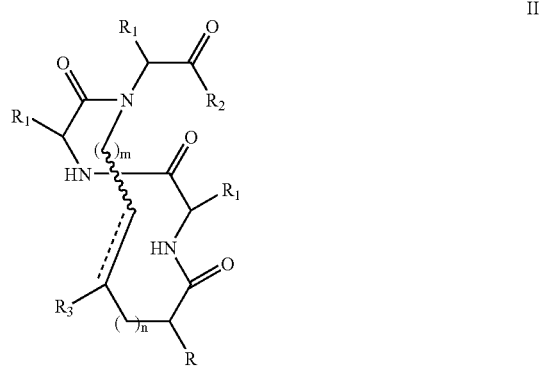

where R is hydrogen, an amino acid side chain, an alkyl group, or an aryl group; $R_1$ is an amino acid side chain, an alkyl group, or an aryl group; $R_2$ is an amino acid, peptide, OR, $CH_2NH_2$, an alkyl group, an aryl group, or a group of formula

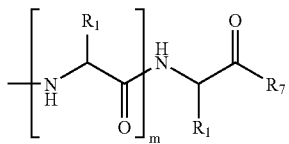

where $R_7$ is an amino acid, peptide, OR, $CH_2NH_2$, an alkyl group, or an aryl group; $R_3$ is an amino acid, peptide, OR, $CH_2NH_2$, an alkyl group, an aryl group, hydrogen, or a group of formula

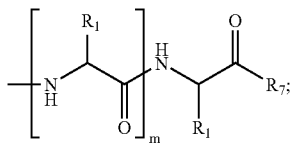

═══ is a single or double carbon-carbon bond; ∼∼∼ is a single bond and is cis or trans when ═══ is a double bond; n is 1 or 2; and m is any number. This method involves providing a compound of Formula I:

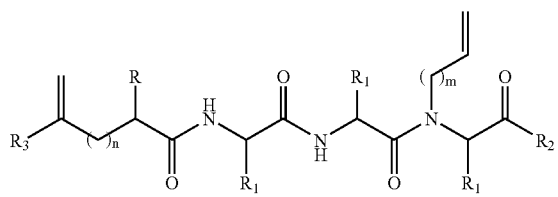

and reacting the compound of Formula I under conditions effective to produce a compound of Formula II.

Another aspect of the present invention relates to a second method of preparing a compound of Formula II. This method involves providing a compound of Formula III or a salt thereof

III

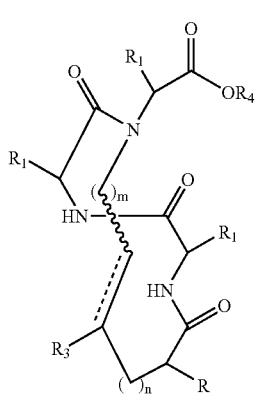

where $R_4$ is a carboxyl protecting group. The compound of Formula III or a salt thereof is reacted with a peptide coupling reagent of Formula III':

III'

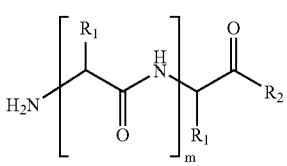

under conditions effective to produce a compound of Formula II.

Another aspect of the present invention relates to peptides having one or more stable, internally-constrained alpha-helical, beta-sheet/beta-turn, $3_{10}$-helical, or pi-helical regions.

Yet another aspect of the present invention relates to a method for promoting cell death. This method involves contacting a cell with one or more Bak BH3 peptides having a stable, internally-constrained alpha-helical region under conditions effective for the one or more Bak BH3 peptides to promote cell death. In this aspect of the present invention, one or more hydrogen bonds within the one or more Bak BH3 peptides are replaced with a carbon-carbon bond.

Yet another aspect of the present invention relates to a method for promoting cell death. This method involves contacting a cell with one or more peptides which inhibits p53/hDM2 interaction and has a stable, internally-constrained alpha-helical region, under conditions effective for the one or more peptides to promote cell death. In this aspect of the present invention, one or more hydrogen bonds within the one or more peptides are replaced with a carbon-carbon bond.

Yet another aspect of the present invention relates to a method for promoting cell death. This method involves contacting the cell with one or more peptides which inhibits Jun-Jun and/or Jun-Fos interactions and has a stable, internally-constrained alpha-helical region under conditions effective for the one or more peptides to promote cell death. In this aspect of the present invention, one or more hydrogen bonds within the one or more peptides are replaced with a carbon-carbon bond.

Yet another aspect of the present invention relates to a method for inhibiting cell proliferation. This method involves contacting the cell with one or more peptides which inhibits Jun-Jun and/or Jun-Fos interactions and has a stable, internally-constrained alpha-helical region under conditions effective for the one or more peptides to inhibit cell proliferation. In this aspect of the present invention, one or more hydrogen bonds within the one or more peptides are replaced with a carbon-carbon bond.

Yet another aspect of the present invention relates to a method for inhibiting cell transformation. This method involves contacting the cell with one or more peptides which inhibits Jun-Jun and/or Jun-Fos interactions and has a stable, internally-constrained alpha-helical region under conditions effective for the one or more peptides to inhibit cell transformation. In this aspect of the present invention, one or more hydrogen bonds within the one or more peptides are replaced with a carbon-carbon bond.

Yet another aspect of the present invention relates to a method for inhibiting HIV-1 entry into a cell. This method involves contacting the cell with one or more peptides having a stable, internally-constrained alpha-helical region under conditions effective for the one or more peptides to inhibit HIV-1 entry into the cell. In this aspect of the present invention, one or more hydrogen bonds within the one or more peptides are replaced with a carbon-carbon bond.

Significantly, and advantageously, the methods of the present invention do not utilize side chain functionality, and the constraining element does not block solvent-exposed surfaces of the molecule. In addition, the resulting conformationally-constrained peptides and peptide structures are more stable with regard to thermal stability and proteolytic degradation than those prepared with prior methods. Moreover, the methods of the present invention utilize irreversible crosslinks that can be generated for amino acid sequences.

Previously, Satterthwait and coworkers have explored the use of a hydrazone link to stabilize α-helices (Cabezas et al., "The Hydrogen Bond Mimic Approach: Solid-phase Synthesis of a Peptide Stabilized as an Alpha-helix with a Hydrazone Link," *J. Am. Chem. Soc.* 121:3862–3875 (1999), which is hereby incorporated by reference in its entirety). The methods of the present invention afford a more stable and irreversible bond as compared to the hydrazone strategy and are applicable to a broader range of peptide sequences. Another advantage of the methods of the present invention is that they more closely mimic the single and double bond patterns of the helix, whereas in the hydrozone approach, a double bond replaces the hydrogen bond and a carbon-carbon single bond replaces the carbonyl.

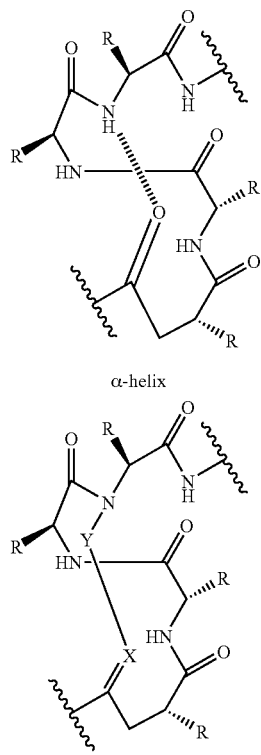

α-helix

X = CH; Y = CH₂
main chain hydrogen
bond surrogate approach

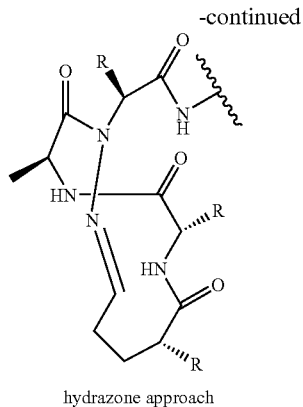

hydrazone approach

BRIEF DESCRIPTION OF THE DRAWINGS

FIG. 1A shows an unconstrained α-helix. FIG. 1B shows an α-helix constrained via the hydrogen bond surrogate approach of the present invention. FIG. 1C shows an α-helix constrained via a side-chain crosslinking strategy.

DETAILED DESCRIPTION OF THE INVENTION

The present invention relates to methods of preparing a compound of Formula II:

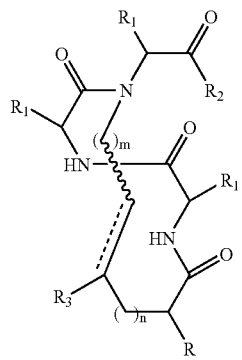

II where R is hydrogen, an amino acid side chain, an alkyl group, or an aryl group; $R_1$ is an amino acid side chain, an alkyl group, or an aryl group; $R_2$ is an amino acid, peptide, OR, $CH_2NH_2$, an alkyl group, an aryl group, or a group of formula

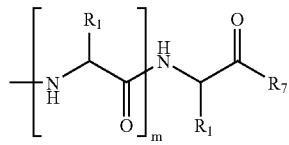

where $R_7$ is an amino acid, peptide, OR, $CH_2NH_2$, an alkyl group, or an aryl group; $R_3$ is an amino acid, peptide, OR, $CH_2NH_2$, an alkyl group, an aryl group, hydrogen, or a group of formula

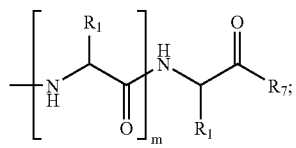

----- is a single or double carbon-carbon bond; ⁓ is a single bond and is cis or trans when ----- is a double bond; n is 1 or 2; and m is any number.

Protein secondary structures are defined by the hydrogen bonding patterns observed between the various main chain amide groups. Analyses of helix-coil transition in peptides emphasize the energetically demanding organization of three consecutive amino acids into the helical orientation as the slow step in helix formation (Qian & Schellman, *J. Chem. Phys.*, 96:3987–3994 (1992); Lifson & Roig, *J. Chem. Phys.*, 34:1963–1974 (1961); Zimm & Bragg, *J. Chem. Phys.*, 31:526–535 (1959), which are hereby incorporated by reference in their entirety). Preorganization of these amino acid residues is expected to overwhelm the intrinsic nucleation propensities and initiate helix formation (Austin et al., *J. Am. Chem. Soc.*, 119:6461–6472 (1997); Kemp et al., *J. Org. Chem.*, 56:6672–6682 (1991), which are hereby incorporated by reference in their entirety). In an α-helix, a hydrogen bond between the C=O of the $i^{th}$ amino acid residue and the NH of the $i+4^{th}$ amino acid residue stabilizes and nucleates the helical structure (see Scheme 1 infra).

To mimic the C=O---H---N hydrogen bond as closely as possible, the main chain hydrogen bond surrogate strategies of this aspect of the present invention incorporate a covalent bond of the type C=X—Y—N, where X and Y correspond to part of the i and the i+4 residues, respectively, as shown in Scheme 1.

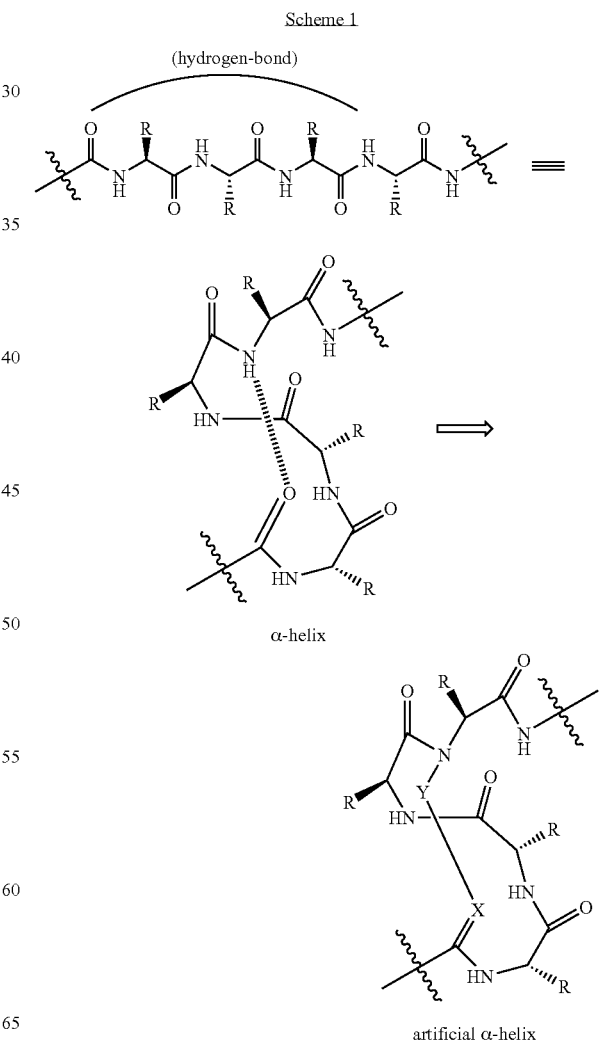

Scheme 1

Figure 1:
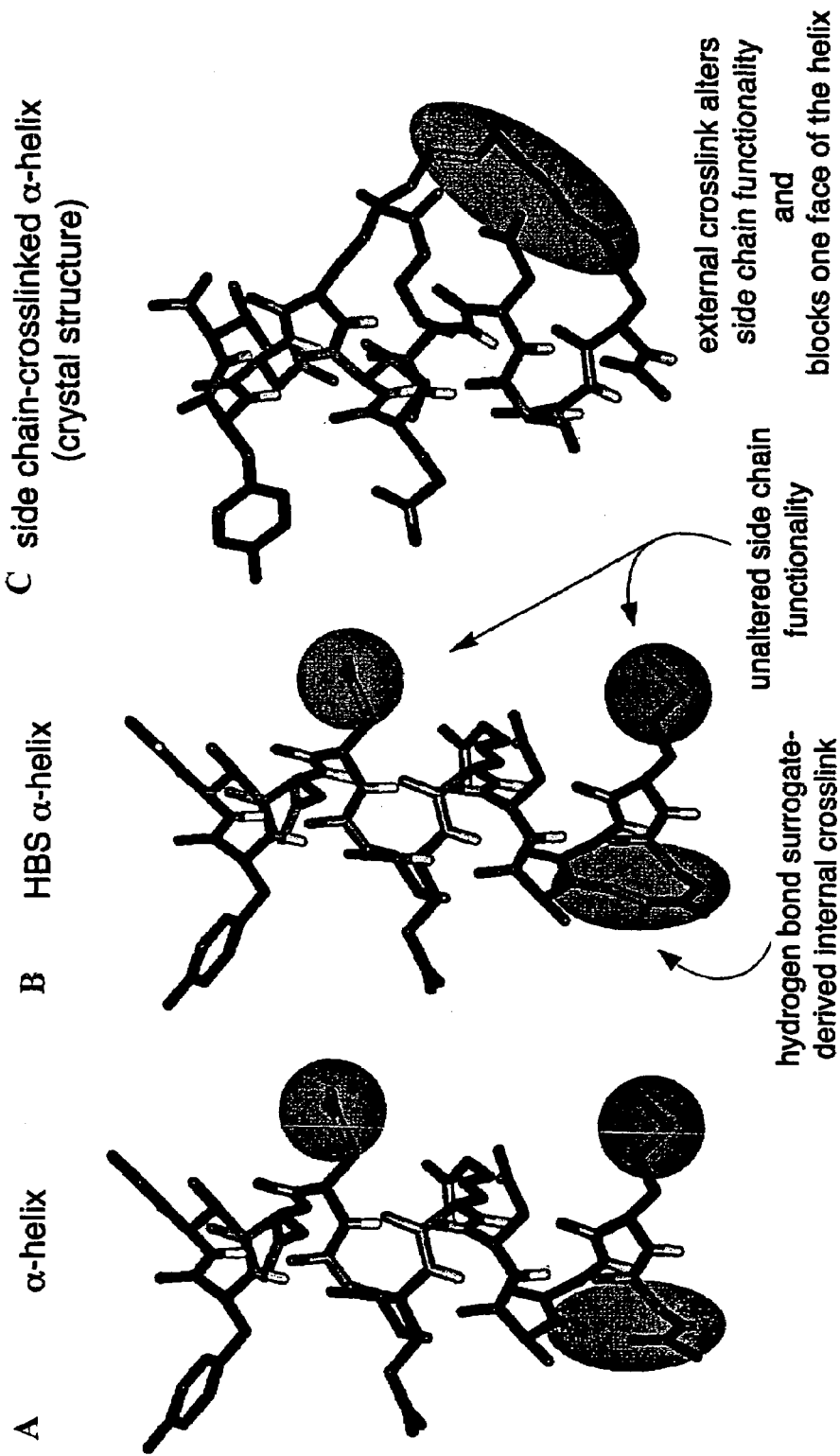
FIGS. 1A–C are schematic diagrams of α-helices.

The internal placement of the crosslink allows the development of α-helices such that none of the exposed surfaces are blocked by the constraining element—i.e., placement of the crosslink on the inside of the helix does not alter side-chain functionality nor block solvent-exposed molecular recognition surfaces of the molecule, as shown in FIG. 1 (see Sia et al., *Proc. Nat'l Acad. Sci. U.S.A.*, 99:14664–14669 (2002), which is hereby incorporated by reference in its entirety). Moreover, even very short peptides (i.e., peptides less than 10 amino acid residues) may be constrained into highly stable α-helices. The hydrogen-bond surrogate approach can also be used to develop sequence-specific ligands for RNA and DNA.

In one aspect of the present invention, preparing a compound of Formula II involves providing a compound of Formula I:

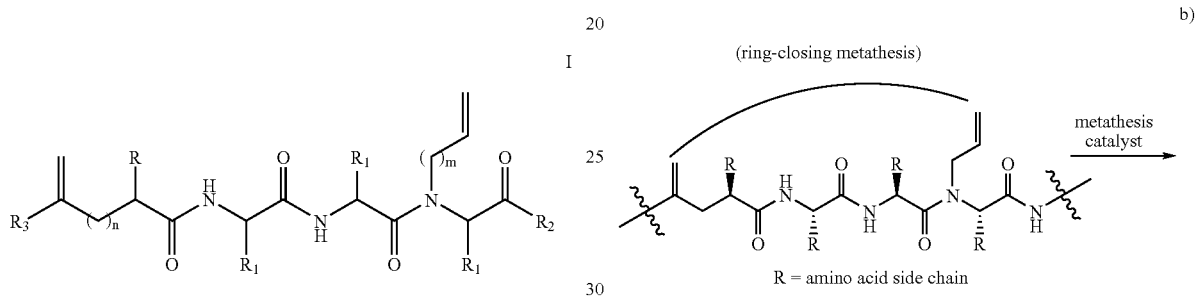

I and reacting the compound of Formula I under conditions effective to produce a compound of Formula II.

To mimic the C=O—H—N hydrogen bond as closely as possible, the present invention incorporates a covalent bond of the type C=X—Y—N, where X and Y correspond to part of the i and the i+4 residues, respectively. The exceptional functional group tolerance displayed by the olefin metathesis catalysts for the facile introduction of non-native carbon-carbon constraints in the preparation of peptidomimetics suggests that X and Y could be two carbon atoms connected through an olefin metathesis reaction, as shown in Scheme 2 (Hoveyda et al., "Ru Complexes Bearing Bidentate Carbenes: From Innocent Curiosity to Uniquely Effective Catalysts for Olefin Metathesis," *Org. Biomolec. Chem.* 2:8–23 (2004); Trnka et al., "The Development of L2X2Tu=CHR Olefin Metathesis Catalysts: An Organometallic Success Story," *Accounts Chem. Res.* 34:18–29 (2001), which are hereby incorporated by reference in their entirety).

Scheme 2 illustrates a strategy for the stabilization of α-helices by replacement of an i and i+4 hydrogen bond (C=O—H—N) (Scheme 2A) with a covalent link (C=X—Y—N), for example a carbon-carbon bond through a ring-closing olefin metathesis reaction (Scheme 2B).

Scheme 2 a)
(hydrogen-bond)

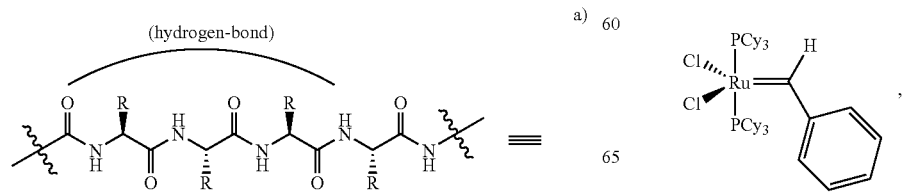

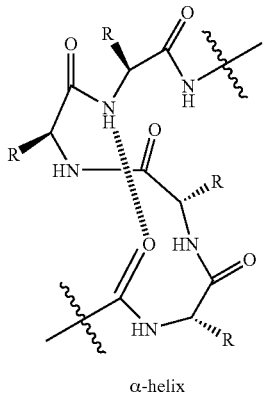

α-helix b)
(ring-closing metathesis)

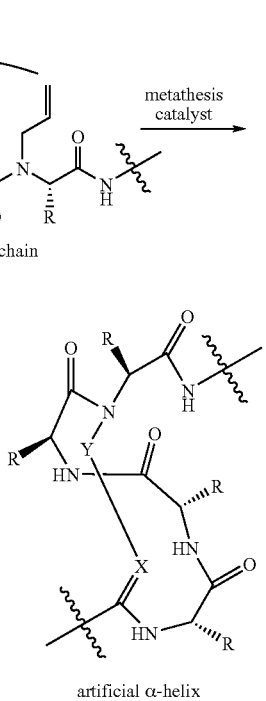

R = amino acid side chain artificial α-helix

This aspect of the present invention may, preferably, involve a ring-closing olefin metathesis reaction. An olefin metathesis reaction couples two double bonds (olefins) to afford two new double bonds (one of which is typically ethylene gas). A ring-closing olefin metathesis utilizes an olefin metathesis reaction to form a macrocycle. In this reaction, two double bonds within a chain are connected. Preferably, the reaction is performed with a metathesis catalyst, for example of the formula

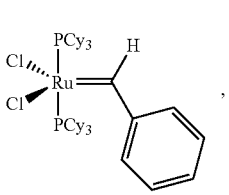

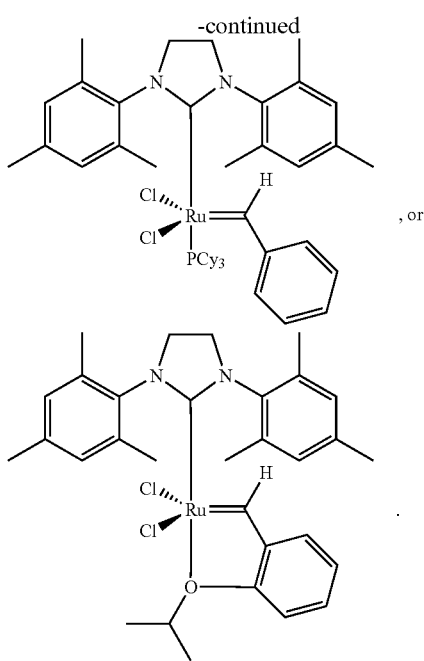

More preferably, the metathesis catalyst is of the formula

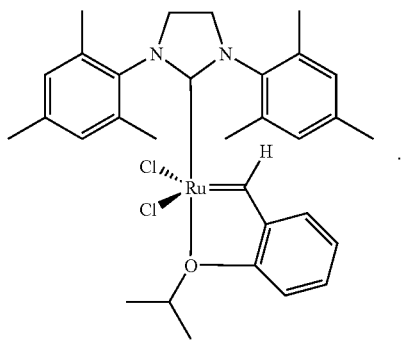

The metathesis reaction may be performed, for example, at a temperature between about 25° C. and 110° C., and more preferably, at a temperature of about 50° C.

The metathesis reaction may be performed with an organic solvent, such as dichloromethane, dichloroethane, trichloroethane, or toluene.

The reactions disclosed herein may, for example, be carried out on a solid support. Suitable solid supports include particles, strands, precipitates, gels, sheets, tubing, spheres, containers, capillaries, pads, slices, films, plates, slides, discs, membranes, etc. These solid supports can be made from a wide variety of materials, including polymers, plastics, ceramics, polysaccharides, silica or silica-based materials, carbon, metals, inorganic glasses, membranes, or composites thereof. The substrate is preferably flat but may take on a variety of alternative surface configurations. For example, the substrate may contain raised or depressed regions on which the synthesis takes place. The substrate and its surface preferably form a rigid support on which to carry out the reactions described herein. Other substrate materials will be readily apparent to those of ordinary skill in the art upon review of this disclosure.

The metathesis reaction performed using a compound of Formula I will initially yield the compound of Formula II in which ⁝⁝⁝⁝ is a double bond. This double bond can be converted to a single bond by hydrogenation methods known in the art, after the peptide secondary structure is constrained.

In another aspect of the present invention, illustrated in Scheme 3, preparing a compound of Formula II involves providing a compound of Formula III or a salt thereof

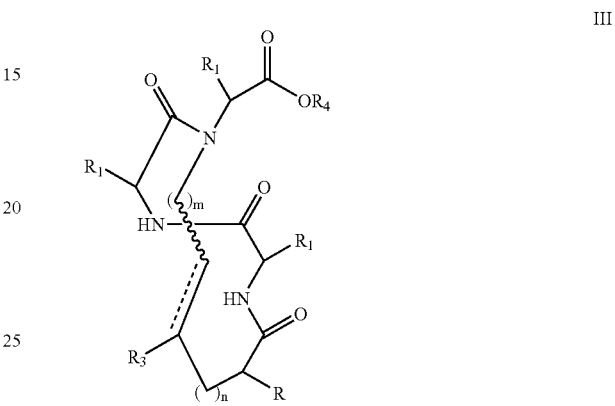

where $R_4$ is a carboxyl protecting group. According to this aspect of the present invention, the compound of Formula III or a salt thereof is reacted with a peptide coupling reagent of Formula III':

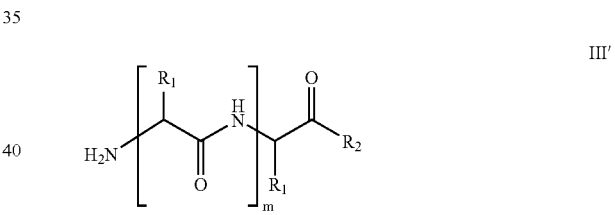

under conditions effective to produce a compound of Formula II.

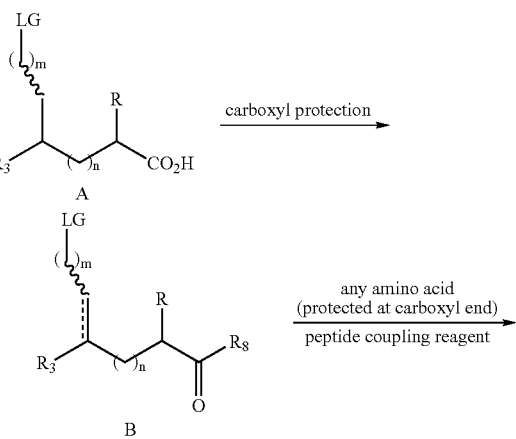

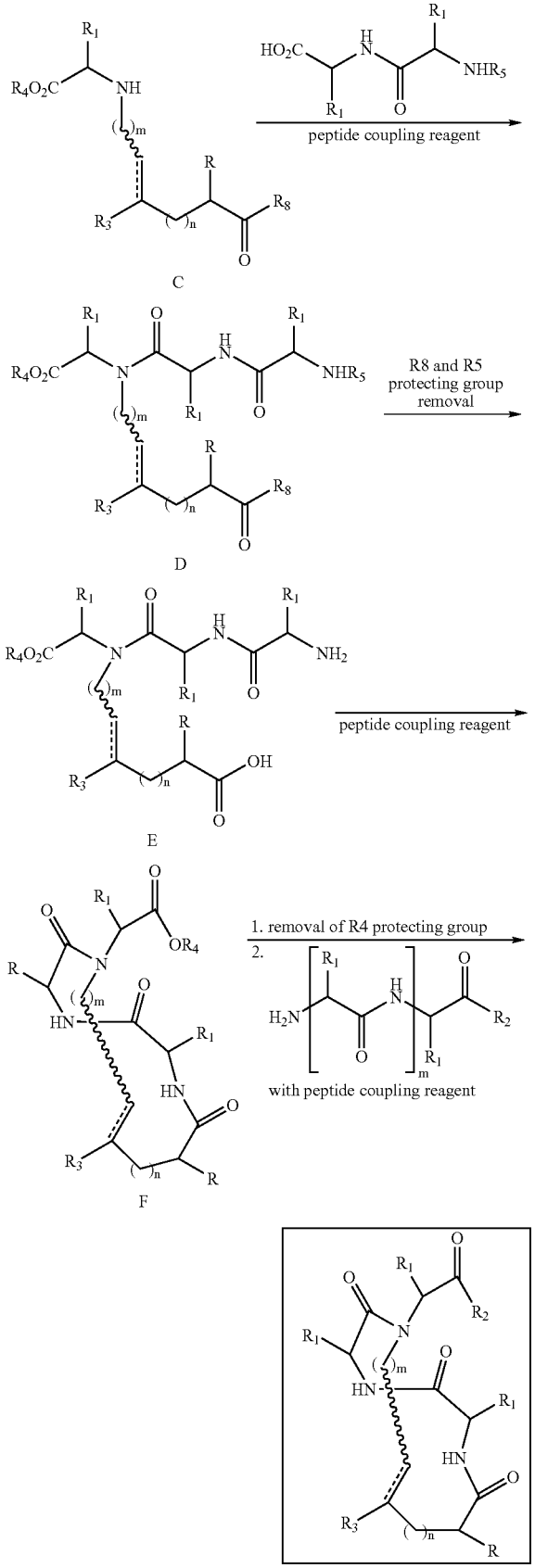

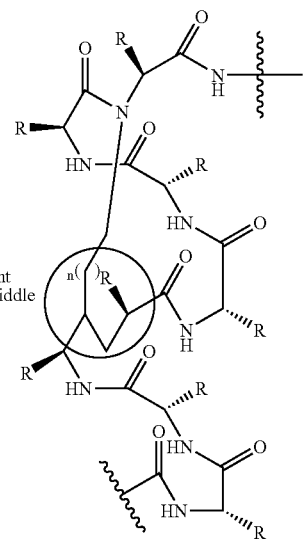

-continued
R = H, amino acid side chain, alkyl, or aryl
$R_1$ = amino acid side chain, alkyl, or aryl
$R_2$ = amino acid, peptide, OR, $CH_2NH_2$, alkyl, aryl, or compound of formula:
$R_3$ = amino acid, peptide, OR, $CH_2NH_2$, alkyl, aryl, or compound of formula:
$R_4$ = carboxyl protecting group that is not $R_8$
$R_5$ = amine protecting group
$R_7$ = amino acid, peptide, OR, $CH_2NH_2$, alkyl, or aryl
$R_8$ = carboxyl protecting group
n = 1 or 2
m = any number The carboxylic acid A is protected as an ester (for example a methyl or ethyl ester), yielding compound B. This compound B is then condensed to commercially available amino acids, generating amine C. Amine C is then coupled to the dipeptide by standard coupling agents such as DCC/HOBT or 5% DIEA/HBTU, yielding compound D. The protecting groups $R_8$ and $R_5$ are removed to afford compound E, which is cyclized with peptide coupling agents to generate peptide F. Removal of the carboxylic acid protecting group $R_4$ exposes the carboxylic acid, which can be coupled to any amino acid to obtain the desired peptide.

As will be apparent to one of ordinary skill in the art, the methods of the present invention may be used to prepare peptides having highly stabilized, internally-constrained α-helices, β-sheets/β-turns, $3_{10}$-helices, and π-helices. The constraint may be placed anywhere within the peptide, not just at the N-terminus. For example, the compound of Formula II prepared according to the methods of the present invention may have the formula The peptides produced according to the methods of the present invention may, for example, be less than 15 amino acids, including, for example, less than 10 amino acid residues.

The present invention also relates to peptides having one or more stable, internally-constrained α-helices, β-sheets/β-turns, $3_{10}$-helices, or π-helices. The one or more stable, internally-constrained secondary structures includes the following motifs:

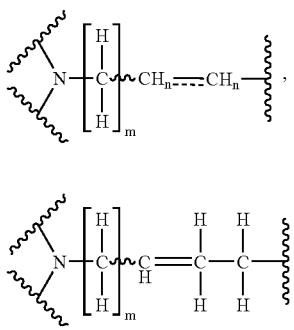

where ----- is a single or double bond, ⁓⁓⁓ is a single bond and is cis or trans when ----- is a double bond; n is 1 or 2; and m is any number. Examples of such motifs include:

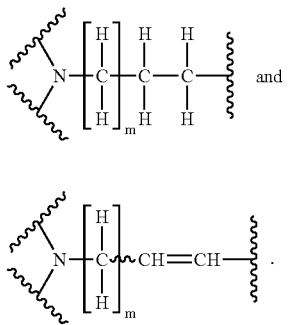

Exemplary peptides according to the present invention include peptides of the following formulae:

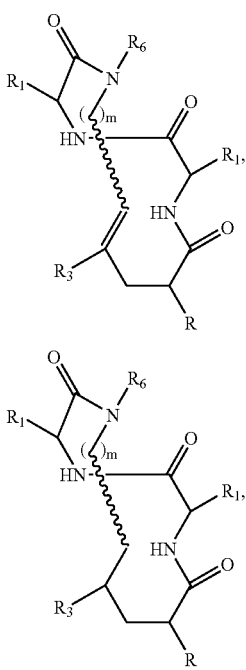

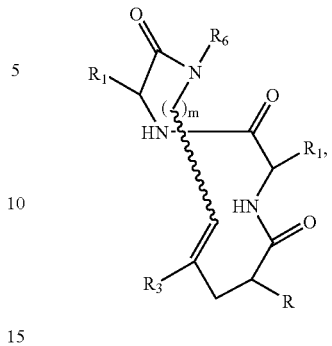

where R is hydrogen, an amino acid side chain, an alkyl group, or an aryl group; $R_1$ is an amino acid side chain, an alkyl group, or an aryl group; $R_3$ is an amino acid, peptide, OR, $CH_2NH_2$, an alkyl group, hydrogen, or an aryl group; and $R_6$ is (a) a chain of one or more amino acids; or (b) a side chain of formula:

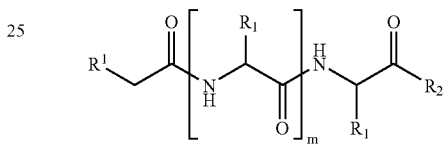

where $R_2$ is an amino acid, peptide, OR, $CH_2NH_2$, an alkyl group, or an aryl group;

----- is a single or double bond, ⁓⁓⁓ is a single bond and is cis or trans when ----- is a double bond; n is 1 or 2; and m is any number. More specific examples of such peptides are shown in Table 1.

TABLE 1

Exemplary Peptides

| entry | peptide | target |
|---|---|---|
| 1 | GQVGRQLAIIGDDINR (SEQ ID NO: 1) | Bcl-xL/Bak BH3 |
| 2 | GQVGRQLAII (SEQ ID NO: 2) | Bcl-xL/Bak BH3 |
| 3 | GRQLAIIGDDINR (SEQ ID NO: 3) | Bcl-xL/Bak BH3 |
| 4 | KETAAAKFEREHMDS (SEQ ID NO: 4) | RNase S protein/C-peptide |
| 5 | MKQLEDK (SEQ ID NO: 5) | GCN4 coiled-coil |
| 6 | VEELLSK (SEQ ID NO: 6) | GCN4 coiled-coil |
| 7 | QYHLEQE (SEQ ID NO: 7) | GCN4 coiled-coil |
| 8 | VARLKKL (SEQ ID NO: 8) | GCN4 coiled-coil |
| 9 | MKQLEDKVEELLSK (SEQ ID NO: 9) | GCN4 coiled-coil |
| 10 | VEELLSKQYHLEQE (SEQ ID NO: 10) | GCN4 coiled-coil |
| 11 | QYHLEQEVARLKKL (SEQ ID NO: 11) | GCN4 coiled-coil |
| 12 | mimics of Zinc finger recognition helix | DNA |
| 13 | EPGXLVR (X = N, H, A, E) (SEQ ID NO: 12) | DNA |
| 14 | TRQARRNRRRRWRERQR (SEQ ID NO: 13) | RRE RNA |
| 15 | SQETFSDLWKLLPENNV (SEQ ID NO: 14) | p53/MDM2 |
| 16 | QQLEEDLKGYLDWITQ (SEQ ID NO: 15) | calcium ion channel (AID) |
| 17 | RIARLEEKVK (SEQ ID NO: 16) | Jun/Fos |
| 18 | hex-RIARLEEKVK (SEQ ID NO: 17) | Jun/Fos |
| 19 | ELASTANALRE (SEQ ID NO: 18) | Jun/Fos |
| 20 | QVAQLKQKVA (SEQ ID NO: 19) | Jun/Fos |
| 21 | ELASTANALREQVAQLKQKVAAY (SEQ ID NO: 20) | Jun/Fos |
| 22 | RIARLEEKVKTLKAQN (SEQ ID NO: 21) | Jun/Fos |
| 23 | EVAQLEDEKSALQ (SEQ ID NO: 22) | Jun/Fos |
| 24 | WAAWDREINNYT (SEQ ID NO: 23) | HIV gp41 |

TABLE 1-continued

Exemplary Peptides

| entry | peptide | target |
|---|---|---|
| 25 | WAAWDREIN (SEQ ID NO: 24) | HIV gp41 |
| 26 | PRGTRGKGRRIRR (SEQ ID NO: 25) | HIV TAR RNA |
| 27 | VKKITVSIXXXXISVTIKKV (X = any amino acid) (SEQ ID NO: 26) | Met represser |
| 28 | PQFNLRTXXTRLNFQP (X = any amino acid) (SEQ ID NO: 27) | Arc repressor |

Although the peptides are disclosed in Table 1 in linear sequence form, they may have one or more stable, internally-constrained secondary structures (i.e., α-helices, β-sheets/β-turns, 3₁₀-helices, or π-helices) at any location within the peptide, as will be apparent to one of skill the art. For example, Entry 1 (SEQ ID NO: 1) may have an artificial a-helix spanning residues 1–5, where G1 and R5 are i and i+4, respectively (see, e.g., Scheme 1 and accompanying text), constrained by methods described herein. Alternatively or additionally, for example, Entry 1 (SEQ ID NO: 1) may have an artificial α-helix spanning residues 12–16, where D12 and R16 are i and i+4, respectively. By way of another example, Entry 27 (SEQ ID NO: 26) may be an artificial internally-constrained beta-sheet with the constraint spanning residues 1–4, where X9 and X12 are i and i+3, respectively.

Yet another aspect of the present invention relates to a method for promoting cell death. This method involves contacting a cell with one or more Bak BH3 peptides having a stable, internally-constrained alpha-helical region under conditions effective for the one or more Bak BH3 peptides to promote cell death. In this aspect of the present invention, one or more hydrogen bonds within the one or more Bak BH3 peptides are replaced with a carbon-carbon bond.

Suitable Bak BH3 peptides include:

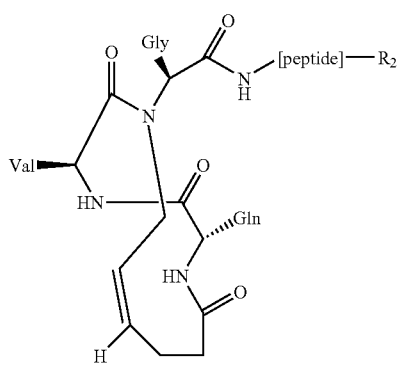

where [peptide] is RQLAIIGDDINR (SEQ ID NO: 27) or RQLAIIGDK^Ac^INR (SEQ ID NO: 28); and R₂ is (a) a peptide, (b) OR where R is an alkyl group, (c) CH₂NH₂, (d) an alkyl group, or (e) an aryl group.

The methods of the present invention relating to contacting a cell with one or more peptides may be carried out in vitro or in vivo.

When contacting is carried out in vivo, contacting may comprise administering to a subject a compound that includes one or more peptides of the present invention. The compounds of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Yet another aspect of the present invention relates to a method for promoting cell death. This method involves contacting a cell with one or more peptides that inhibits p53/hDM2 interaction and has a stable, internally-constrained alpha-helical region, under conditions effective for the one or more peptides to promote cell death. In this aspect of the present invention, one or more hydrogen bonds within the one or more peptides are replaced with a carbon-carbon bond.

Suitable p53/hDM2 peptides include:

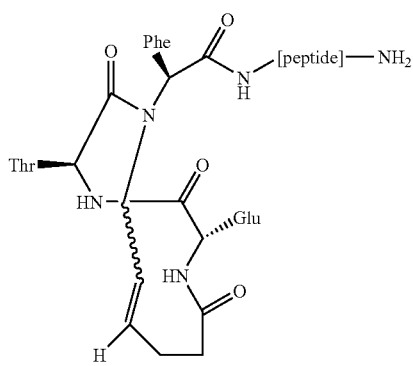

where ᴡᴡᴡ is a cis or trans alkene and [peptide] is SDL-WKLLP (SEQ ID NO: 29).

The p53/hDM2 interaction is known to stop apoptosis and lead to uncontrolled growth (a characteristic of cancer). The internally-constrained artificial p53/hDM2 shown above mimics a portion of p53 protein that binds to hDM2, and is expected to block p53/hDM2 interaction and induce apoptotic activity in cancer cells (Chene, P, "Inhibiting the p53-MDM2 Interaction: An Important Target For Cancer Therapy," *Nat. Rev. Cancer* 3:102–109 (2003); Chene et al., "Study of the Cytotoxic Effect of a Peptidic Inhibitor of the p53-HDN2 Interaction in Tumor Cells," *FEBS Lett.* 529: 293–297 (2002); Garcia-Echeverria et al., "Discovery of Potent Antagonists of the Interaction between Human Double Mminute 2 and Tumor Suppressor p53," *J. Medicinal Chemistry* 43:3205–3208 (2000); Kritzer et al., "Helical (R)-peptide Inhibitors of the p53-hDM2 Interaction," *J. Am. Chem. Soc.* 126:9468–9469 (2004); Kussie et al, "Structure of the MDM2 Oncoprotein Bound to the p53 Tumor Suppressor Transactivation Domain," *Science* 274: 948–953 (1996); Vassilev et al. "In Vivo Activation of the p53 Pathway by Small-molecule Antagonists of MDM2," *Science* 303:844–848 (2004); Yin et aL, "Terphenyl-based Helical Mimetics That Disrupt the p53/HDM2 Interaction," *Angew Chem. Int. Ed.* 44:2704–2707 (2005), which are hereby incorporated by reference in their entirety).

When using this method to treat a subject, the above-mentioned modes and forms of administering are used to contact the cell with the one or more peptides.

Yet another aspect of the present invention relates to a method for promoting cell death. This method involves contacting the cell with one or more peptides which inhibits Jun-Jun and/or Jun-Fos interactions and has a stable, internally-constrained alpha-helical region under conditions effective for the one or more peptides to promote cell death. In this aspect of the present invention, one or more hydrogen bonds within the one or more peptides are replaced with a carbon-carbon bond.

Jun and Fos belong to the basic leucine zipper (bZIP) DNA binding family of proteins, and regulate cell proliferation, apoptosis and transformation (Angel & Karin, "The Role of Jun, Fos and the AP-1 Complex in Cell-proliferation and Transformation," *Biochim. Biophys. Acta* 1072: 129–157 (1991); Chen et al., "Structure of the DNA-binding Domains from NFAT, Fos and Jun Bound Specifically to DNA," *Nature* 392:42–48 (1998); Daugherty & Gellman, "A Fluorescence Assay for Leucine Zipper Dimerization: Avoiding Unintended Consequences of Fluorophore Attachment," *J. Am. Chem. Soc.* 121:4325–4333 (1999); Glover & Harrison et al., "Crystal Structure of the Heterodimeric bZIP Transcription Factor c-Fos-c-Jun Bound to DNA," *Nature* 373:257–261 (1995); O'Shea et al., "Mechanism of Specificity in the Fos-Jun Oncoprotein Heterodimer," *Cell* 68:699–708 (1992), which are hereby incorporated by reference in their entirety). Internally-constrained artificial alpha-helices that target these coiled-coil proteins may be prepared in accordance with the methods of the present invention. Suitable peptides that inhibit Jun-Jun and/or Jun-Fos interactions include:

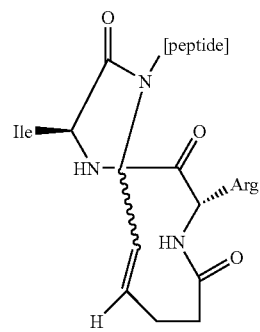

where ᴡᴡᴡ is a cis or trans alkene and [peptide] is ARLEEKVKTLKAQNS (SEQ ID NO: 30) and

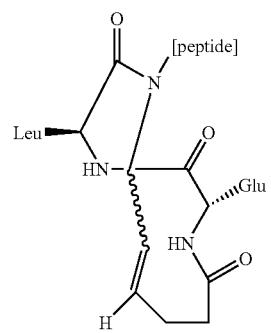

where [peptide] is STANALREQVAQLKQKV (SEQ ID NO: 31).

When using this method to treat a subject, the above-mentioned modes and forms of administering are used to contact the cell with the one or more peptides.

Yet another aspect of the present invention relates to a method for inhibiting cell proliferation. This method involves contacting the cell with one or more peptides which inhibits Jun-Jun and/or Jun-Fos interactions and has a stable, internally-constrained alpha-helical region under conditions effective for the one or more peptides to inhibit cell proliferation. In this aspect of the present invention, one or more hydrogen bonds within the one or more peptides are replaced with a carbon-carbon bond.

Suitable peptides which inhibit Jun-Jun and/or Jun-Fos interactions include those mentioned above.

When using this method to treat a subject, the above-mentioned modes and forms of administering are used to contact the cell with the one or more peptides.

Yet another aspect of the present invention relates to a method for inhibiting cell transformation. This method involves contacting the cell with one or more peptides which inhibits Jun-Jun and/or Jun-Fos interactions and has a stable, internally-constrained alpha-helical region under conditions effective for the one or more peptides to inhibit cell transformation. In this aspect of the present invention, one or more hydrogen bonds within the one or more peptides are replaced with a carbon-carbon bond.

Suitable peptides which inhibit Jun-Jun and/or Jun-Fos interactions include those mentioned above.

When using this method to treat a subject, the above-mentioned modes and forms of administering are used to contact the cell with the one or more peptides.

Yet another aspect of the present invention relates to a method for inhibiting HIV-1 entry into a cell. This method involves contacting the cell with one or more peptides having a stable, internally-constrained alpha-helical region under conditions effective for the one or more peptides to inhibit HIV-1 entry into the cell. In this aspect of the present invention, one or more hydrogen bonds within the one or more peptides are replaced with a carbon-carbon bond.

The role of coiled-coil domains in the fusion of HIV-1 to the host cell membrane has been the subject of intense research activity. Viral fusion is mediated by glycoproteins on the virus surface that contain an α-helical coiled-coil domain. α-Helical peptides that mimic portions (C-terminal heptad repeat of gp41) of this coiled-coil complex can disrupt coiled-coil formation and have been shown to be potent inhibitors of HIV-1 infection in vitro and in vivo. It has been postulated that stabilized α-helices corresponding to this C-terminal heptad repeat sequence (C-peptides) may be more potent inhibitors than the unconstrained peptide, which adopts a random coil conformation in solution. (Eckert et al., "Mechanisms of Viral Membrane Fusion and its Inhibition," *Annu. Rev. Biochem.* 70:777–810 (2001); Kilby et al., "Potent Suppression of HIV-1 Replication in Humans by T-20, a Peptide Inhibitor of gp41-Mediated Virus Entry," *Nat. Med.* 4:1302–1307 (1998); Sia et al., "Short Constrained Peptides that Inhibit HIV-1 Entry," *Proc. Nat'l Acad. Sci. USA* 99:14664–14669 (2002); Wild et al., "Peptides Corresponding to a Predictive Alpha-helical Domain of Human Immunodeficiency Virus Type 1 gp41 are Potent Inhibitors of Virus Infection," *Proc. Nat'l Acad. Sci. USA* 91:9770–9774 (1994), which are hereby incorporated by reference in their entirety.)

Suitable peptides include:

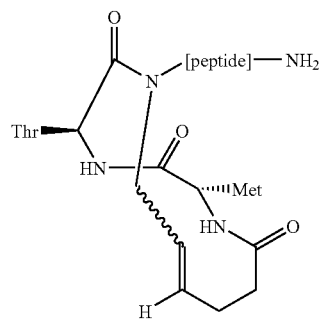

wherein ∿∿∿ is a cis or trans alkene and [peptide] is WMEWDREINNYT (SEQ ID NO: 32), and

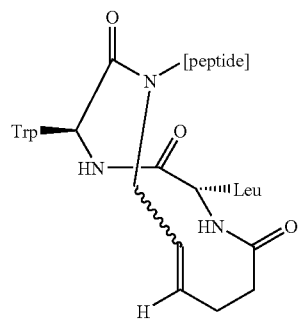

where [peptide] is NWFNI (SEQ ID NO: 33). These peptides are expected to target gp41and block its interactions with CD4.

When using this method to treat a subject, the above-mentioned modes and forms of administering are used to contact the cell with the one or more peptides.

The present invention may be further illustrated by reference to the following examples.

EXAMPLES

Example 1

Synthesis of an Internally-constrained α-Helix

To test the stabilization properties of the metathesis-derived internal crosslinks, an 8-mer constrained peptide 3 bearing a crosslink at the N-terminus was synthesized as shown in Scheme 4. This particular peptide was chosen because the control peptide 1 (AcGEAAAAEA-OMe (SEQ ID NO: 34)) does not display any α-helicity, thus allowing for an observation of an increase in α-helical content following the modification. Two glutamic acid residues were incorporated in this alanine-rich peptide at different faces of the putative helix to increase the solubility of the constrained peptide in aqueous buffers. The metathesis precursor peptide 2 underwent a ring-closing metathesis reaction with Hoveyda-Grubbs metathesis catalyst (Hoveyda et al., "Ru Complexes Bearing Bidentate Carbenes: From Innocent Curiosity to Uniquely Effective Catalysts for Olefin Metathesis," *Org. Biomolec. Chem.* 2: 8–23 (2004), which is hereby incorporated by reference in its entirety) to afford the trans-alkene constrained peptide 3 after the removal of the t-butyl esters.

Scheme 4

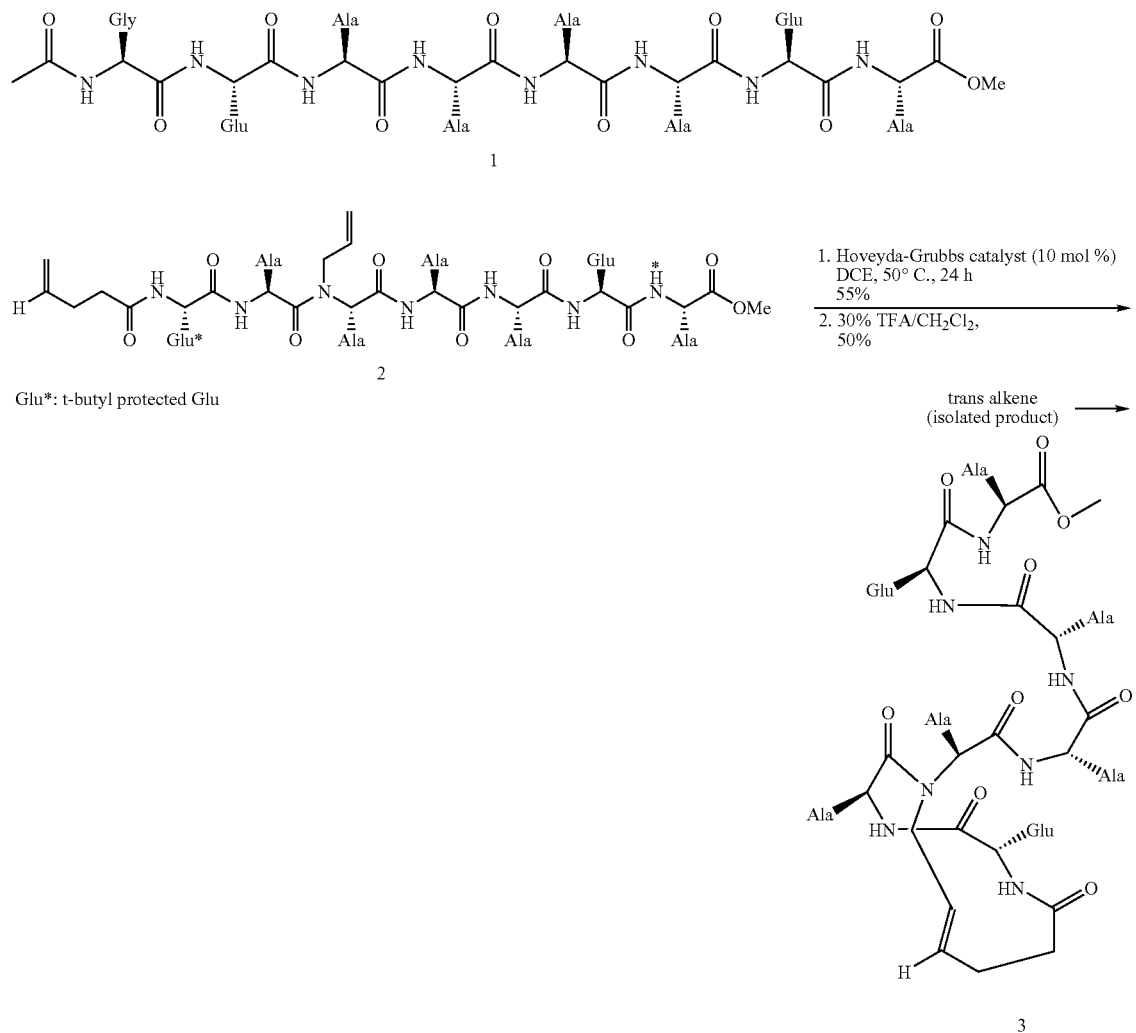

Glu*: t-butyl protected Glu

Peptide Synthesis

As illustrated in Schemes 5 and 6, peptides were synthesized using standard Fmoc solid-phase methodology on Wang resin. The Fukuyama alkylation method has been used extensively to prepare allyl-bearing peptides on resin (Miller et al., "A New Method for Solid-phase Peptide Synthesis," *J. Am. Chem. Soc.* 120:2690–2691 (1998), which is hereby incorporated by reference in its entirety). As shown in Scheme 5, automated solid-phase synthesis was carried out with Fmoc-dipeptide 8, because prior preparation of the alkylated amino acid reduces the synthetic procedure to high yielding reactions optimized for solid phase peptide synthesis. Dimer 8 was synthesized from t-butyl alanine in five steps with the Fukayama alkylation as the key step.

Scheme 5

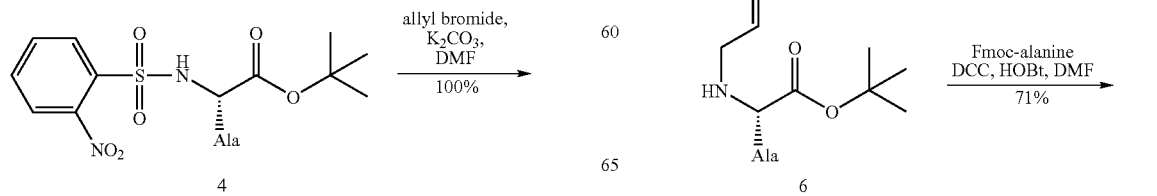

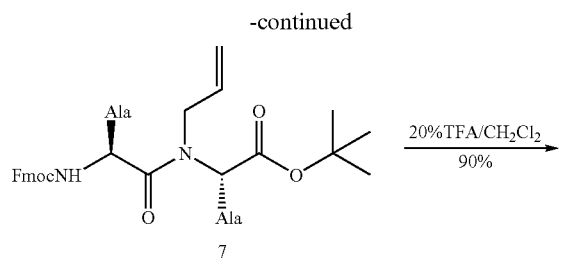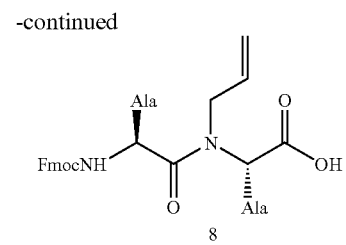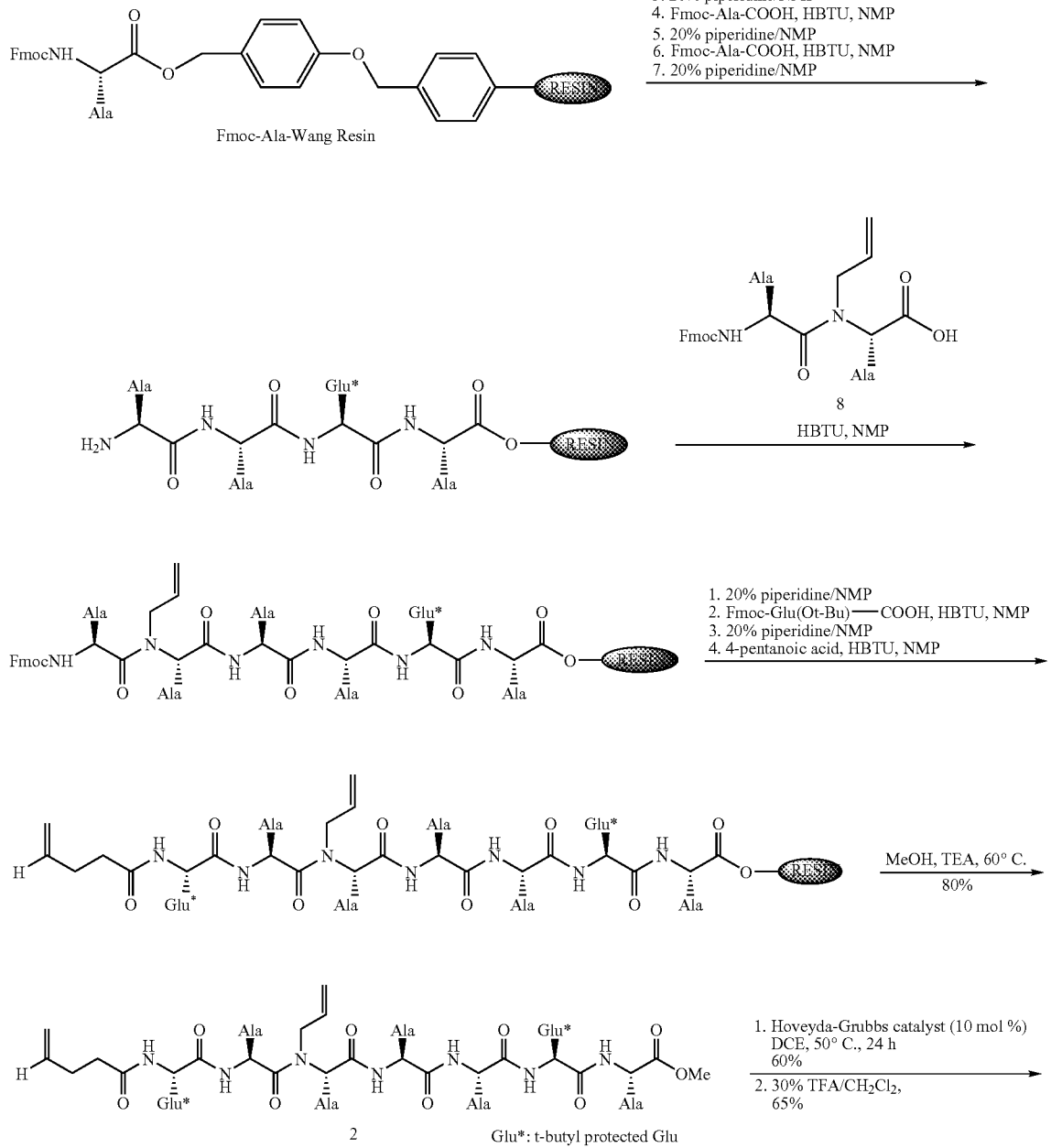

-continued

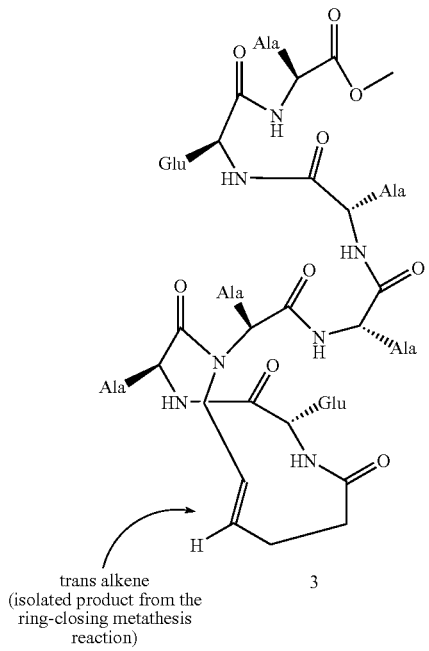

trans alkene 3
(isolated product from the
ring-closing metathesis
reaction)

The last step of the peptide synthesis included coupling with 4-pentenoic acid, which serves as an alkene-bearing glycine mimic. The peptide was cleaved from the resin as a C-terminal methyl ester with methanol and triethylamine, as shown in Scheme 6. These cleavage conditions were used to obtain peptide 2 with the two glutamic acid side chains protected as the t-butyl esters. The protecting groups were kept to increase the solubility of the peptide in organic solvents for the metathesis step and because carboxylic acids are known to react with the metathesis catalyst (Trnka et al., "The Development of L2X2Ru=CHR Olefin Metathesis Catalysts: An Organometallic Success Story," *Accounts Chem. Res.* 34:18–29 (2001), which is hereby incorporated by reference in its entirety).

Ring-Closing Metathesis Reaction

The ring-closing metathesis ("RCM") step was found to be challenging, and different RCM catalysts (including, for example, Grubbs 1$^{st}$ generation, Grubbs 2$^{nd}$ generation, and Hoveyda-Grubbs),

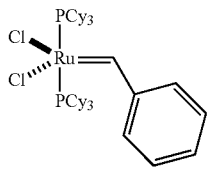

Grubbs Catalyst
1st Generation

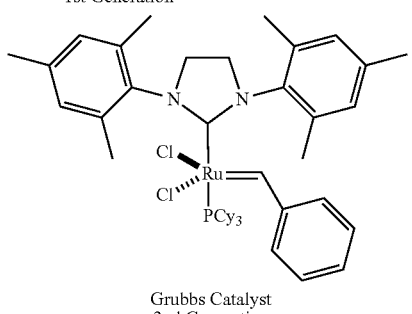

Grubbs Catalyst
2nd Generation

-continued

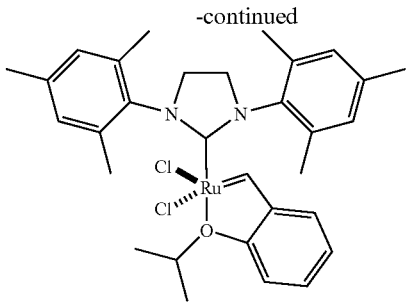

Hoveyda-Grubbs Catalyst various reaction temperatures (including, for example, 25° C., 40° C., 50° C., 80° C., and 110° C.), and solvent systems (including, for example, dichloromethane, dichloroethane, trichloroethane, and toluene) were used to optimize the metathesis reaction (Trnka et al., "The Development of L2X2Ru=CHR Olefin Metathesis Catalysts: An Organometallic Success Story," *Accounts Chem. Res.* 34:18–29 (2001); Hoveyda et al., "Ru Complexes Bearing Bidentate Carbenes: From Innocent Curiosity to Uniquely Effective Catalysts for Olefin Metathesis," *Org. Biomolec. Chem.* 2:8–23 (2004), which are hereby incorporated by reference in their entirety). The Hoveyda-Grubbs catalyst was found to afford the highest yield for the metathesis step (40–65% after HPLC purification). The Grubbs second generation catalyst afforded the metathesis product in 5–20% yields.

Typical RCM reactions yield a mixture of cis and trans alkene isomers, favoring trans for large macrocycles. RCM studies performed on a closely related 13-membered macrocyclization system have been reported to yield a trans to cis ration of ≧4:1 (Banerji et al., "Synthesis of Cyclic Beta-turn Mimics from L-Pro-Phe/Phe-L-Pro Derived Di- and Tripeptides Via Ring Closing Metathesis: The Role of Chirality of the Phe Residue During Cyclization," *Tetrahedron Lett. 43:6473–6477 (2002), which is hereby incorporated by reference in its entirety). HPLC analysis of the crude mixture showed a new peak corresponding to the trans isomer as indicated by $^1$H NMR spectroscopy and analysis of the alkene proton coupling constraints (16.2 Hz). The cis isomer was likely formed in small amounts, but its presence was not detected by HPLC. The macrocyclized peptide was purified by prep-HPLC and treated with TFA to remove the side chain protecting groups. The fully deprotected and constrained peptide was purified again by HPLC to obtain constrained peptide 3 in an overall yield of 50% from the linear peptide 2.

Materials and Methods

Commercial-grade reagents and solvents were used without further purification except as indicated. $CH_2Cl_2$ and DMF were dried prior to use by percolation through anhydrous $Al_2O_3$ as described by Grubbs and coworkers (Pangborn et al., *Organometallics*, 15:1518–1520 (1996), which is hereby incorporated by reference in its entirety). All reactions were stirred magnetically; moisture-sensitive reactions were performed under nitrogen in flame-dried glassware. Thin-layer chromatography (TLC), usually using either ethyl acetate/hexane or methanol/$CH_2Cl_2$ as the solvent system, was used to monitor reactions. Visualization was accomplished by either ultraviolet light or by immersing the plate in a 1% aqueous solution of potassium permanganate and heating. Flash chromatography with silica gel was performed following the conditions described by Still and coworkers (Burfield & Smithers, *J. Org. Chem.*, 43:3966–3968 (1978), which is hereby incorporated by reference in its entirety). Solvents were removed by rotary evaporation under reduced pressure; where appropriate, the residue was further dried using a vacuum pump. Reverse-phase HPLC experiments were conducted with 4.6×150 mm (analytical scale) or 21.4×150 mm (preparative scale) Waters $C_{18}$ reverse phase columns using a Beckman Coulter HPLC equipped with a System Gold 168 Diode array detector. The typical flow rates for analytical and preparative HPLC were 1 mL/min and 8 mL/min, respectively. In all cases, 0.1% aqueous TFA and acetonitrile buffers were used. Proton NMR spectra were obtained on a Bruker AV-400 (400 MHz), Bruker AV-500 (500 MHz), or Varian-200 (200 MHz) spectrometer. Carbon NMR spectra were obtained on a Bruker (100.5 MHz) spectrometer. Proton chemical shifts are reported as d values relative to tetramethylsilane (0.00 ppm) or to the particular solvent used in the experiment ($CDCl_3$: 7.26 ppm or $D_2O$: 4.80 ppm). Carbon chemical shifts are reported as d values relative to the particular solvent used in the experiment ($CDCl_3$: 77.0 ppm). Data is reported as follows: chemical shift, multiplicity (s=singlet, d=doublet, t=triplet, q=quartet, m=multiplet, dd=doublet of doublet, br=broad), coupling constant, and integration. Infrared (IR) spectra were obtained with a Thermo Nicolet Avatar 360 FTIR. High-resolution mass spectra (HRMS) were obtained by fast atom bombardment (FAB) of samples in m-nitrobenzyl alcohol with $Cs^+$ ions. FAB experiments were performed by MSU-NIH Mass Spectrometry Facility, East Lansing, Mich. LCMS data was obtained on an Agilent 1100 series LC/MSD (XCT) electrospray trap.

Synthesis of Compound 5

To synthesize o-NBS-N(Allyl)-Ala-OtBu 5, allyl bromide (0.650 mL, 7.60 mmol) was added to a solution of o-NBS-Ala-OtBu 4 (Turner et al., *Tetrahedron Lett.*, 40:7039–7042 (1999), which is hereby incorporated by reference in its entirety) (1.36 g, 4.12 mmol) and $K_2CO_3$ (1.15 g, 8.34 mmol) in dry DMF (20 mL). The mixture was stirred overnight, and then poured into water (20 mL). The aqueous layer was extracted with ether (3×30 mL) and the combined organic layers were dried ($MgSO_4$), filtered, and concentrated in vacuo to afford 1.53 g of compound 5 (100%) as a pale yellow solid ($^1$H NMR (400 MHz, $CDCl_3$) δ 8.10–8.05 (m, 1H), 7.69–7.66 (m, 2H), 7.62–7.59 (m, 1H), 5.85 (ddt, J=17.2, 10.2, 6.74 Hz, 1H), 5.20 (dd, J=10.2, 1.3 Hz, 1H), 5.08 (dd, J=17.2 Hz, J=1.2, 1H), 4.69 (q, J=7.3 Hz, 1H), 4.18 (dd, AB pattern, J=16.8, 6.2 Hz, 1H), 3.84 (dd, AB pattern, J=16.9, 6.2 Hz, 1H), 1.48 (d, J=7.3 Hz, 3H), 1.35 (s, 9H); $^{13}$C NMR (100 MHz) δ 170.26, 148.03, 135.11, 133.99, 133.37, 131.60, 131.27, 124.06, 117.86, 82.07, 56.64, 48.52, 27.80, 16.86; IR (film) 1733 $cm^{-1}$; HRMS (FAB) m/z for $C_{16}H_{23}N_2O_6S$ $[M+H]^+$, calcd 371.1229, found 371.1277).

Synthesis of Compound 6

To synthesize HN(Allyl)-Ala-OtBu 6, thiophenol (0.135 mL, 1.32 mmol) was added to a solution of o-NBS-N(Allyl)-Ala-OtBu 5 (0.400 g, 1.09 mmol) and $K_2CO_3$ (0.450 g, 3.25 mmol) in DMF (3 mL). After 2 hours, the reaction mixture was poured into water (3 mL). The aqueous layer was extracted with ether (3×30 mL), and the combined organic layers were extracted with 1 M HCl (3×25 mL). The pH of the combined aqueous layers was adjusted with saturated aqueous $NaHCO_3$ to pH 7.5. The aqueous layer was then extracted with ether (3×30 mL), dried ($MgSO_4$), filtered, and concentrated to yield 0.18 g of compound 6 (89%) as a yellow oil ($^1$H NMR (400 MHz, $CDCl_3$) δ 5.88 (ddt, J=17.1, 10.2, 6.1 Hz, 1H), 5.19 (dd, J=17.1, 1.5 Hz, 1H), 5.09 (dd, J=10.2, 1.5 Hz, 1H), 3.29–3.11 (m, 3H), 1.47 (s, 9H), 1.26 (d, J=7.0 Hz, 3H); $^{13}$C NMR (100 MHz) δ 175.06, 136.41, 116.11, 80.77, 56.47, 50.47, 28.44, 19.07; IR (film) 3299, 1723 $cm^{-1}$; HRMS (FAB) m/z for $C_{10}H_{20}NO_2$ $[M+H]^+$, calcd 186.1448, found 186.1494).

Synthesis of Compound 7

To synthesize Fmoc-Ala-N(Allyl)-Ala-OtBu 7, N,N-Dicyclohexylcarbodiimide (0.250 g, 1.19 mmol) was added to a solution containing Fmoc-Ala-OH (0.370 g, 1.19 mmol) and 1-hydroxybenzotriazole (0.160 g, 1.19 mmol) in DMF (10 mL). The mixture was stirred for 10 minutes and then compound 6 (0.202 g, 1.09 mmol) was added. After 18 hours, the reaction mixture was filtered, poured into 10 mL water, and extracted with ether (3×30 mL). The organic layer was dried ($MgSO_4$), filtered, and concentrated. The crude product was purified by flash chromatography (5:1 hexane-ethyl acetate) to afford 0.37 g of compound 7 (71%) as a colorless oil ($^1$H NMR (400 MHz, $CDCl_3$) δ 7.75 (d, J=7.5 Hz, 2H), 7.59 (d, J=7.3 Hz, 2H), 7.38 (t, J=7.4 Hz, 2H), 7.29 (t, J=7.4 Hz, 2H), 5.90 (ddt, J=16.9, 10.1, 8.1 Hz, 1H), 5.73 (d, J=8.1 Hz, 1H) 5.23–5.31 (m, 2H), 4.72–4.79 (m, 1H), 4.63 (quintet, J=7.1 Hz, 1H), 4.31–4.44 (m, 2H), 4.21 (t, J=7.1 Hz, 1H), 4.05 (dd, AB pattern, J=17.2, J=4.4, 1H), 3.87 (dd, AB pattern J=17.5, 5.0 Hz, 1H), 1.44 (s, 9H), 1.39 (d, J=3.0 Hz, 3H), 1.37 (d, J=2.3 Hz, 3H); $^{13}$C NMR (100 MHz) δ 173.15, 170.58, 155.44, 143.96, 141.29, 133.86, 127.68, 127.05, 125.18, 119.96, 117.63, 81.59, 66.92, 54.33, 48.32, 47.41, 47.17, 27.99, 19.41, 14.62; IR (film) 3299, 1730 $cm^{-1}$; HRMS (FAB) m/z for $C_{28}H_{35}N_2O_5$ $[M+H]+$ calcd 479.2501, found 479.2546).

Synthesis of Dipeptide 8

To synthesize Fmoc-Ala-N(Allyl)-Ala-OH 8, Fmoc-Ala-N(Allyl)-Ala-OtBu 7 (0.270 g, 0.650 mmol) was dissolved in a solution of trifluoroacetic acid (2 mL) and $CH_2Cl_2$ (10 mL). The mixture was stirred at room temperature and the reaction progress monitored by TLC. After 2 hours, the mixture was concentrated and the residue was redissolved in 10 mL of ethyl acetate and washed with water (2×10 mL). The organic layer was extracted with saturated aqueous NaHCO$_3$ (3×10 mL), and the combined aqueous layers were washed with EtOAc (2×10 mL). The aqueous fraction was then acidified to pH 2 with concentrated aqueous HCl and extracted with ethyl acetate (3×10 mL). The combined organic layers were dried (MgSO$_4$), filtered, and concentrated to afford 0.250 g (90%) of dipeptide 8 as a white solid ($^1$H NMR (400 MHz, CDCl$_3$) δ 7.75 (d, J=7.5 Hz, 2H), MeOH (3×) and ether (3×). The resulting amine was treated with activated Fmoc-Glu(OtBu)-OH (0.750 mmol, 0.319 g), HBTU (0.675 mmol, 0.256 g) and 5% DIEA/NMP for 45 minutes, followed by washings with DMF (3×), DCM (3×), MeOH (3×) and ether (3×). This procedure was repeated for the introduction of the remaining amino acids, dipeptide 8, and pentenoic acid residues. Treatment of the resin with TEA:MeOH (1:10) at 50° C. for 16 hours afforded crude peptide 2. Column chromatography (gradient:1% MeOH/DCM to 4% MeOH/DCM) afforded 171 mg (64.8%) of peptide 2 as a white solid (ESIMS for C$_{42}$H$_{70}$N$_7$O$_{13}$ [M+H]+calcd 880.5, found 880.4).

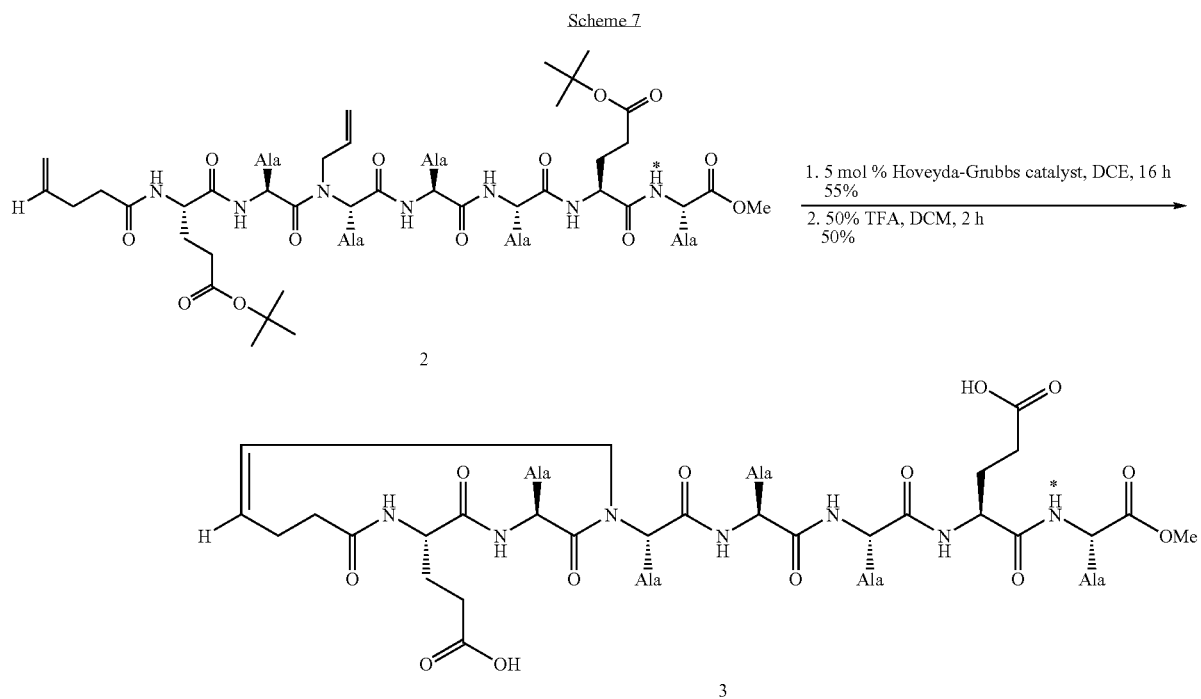

7.48–7.59 (m, 2H), 7.39 (t, J=7.4 Hz, 2H), 7.30 (t, J=7.4, 2H), 5.97–5.84 (m, 1H), 5.83 (d, J=8.3 Hz, 1H), 5.26–5.33 (m, 2H), 5.32–5.21 (m, 2H), 4.63–4.72 (m, 1H), 4.66–4.58 (m, 1H), 4.35 (d, J=7.3 Hz, 2H), 4.18–4.22 (m, 1H), 4.08 (dd, AB pattern, J=11.8, 5.4 Hz, 1H), 4.97 (dd, AB pattern, J=12.8, 4.7 Hz, 1H), 1.48 (d, J=7.3 Hz, 3H), 1.39 (d, J=6.8 Hz, 3H); $^{13}$C NMR (100 MHz) δ 175.61, 173.94, 155.66, 143.93, 143.81, 141.28, 133.27, 127.69, 127.05, 125.22, 119.9, 118.93, 67.04, 54.06, 48.97, 47.41, 47.11, 27.59, 19.05, 15.87, 14.37; IR (film) 3400, 3297, 1719 cm$^{-1}$; HRMS (FAB) m/z for C$_{24}$H$_{27}$N$_2$O$_5$ [M+H]+calcd 423.1874, found 423.1920).

Synthesis of Peptide 3

Constrained peptide 3 was synthesized as shown in Scheme 7. The modified octapeptide 2 was prepared by conventional Fmoc solid phase chemistry. The pre-loaded Fmoc-Ala Wang resin was purchased from NovaBiochem. The Fmoc group was removed from Fmoc-Ala (0.3 mmol, 441.18 mg) by treatment with 20% piperidine in NMP (2×20 min), followed by washings with DMF (3×), DCM (3×), To a solution of bis olefin peptide 2 (60.0 mg, 68.0 μmol) in 2 mL of anhydrous dichloroethane at 50° C. was added a solution of Hoveyda-Grubbs catalyst (2.14 mg, 3.40 μmol) in 0.270 mL anhydrous dichloroethane. After 16 hours, the reaction mixture was concentrated under vacuum and purified by HPLC to afford 31.8 mg (55%) of the t-butyl ester protected constrained peptide as a white solid (ESIMS for C$_{40}$H$_{66}$N$_7$O$_{13}$ [M+H]+calcd 852.5, found 852.5).

Figure 2:
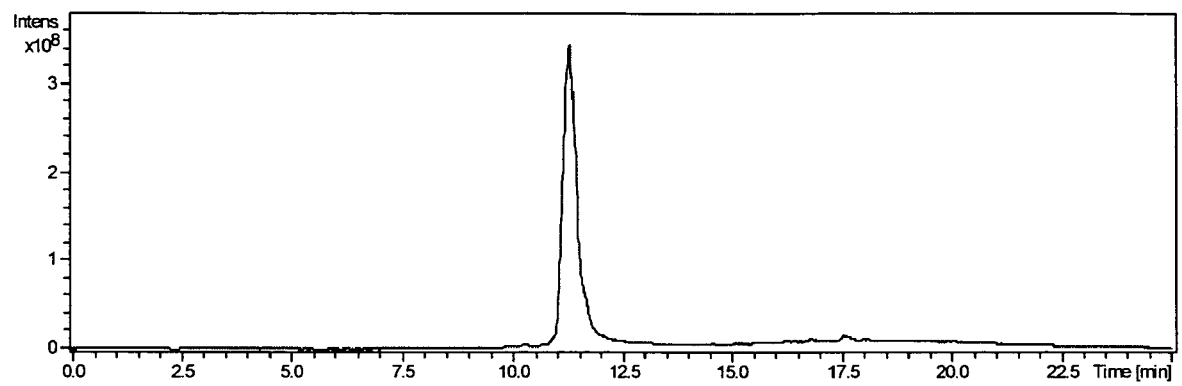
FIG. 2 is a reverse-phase HPLC plot of purified constrained α-helix 3. The HPLC conditions were as follows: C18 reverse phase column; 20–100% B in 15 mins; A: 0.1% aqueous TFA, B: acetonitrile; flow rate: 0.2 mL/min.

The protected peptide (20.0 mg, 23.5 μmol) was dissolved in TFA (2.5 mL) and CH$_2$Cl$_2$ (2.5 mL), and the reaction progress was monitored by TLC. After 3 hours, the reaction mixture was concentrated and purified by HPLC (see FIG. 2 and accompanying text) to yield the cyclized deprotected peptide 3 as a white solid in 8.7 mg (50.2%) (ESIMS for C$_{32}$H$_{50}$N$_7$O$_{13}$ [M+H]+calcd 740.3, found 740.2).

The control peptide 1 (AcGEAAAAEA (SEQ ID NO: 34)) was prepared by conventional Fmoc solid phase chemistry on Wang resin and was cleaved as a methyl ester with methanol and triethylamine as described above for peptide 2 (ESIMS for C$_{30}$H$_{49}$N$_{8O14}$ [M+H]$^+$calcd 745.3, found 745.7).

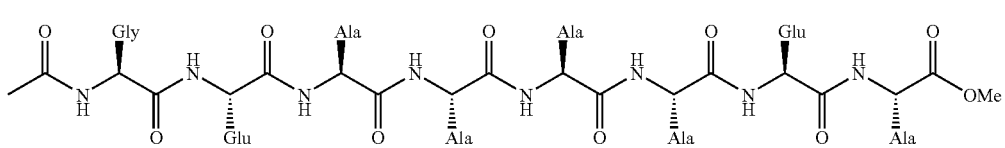

Analysis Of Constrained Peptide 3

Circular Dichroism

Figure 3:
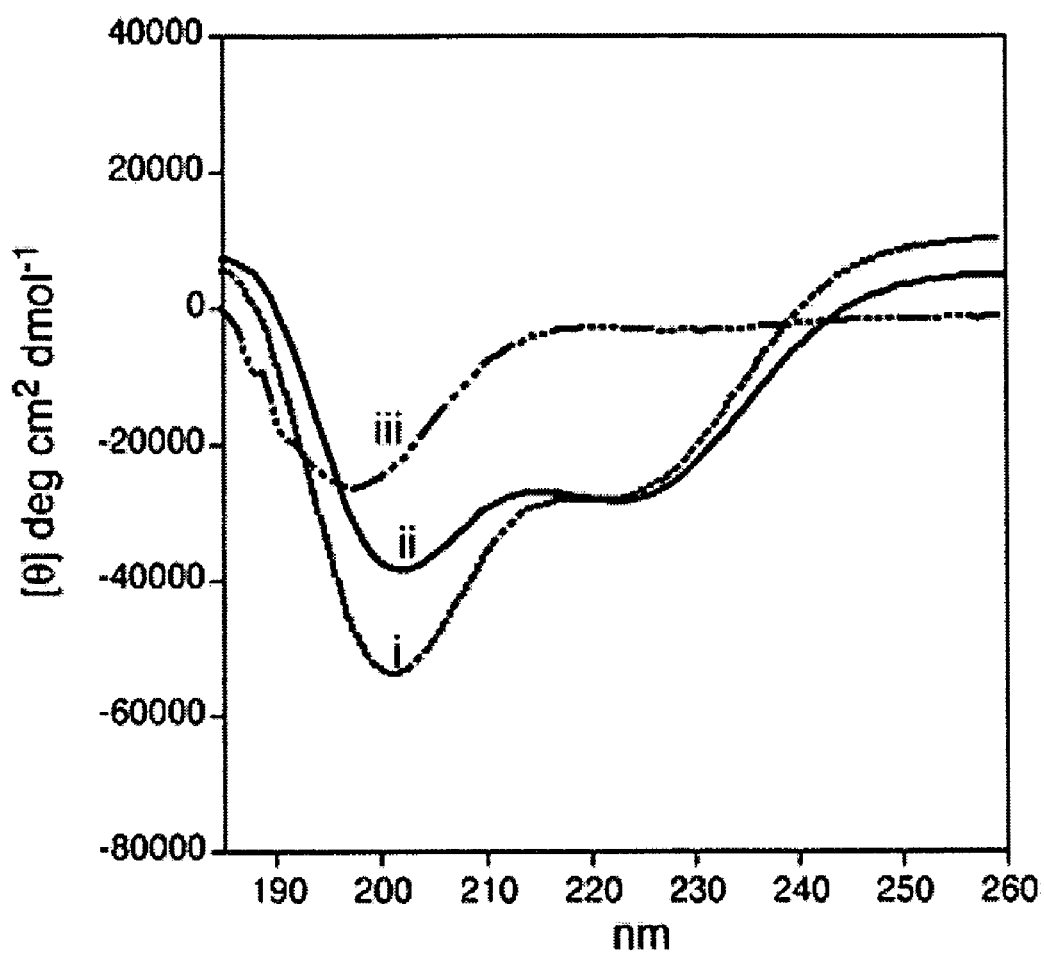
FIG. 3 is circular dichroism spectra of (i) α-helix 3 in 30 mM phosphate buffer (pH 7.0); (ii) α-helix 3 in 20% TFE/phosphate buffer; and (iii) unconstrained peptide 1 in phosphate buffer. The spectra were recorded at 25° C.

The structure of constrained peptide 3 was studied with circular dichroism ("CD"). CD studies on the constrained peptide 3 and the control peptide 1 in 30 mM phosphate buffer pH 7.0 were performed to obtain a quantitative measure of the helical content. The results are shown in FIG. 3. As can be seen in FIG. 3, the CD spectrum of peptide 3 displays a double minimum at 209 nm and 222 nm, characteristic of α-helices (Marqusee et al., "Helix Stabilization by Glu⁻ . . . Lys⁺ Salt Bridges in Short Peptides of de novo Design," *Proc. Nat'l Acad. Sci. U.S.A.* 84:8898–8902 (1987), which is hereby incorporated by reference in its entirety). The relative percent helicity of peptides can theoretically be measured by the mean residue ellipticity at 222 nm (Lyu et al., "Alpha-helix Stabilization by Natural and Unnatural Amino Acids with Alkyl Side Chains," *Proc. Nat'l Acad. Sci.* 88:5317–5320 (1991), which is hereby incorporated by reference in its entirety), although these estimates are not typically accurate for short helices.

As seen in FIG. 3, the observed mean residue ellipticity ($[\theta]_{obsd}$) for peptide 3 is −31000 in 20% trifluoroethanol ("TFE") and phosphate buffer (ii) and phosphate buffer (i), calculated per mole of amide groups present. The calculated maximal mean residue ellipticity value ($[\theta]_{max}$) for the constrained peptide is −25000 and −275000 deg cm² dmol⁻¹ based on Yang's method (Chen et al., "Determination of the Secondary Structures of Proteins by Circular Dichroism and Optical Rotatory Dispersion," *Biochemistry* 11:4120–4131 (1972), which is hereby incorporated by reference in its entirety) and Baldwin's (Chin et al., "Circular Dichroism Spectra of Short, Fixed-nucleus Alanine Helices," *Proc. Nat'l, Acad. Sci. U.S.A.* 99:15416–15421 (2002), which is hereby incorporated by reference in its entirety) correction for short peptides. Accordingly, this constrained peptide was estimated to be 100% helical. As expected, the unconstrained peptide 1 showed a featureless spectrum in aqueous buffer (FIG. 3 (iii)) and TFE solutions.

Figure 4:
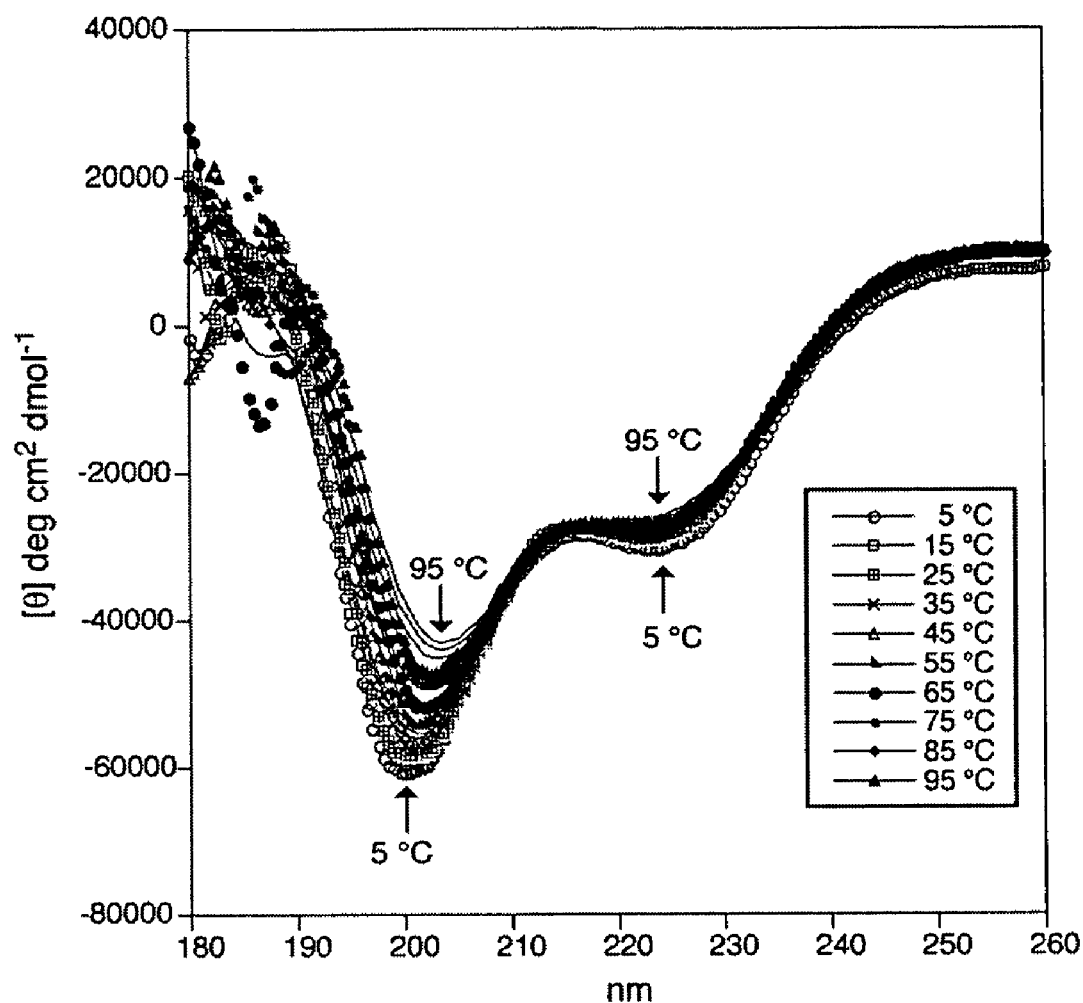
FIG. 4 is a graph illustrating the effect of temperature on helicity of α-helix 3.

CD spectra were recorded on an AVIV 202SF CD spectrometer equipped with a temperature controller using 1 mm path length cells. The scan speed was set to 5 nm/min and spectra were averaged over 5 scans. Spectral baselines were obtained under analogous conditions as that for the samples. All spectra are baseline subtracted, converted to a uniform scale of molar ellipticity, and replotted. The helix content of each peptide was determined from the mean residue CD at 222 nm, $[\theta]_{222}$ (deg cm² dmol⁻¹) corrected for the number of amide bonds (Chin et al., *Proc. Nat'l Acad. Sci. U.S.A.*, 99:15416–15421 (2002); Chen et al., *Biochemistry*, 11:4120–4131 (1972), which are hereby incorporated by reference in their entirety). CD measurements were performed at a peptide concentration of 50 μM in 30 mM phosphate buffer (pH 7.0) at 25° C. unless indicated otherwise. Varied temperature CDs were allowed to equilibrate at the given temperature for 30 minutes before each run. FIG. 4 shows the CD spectra of peptide 3 at various temperatures between 5° C. and 95° C. The intensity of 222 nm band remains essentially constant while that of the 202 nm band changes slightly.

Denaturation Studies

Figure 5:
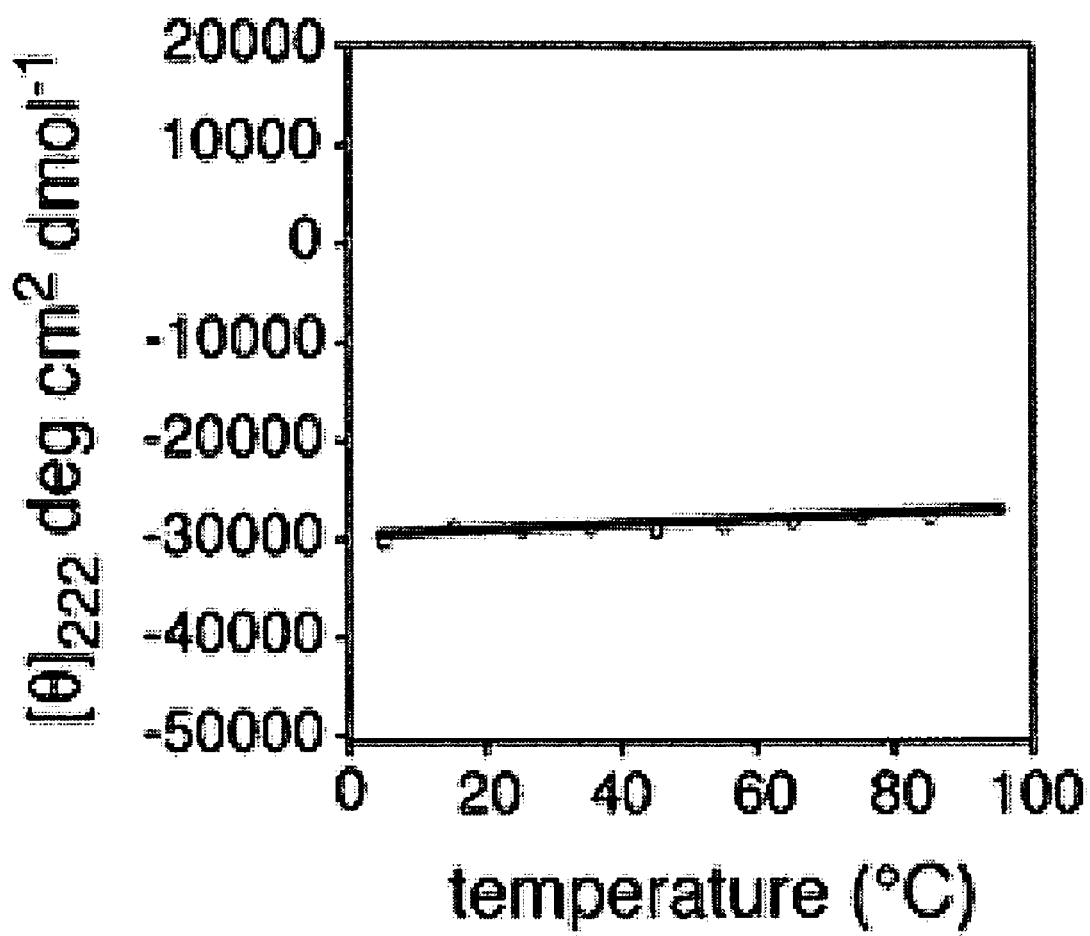
FIG. 5 is a graph illustrating the effect of temperature on stability of α-helix 3.
Figure 6:
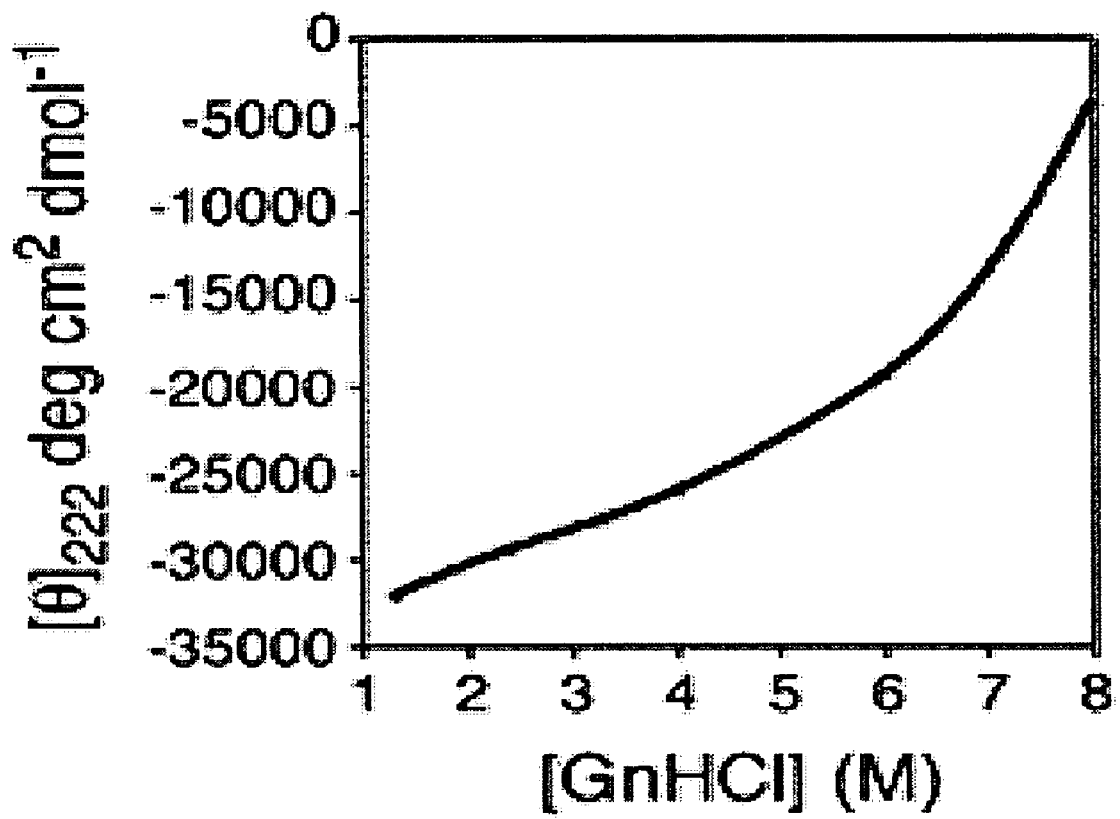
FIG. 6 is a graph illustrating the effect of GnHCl on stability of α-helix 3.

Thermal and guanidinium chloride ("GnHCl") denaturation studies were performed to determine the stability of artificial α-helix 3. Referring now to FIG. 5, it is shown that the constrained peptide remains helical when heated from 5° C. to 95° C., indicating that the peptide is structurally robust. The results of GnHCl titration experiments are shown in FIG. 6. The intensity of the $[\theta]_{222}$ transition for the constrained peptide remained essentially unchanged (85% helical) up to a concentration of 4M GnHCl. The peptide started to unravel between 6–8M GnHCl. These CD studies illustrate that peptide 3 clearly adopts a highly stable constrained α-helix structure whose stability compares favorably to highly stable α-helical coiled-coil motifs (Litowski, et al., "Designing Heterodimeric Two-stranded Alpha-helical Coiled-coils: Effects of Hydrophobicity and Alpha-helical Propensity on Protein Folding, Stability, and Specificity," *J. Biol. Chem.* 277:37272–37279 (2002), which is hereby incorporated by reference in its entirety), and to a previously reported constrained α-helix with three side-chain lactam bridges (Osapay & Taylor, *J. Am. Chem. Soc.*, 114:6966–6973 (1992), which is hereby incorporated by reference in its entirety).

NMR Analysis

Figure 7:
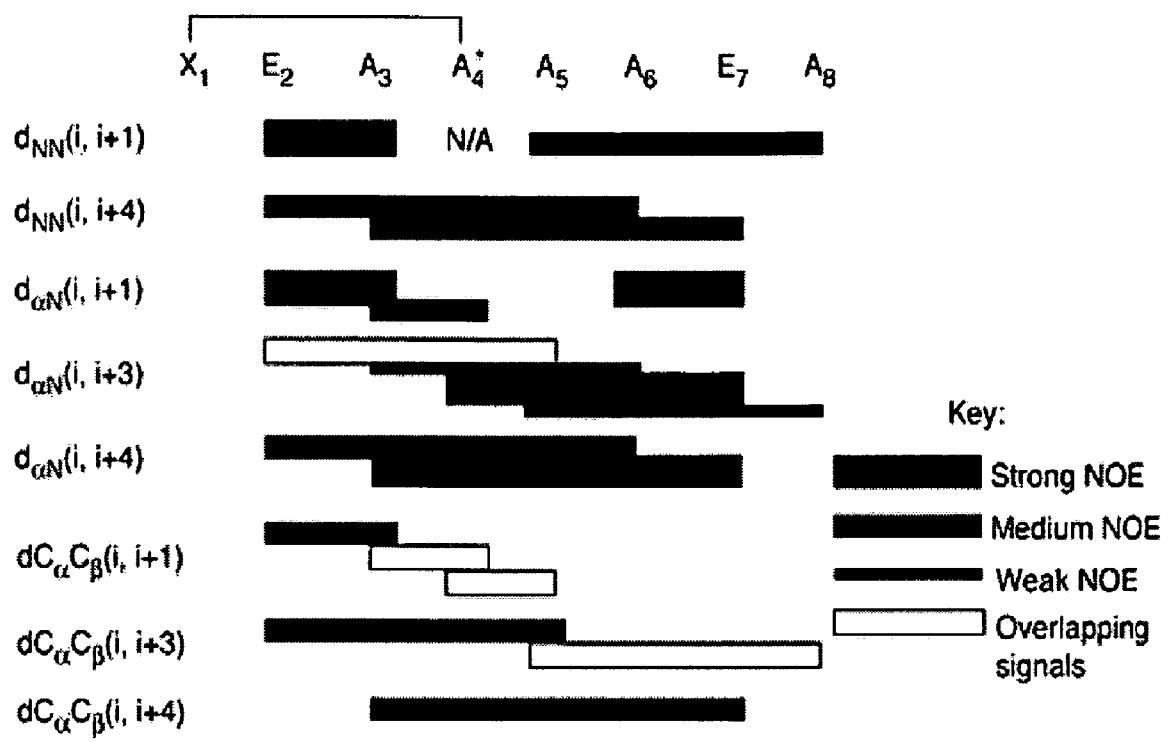
FIG. 7 is an NOE ROESY correlation chart for α-helix 3. The alanine-4 residue does not contain an NH. Filled rectangles indicate relative intensity of the NOE crosspeaks. Empty rectangles indicate NOE that could not be unambiguously assigned due to overlapping signals.

The α-helix structure of peptide 3 was further confirmed by 1D and 2D NMR spectroscopy. A combination of 2D total correlation spectroscopy ("TOCSY") and rotating frame overhauser enhancement spectroscopy ("ROESY") spectra was used to assign ¹H NMR resonances for the constrained peptide. Sequential NN (i and i+1) ROESY crosspeaks, which provide a strong evidence for α-helical structure, were observed for the entire sequence, as shown in FIG. 7.

The ROESY spectrum also reveals several medium range NOEs, e.g. $d_{\alpha N}(i, i+3)$, that provide unequivocal evidence for the helical structure. The fact that NOEs involving the last residue (alanine-8) can be detected indicates that the helix has not started fraying at the ends.

The ROESY and TOCSY experiments were performed at 40° C. in slightly acidic phosphate buffer (pH 6.2), which was determined to be the optimum pH for the ROESY experiments. This unusually high temperature was used, because aggregation (as detected by ¹H NMR) of this very hydrophobic peptide was observed at lower temperatures for samples at NMR concentration (1 mM) in the acidic buffer. It is a further indication of the stability of this helix that strong ROESY crosspeaks can be observed at 40° C.

These results demonstrate that the replacement of a hydrogen bond between the i and i+4 residues at the N-terminus of a short peptide with a carbon-carbon bond results in a highly stable constrained α-helix at physiological conditions as indicated by CD and NMR spectroscopies. A significant advantage of this strategy is that it allows access to short α-helices with strict preservation of molecular recognition surfaces required for biomolecular interactions.

NMR experiments were carried out in a solution of 10% D₂O in 30 mM phosphate buffer, pH 6.2 at 40° C. These conditions were determined to be optimum for this peptide for the ROESY studies, as aggregation of the peptide was observed at lower temperatures. All experiments were performed at a peptide concentration of 1 mM. The proton resonances for the constrained peptide were numbered according to amino acid residues $X_1E_2A_3A_4{}^*A_5A_6E_7A_8$, where X refers to the pentenoic acid residue and A* to the N-allylalanine residue. These resonances were assigned by means of TOCSY and ROESY experiments.

Figure 8:
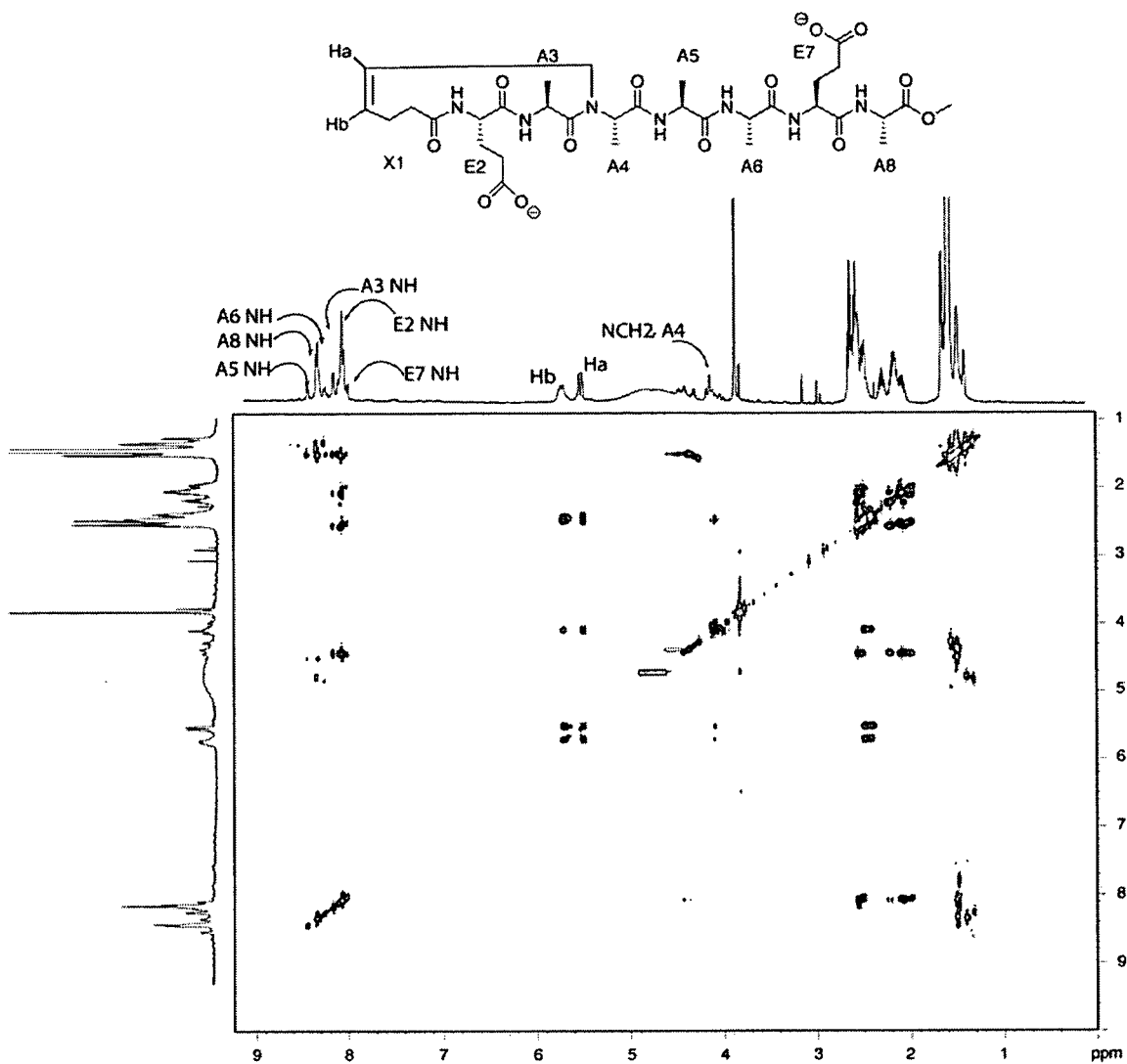
FIG. 8 is an image of the TOCSY spectrum of α-helix 3. The region between 3.80 and 5.00 ppm has suppressed peaks in the 1D 1H NMR due to the water peak suppression-related effects.

$^1$H NMR TOCSY studies on the constrained helix 3 were performed on Bruker Avance 500 spectrometer. TOCSY spectra were recorded at 313 K with a mixing time of 70 minutes. An 8.1 μsec 90° pulse was employed to collect 2k points in f2 domain and 256 points in f1 domain. The data were processed using Bruker XWINNMR software on a HP Workstation X1100. A 90° sine-squared window function was applied in both directions. The data were zero-filled to give a final matrix of 1k by 1k real points. The TOCSY spectrum is shown in FIG. 8.

Figure 9:
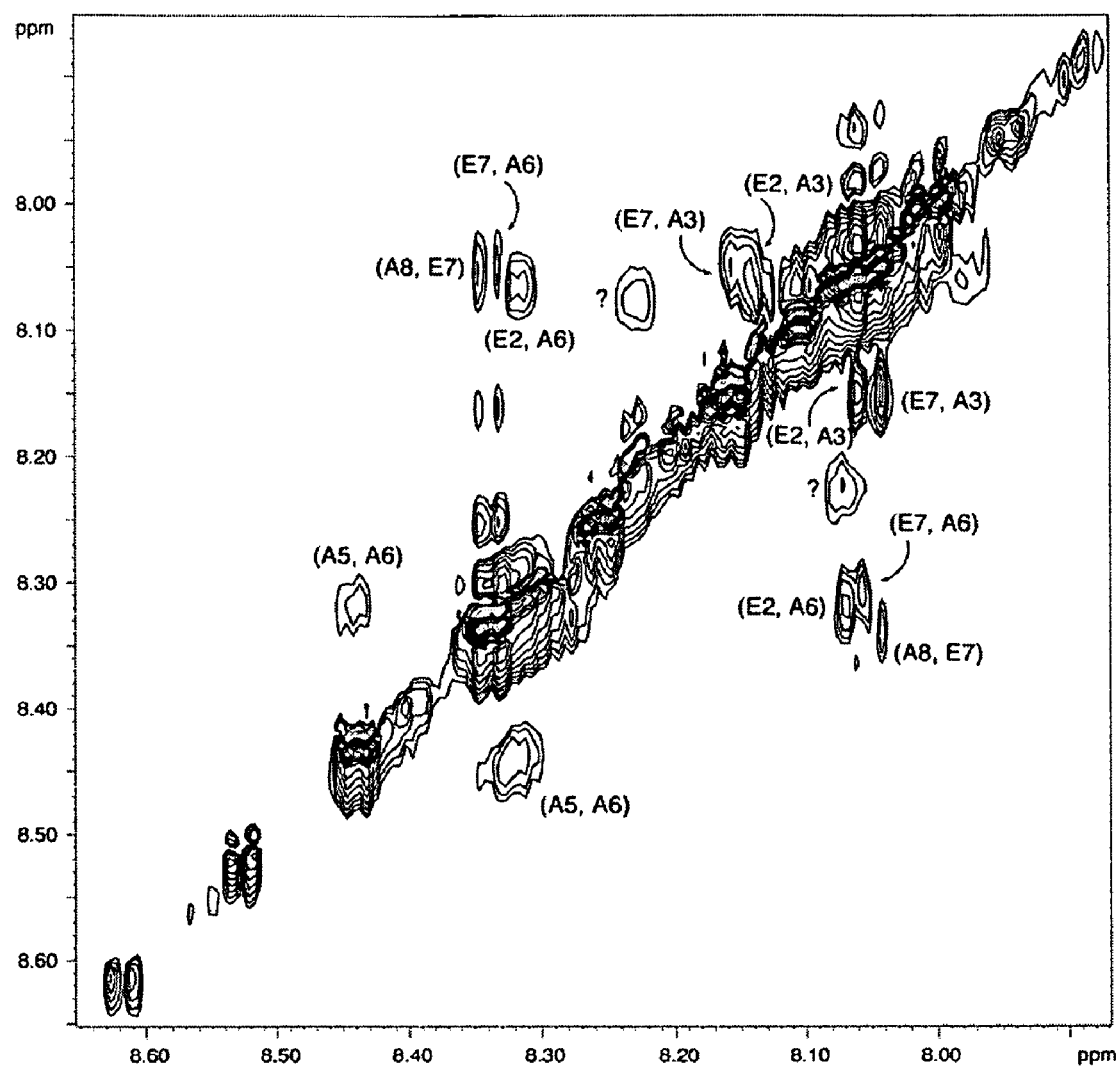
FIG. 9 is an image depicting the amide NH—NH region from the ROESY spectrum of α-helix 3.
Figure 10:
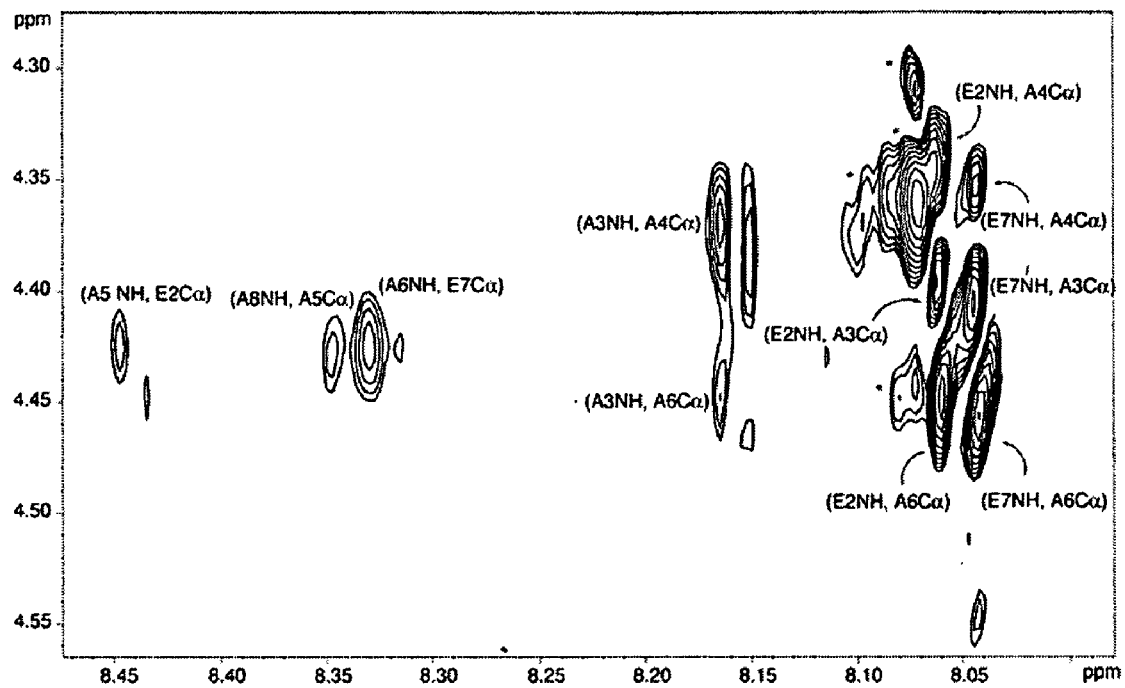
FIG. 10 is an image depicting the amide NH—Cα region from the ROESY spectrum of α-helix 3. * indicates NOE crosspeaks (at 8.07 ppm) that result from peptide aggregation over time (as deduced from comparison of NMR experiments run at lower pH's and temperatures).

$^1$H NMR pfg-ROESY studies on 3 were performed on Bruker Avance 500 spectrometer. The ROESY spectra were recorded at 313 K with a mixing time of 200 minutes using the pfg-ROESY pulse sequence. A ROESY continuous wave spin-lock of 1.5 KHz was used to collect 2k points in the f2 domain and 256 points in the f1 domain. The data were processed using Bruker XWINNMR software on an HP Workstation X1100. A 90° sine-squared window function was applied in both directions. The data were zero-filled once in f1 domain to give a final matrix of 1k by 1k real points. Important ROESY cross-peaks are shown in FIGS. 9 and 10.

Example 2

Preparation of Other Peptidomimetics

Figure 11:
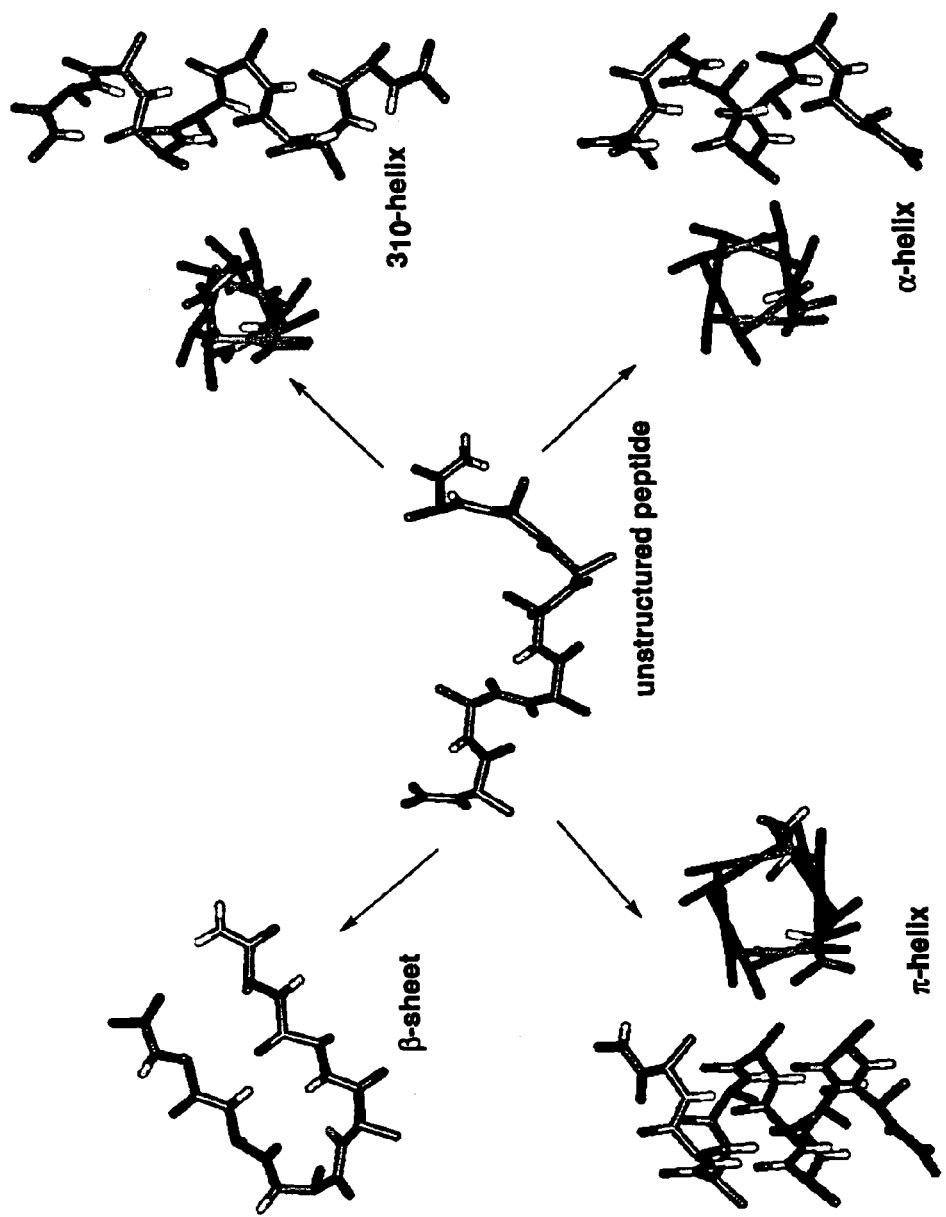
FIG. 11 is a schematic diagram illustrating four common peptide secondary structures.
Figure 12:
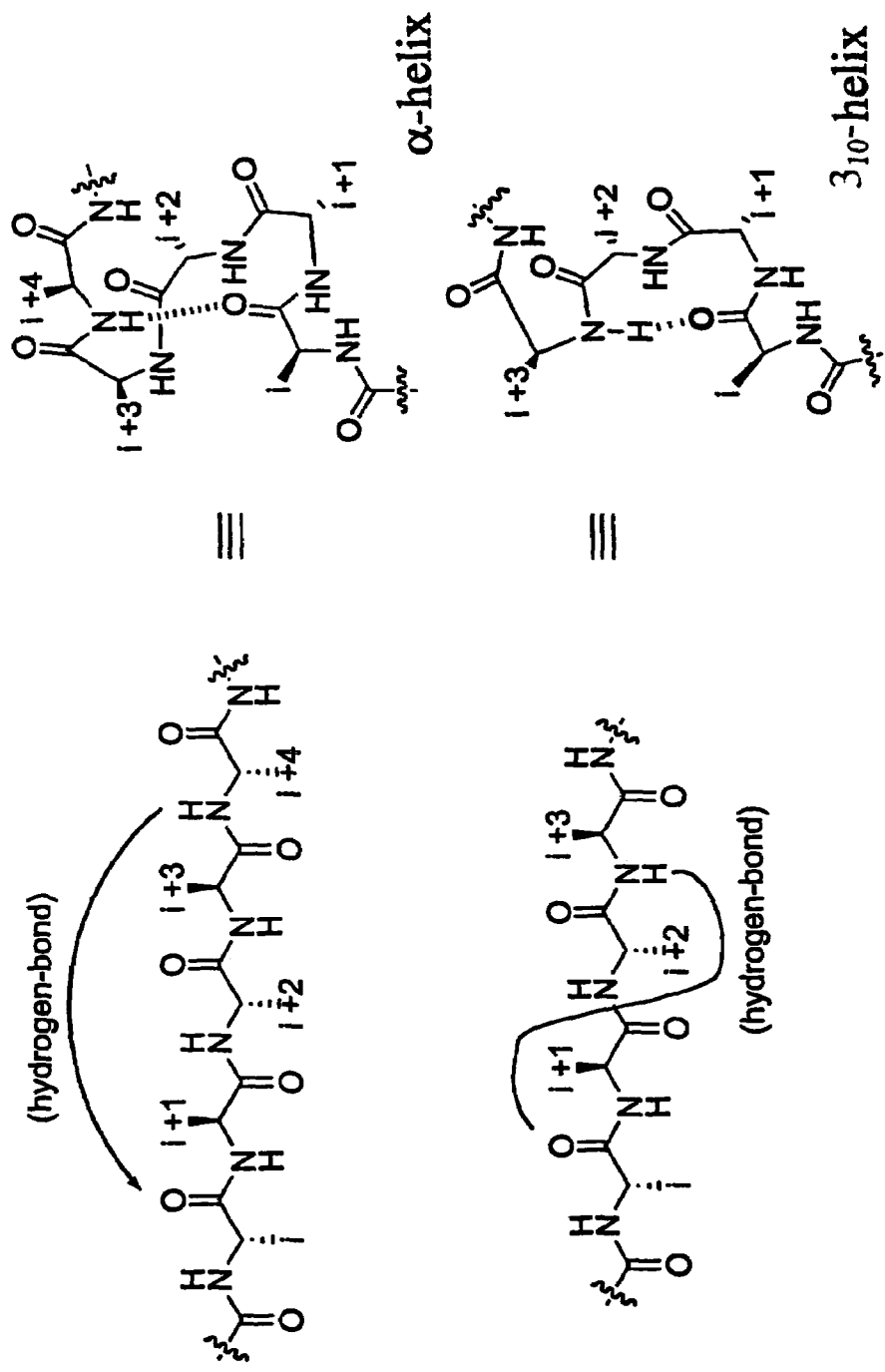
FIG. 12 is a schematic diagram illustrating the hydrogen bonding patterns of α- and 3₁₀-helices.

FIG. 11 shows common peptide secondary structures. These secondary structures are defined by hydrogen-bonding patterns, as demonstrated in FIG. 12. As shown in Scheme 8, the peptide modification methodology of the present invention not only allows preparation of artificial α-helices, but also of β-sheets/β-turns, 3$_{10}$-helices, and π-helices. These secondary structures may be prepared with the RCM method or the alkylation/macrocyliziation strategy as discussed previously for internally-constrained α-helices.

Scheme 8

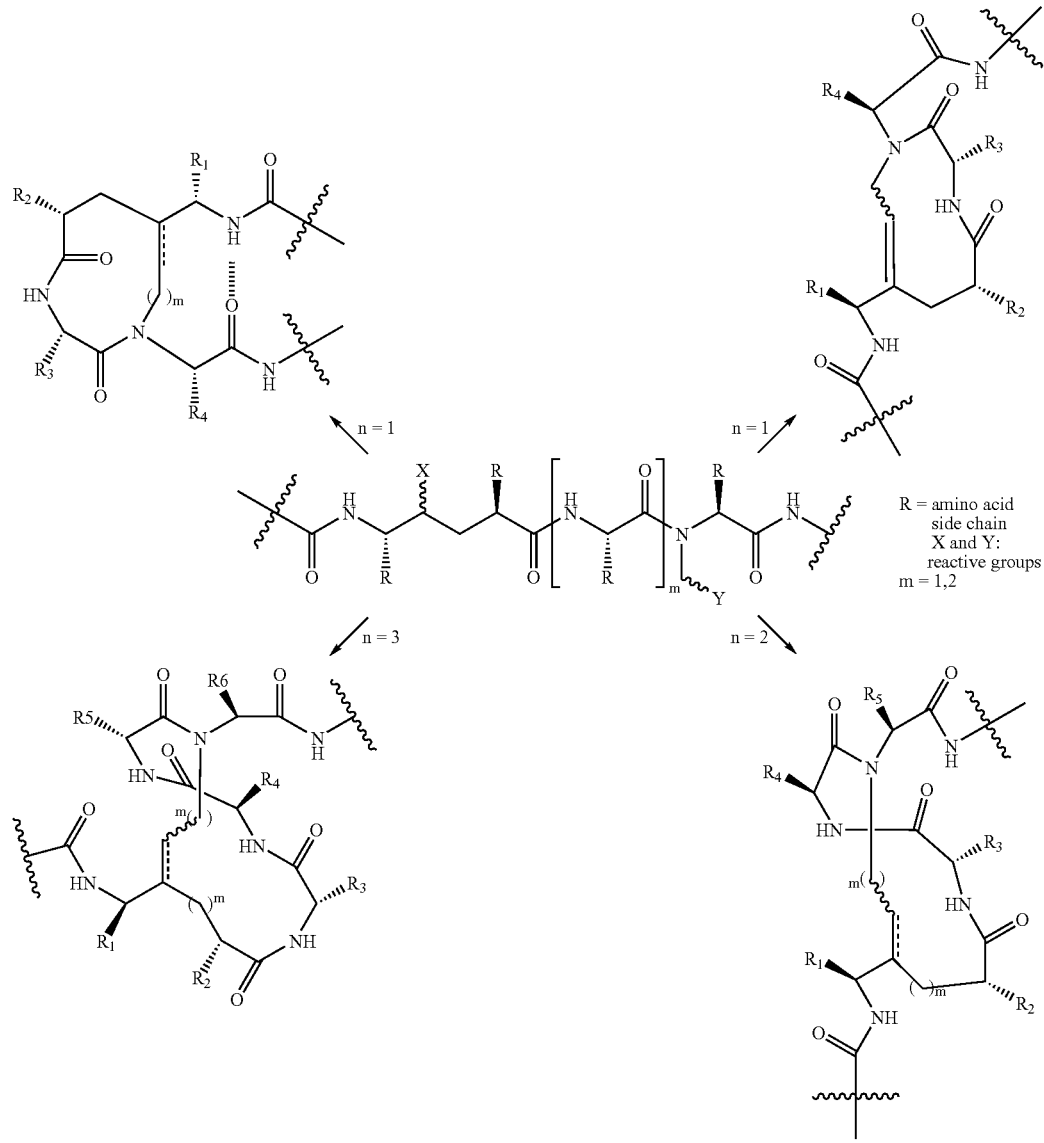

Example 3

Stabilization of BAK BH3 α-Helical Region

Example 1 demonstrates that the hydrogen-bond surrogate approach of the present invention affords highly stable α-helices from alanine-rich peptide sequences. This Example demonstrates the use of the hydrogen bond-surrogate approach of the present invention for the stabilization of biologically-relevant α-helices. This method can effectively stabilize α-helical conformations in non-alanine rich sequences. The resulting molecules resist proteolytic degradation as compared to their unconstrained analogs and bind their protein targets with high affinity.

Bak BH3

Bcl-xL is an extensively studied α-helix binding protein (Sattler et al., *Science* 275:983–986 (1997), which is hereby incorporated by reference in its entirety). Bcl-xL is an anti-apoptotic protein that regulates cell death by binding the α-helical BH3 domain of a family of pro-apoptotic proteins (such as Bak, Bad, Bid, and Bax) (Cory et al., *Oncogene*, 22:8590–8607 (2003); Letai et al., *Cancer Cell*, 2:183–192 (2002); Rutledge et al., *Curr. Opin. Chem. Biol.* 6:479–485 (2002), which are hereby incorporated by reference in their entirety). NMR studies by Fesik and coworkers have shown that a 16mer peptide 9a derived from the Bak BH3 domain adopts an α-helical conformation on binding to Bcl-xL (Sattler et al., *Science,* 275:983–986 (1997), which is hereby incorporated by reference in its entirety). Circular dichroism (CD) studies demonstrate that this peptide is not structured at physiological conditions in the absence of the protein partner and is only slightly helical in 30% trifluoroethanol (TFE), a helix promoting solvent (Petros et al., *Protein Sci.* 9:2528–2534 (2000), which is hereby incorporated by reference in its entirety).

Several methods that afford stabilized α-helices or helix mimetics have already been used to target Bcl-xL, allowing the direct evaluation of the performance of the internally-constrained artificial α-helices of the present invention (Kutzki et al., "Development of a Potent Bcl-x(L) Antagonist Based on Alpha-helix Mimicry," *J. Am. Chem. Soc.* 124:11838–11839 (2002); Chin & Schepartz, *Agnew. Chem. Int. Ed. Engl.,* 40:3806–3809 (2001); Degterev et al., *Nature Cell Biol.,* 3:173–182 (2001), which are hereby incorporated by reference in their entirety). Significantly, it was reported that Bak BH3 α-helices stabilized by a lactam-based side chain cross-linking strategy were unable to bind Bcl-xl (Yang et al., *Bioorg. Med. Chem. Lett.* 14:1403–1406 (2004), which is hereby incorporated by reference in its entirety). In this report, Huang and coworkers speculated that the lack of binding might be due to steric clashes between the cross-link and the narrow binding pocket of Bcl-xL. In a related study, Verdine, Korsmayer and coworkers reported that side chain bridged α-helices corresponding to the BH3 domain of a different pro-apoptotic protein, Bid, can target Bcl-xL and suppress the growth of leukemia cells in mice (Walensky et al., *Science* 305:1466–1470 (2004), which is hereby incorporated by reference in its entirety). Their report highlights the potential of constrained α-helices as tools for the control of protein-protein interactions in vivo. However, taken together these two protein binding studies from the Huang and Verdine laboratories illustrate potential problems with the side chain bridging strategy. It is believed that an important advantage of the hydrogen-bond surrogate approach of the present invention over the side chain bridging strategy for preparation of stabilized helices is that the helix surfaces are not encumbered by the constraining element. Judicious placement of the side-chain constraints requires prior knowledge of the protein-ligand complex; otherwise, multiple randomly constrained helices must be prepared and tested. The hydrogen-bond surrogate approach is expected to greatly simplify the helix design process. Artificial α-helices mimicking Bak BH3 were prepared according to the hydrogen-bond surrogate approach of the present invention, and their effectiveness for targeting Bcl-xL was examined. This Example addresses whether the HBS-derived Bak α-helix can bind Bcl-xL although the side-chain constrained (lactum bridge) Bak helix was unable to bind to this same target protein receptor.

Synthesis of Artificial Bak BH3

The artificial Bak BH3 α-helix 10a has the following structure:

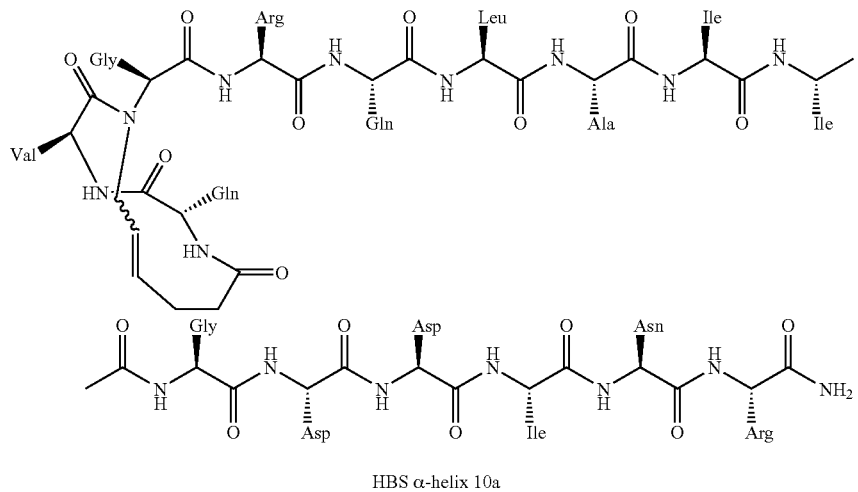

HBS α-helix 10a

It was synthesized on Wang resin by the ring closing metathesis reaction as shown in Scheme 9. Hydrogen bond surrogate α-helices can be synthesized from commercially available amino acids or simple amino acid derivatives and do not require preparation of enantiomerically pure amino acid analogs. In the present case, standard solid phase peptide synthesis utilizing appropriate Fmoc amino acids, dipeptide 11, and pentenoic acid afforded the fully-protected resin-bound bis-olefin peptide 12, which was subjected to the Hoveyda-Grubbs ring-closing metathesis catalyst to afford the peptide macrocycle (Chapman et al., *J. Am. Chem. Soc.*, 126:12252–12253 (2004); Hoveyda et al., *Org. Biomolec. Chem.*, 2:8–23 (2004), which are hereby incorporated by reference in their entirety). The metathesized peptide was cleaved from the resin with trifluoroacetic acid to obtain the constrained peptide 10a as a mixture of the cis and trans alkene isomers. The isomers were not able to be separated by HPLC.

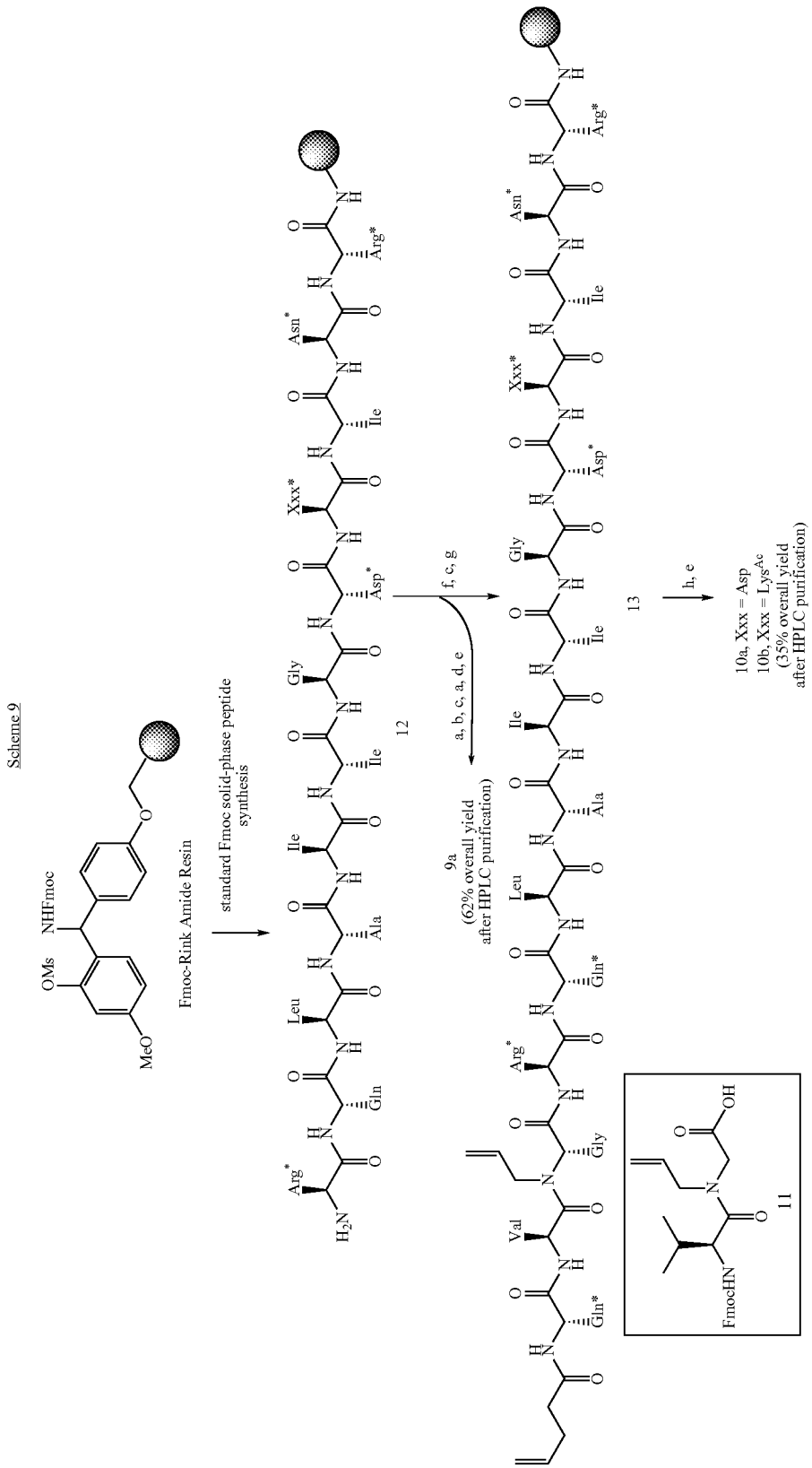

Scheme 9. Solid phase synthesis of HBS α-helices 10a–b:
(a) (i) Fmoc Gly-OH (3.2 equiv), HBTU (2.88 equiv), iPr₂NEt, NMP; (ii) piperidine, NMP;
(b) (i) Fmoc Val-OH (3.2 equiv), HBTU (2.88 equiv), iPr₂NEt, NMP; (ii) piperidine, NMP;
(c) (i) Fmoc Gln*-OH (3.2 equiv), HBTU (2.88 equiv), iPr₂NEt, NMP; (ii) piperidine, NMP;
(d) acetic anhydride, iPr₂NEt, DMF;
(e) CF₃CO₂H/H₂O/triisopropylsilane (95:2.5:2.5), 1.5 hours;
(f) (i) 11 (3.2 equiv), HBTU (2.88 equiv), iPr₂NEt, NMP; (ii) piperidine, NMP;
(g) pentenoic acid (3.2 equiv), HBTU (2.88 equiv), iPr₂NEt, NMP;
(h) 20 mol% Hoveyda-Grubbs Catalyst, dichloroethane, 50° C., 24 hours; Arg*:Pbf-protected Arg;Asn*:trityl-protected Asn; Asp*:t-butyl-protected Asp; Gln*:trityl protected Gln; Xxx*:Asp* or Lys(Ac);HBTU = O-(1H-benzotriazoyl-1-1yl)-N,N,N′,N′-tetramethyluronium hexafluorophosphate; NMP = N-methyl pyrrorolidinone; Pbf = 2,2,4,6,7-pentamethyldihydrobenzofuran-5-sulfonyl.

Analysis of Artificial Bak BH3

Circular Dichroism Studies

Figure 13:
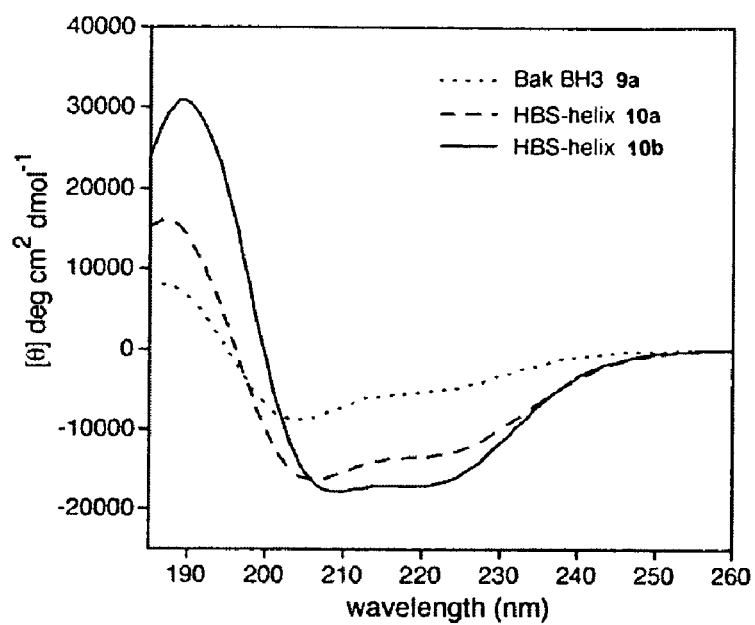
FIG. 13 is a graph illustrating the circular dichroism spectra of peptides 9a, 10a and 10b in 20% TFE/PBS.
Figure 14:
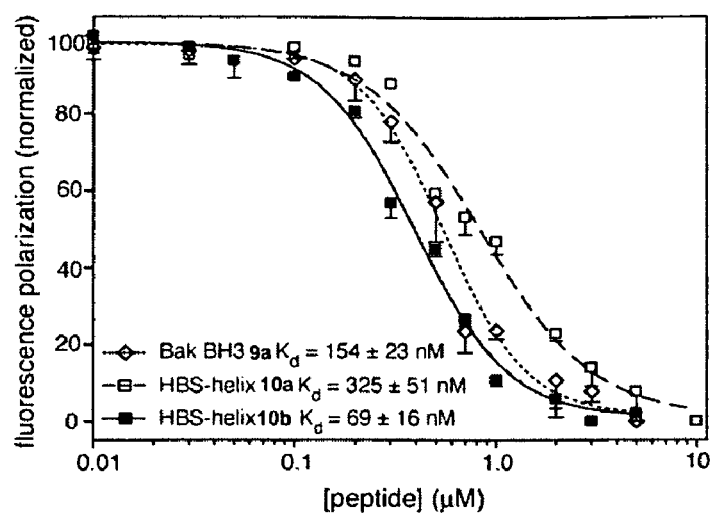
FIG. 14 is a graph illustrating the results of the fluorescence polarization assay used to test the competitive inhibition of the fl-Bak/Bcl-xL complex with Bak peptides 9a, 10a and 10b.

The α-helical conformation of constrained peptide 10a was determined by circular dichroism spectroscopy. CD studies on the constrained peptide 10a and the control peptide 9a were performed in 20% TFE in PBS buffer to obtain a quantitative measure of their helical content, as shown in FIG. 13. The CD spectra of the artificial α-helix 10a displays double minima at 206 and 222 nm, and maximum at 189 nm consistent with those observed for canonical α-helices (the CD spectra of canonical α-helices typically contain double minima at 208 and 222 nm and maxima at 193 nm). The HBS α-helix 10a is roughly 46% helical as measured by Yang's method (Chen et al., *Biochemistry*, 11:4120–4131 (1972), which is hereby incorporated by reference in its entirety). Consistent with previous studies (Petros et al., *Protein Sci.*, 9:2528–2534 (2000), which is hereby incorporated by reference in its entirety), the unconstrained Bak peptide was found to be significantly less helical (~26%). It is presumed that the GDD tripeptide residue in the middle of the Bak peptide sequence may be limiting the propagation of the helix and lowering the overall helical content of 10a, as glycine is known to be a potent "helix breaker" and the aspartic acid residue has been implicated as a helix stop signal (Chakrabartty et al., *Protein Sci.*, 3:843–852 (1994); O'Neil & DeGrado, *Science*, 250: 646–651 (1990); Nelson & Kallenbach, *Biochemistry*, 28:5256–5261 (1989), which are hereby incorporated by reference in their entirety). Fesik and coworkers have previously shown that the Gly-82 and Asp-83 residues cannot be substituted with alanine without sacrificing binding affinities for the protein. However, Asp-84 may be replaced without any deleterious effects (Sattler et al., *Science* 275: 983 (1997), which is hereby incorporated by reference in its entirety). To test the effect of replacing Asp-84 on the helicity of Bak peptide, HBS α-helix 10b in which Asp-84 is substituted with side chain acetylated-lysine ($Lys^{Ac}$) was prepared. This particular substitution was made because Bak BH3 peptide with a capped-lysine residue has been shown to bind Bcl-xL with high affinity (Zhang et al., *Anal. Biochem.* 307:70 (2002), which is hereby incorporated by reference in its entirety). It was found that this single substitution provided a significant boost in α-helicity, as demonstrated in FIG. 13. HBS helix 10b is roughly 65% helical—an increase in helicity of 140% over 10a. As expected, a similar increase in helicity for the unconstrained Bak BH3 was observed. Importantly, this set of experiments shows that the hydrogen-bond surrogate approach can successfully stabilize α-helical conformations in biologically relevant sequence. HBS helix 10b has the following structure:

fl-Bak/Bcl-xL complex with the Bak peptides 9a and 10a-b results in a decrease of fluorescence polarization. Regression analysis (Roehrl et al., *Biochemistry* 43:16056 (2004), which is hereby incorporated by reference in its entirety) provided a $K_d$ of 154±23 nM for the unconstrained Bak peptide 9a, which is within range of the previously reported values, as shown in FIG. 14. Under the same assay conditions, HBS helices 10a and 10b bound Bcl-xL with $K_d$'s of 325±51 nM and 69±16 nM, respectively, as shown in FIG. 14. These binding results illustrate the degree of difficulty involved in forcing an artificial helix into this pocket as the unconstrained Bak BH3 peptide 9a targets this protein with two-fold higher affinity than the constrained peptide 10a. However, these results validate the helix design principles of the present invention, as it is found that the internally constrained Bak α-helices of the present invention can bind to a deep hydrophobic cleft whereas the Bak α-helices prepared by the side chain bridging method showed no affinity for the same target. Moreover, it is shown that very high affinity binder (10b) for Bcl-xL can be developed by increasing the helicity of the constrained peptide through rational substitutions. HBS Bak α-helices designed to be more helical and to be a higher affinity binder than 10b are being prepared. It remains to be determined if these HBS α-helices show selectivity for Bcl-xL over other closely related members of the Bcl-2 family (and over other helix-binding proteins) (Chin & Schepartz, *Curr. Op. Chem. Bio.* 6:479 (2002); Gemperli et al., *J. Am. Chem. Soc.* 127:1596 (2005); Yin et al., *Agnew Chem. Int. Ed. Engl.* 44:2704 (2005), which are hereby incorporated by reference in their entirety).

Proteolytic cleavage is one of the principal reasons limiting the in vivo efficacy of peptides. Proteases are known to bind their substrates in linear or beta strand conformations (Tyndall et al., *Chem. Rev.* 105:973 (2005), which is hereby incorporated by reference in its entirety), and peptides locked into helical conformations have been shown to resist proteolytic degradation (Schafmeister & Verdine, *J. Am. Chem. Soc.* 122:5891 (2005); Shepherd et al., *J. Am. Chem. Soc.* 127:2974 (2005), which are hereby incorporated by reference in their entirety). The proteolytic stability of HBS Bak helices 10a–b as compared to Bak peptide 9a in the presence of trypsin, which was expected to cleave the peptide at the arginine residue (Arg-76) positioned two residues away from the macrocycle in helices 10a–b, was determined. This was done to find out how this residue, which lies outside the constraint yet is close enough to be in a highly helical conformation, responds to the protease. By comparing the initial velocities of cleavage by trypsin, it was found that the HBS α-helix 10a is proteolyzed roughly

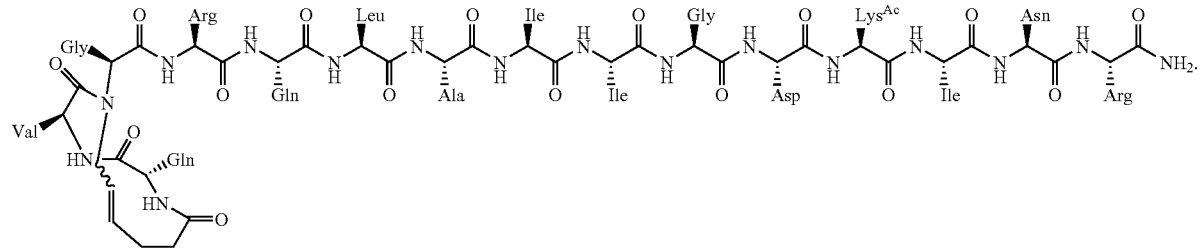

HBS α-helix 10b

Binding Affinity Assays

Figure 15:
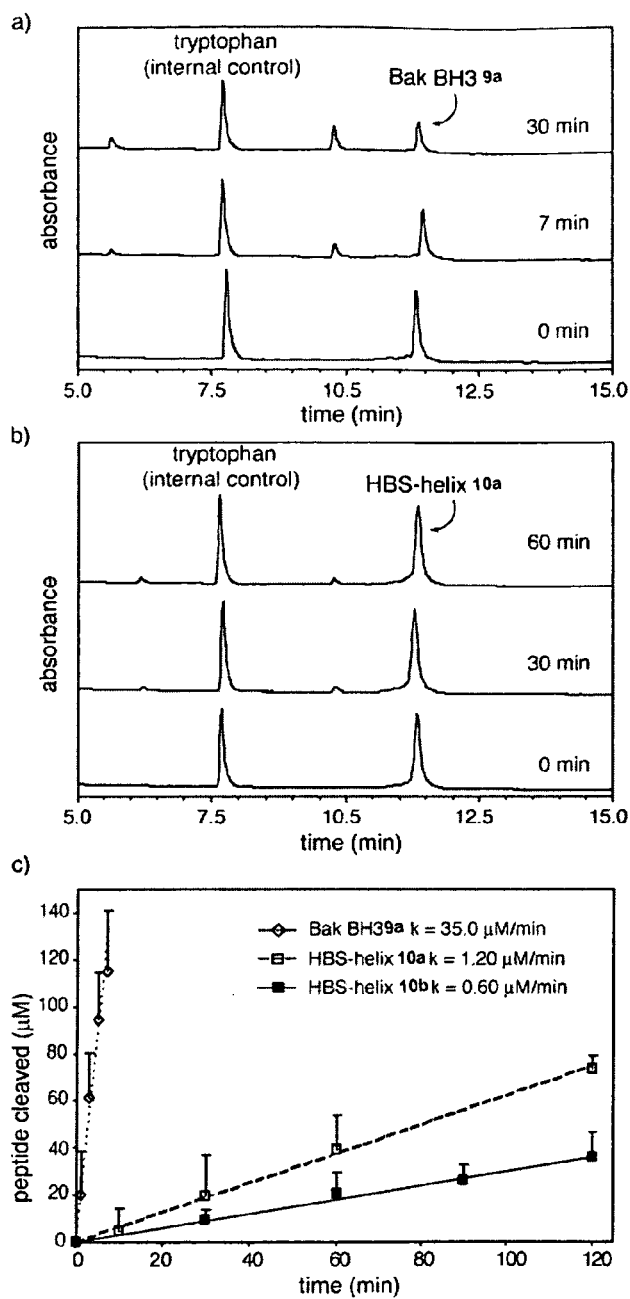
FIGS. 15A–C are graphs illustrating the results of degradation studies on Bak BH3 peptide 9a and internally constrained helices 10a and 10b. These results demonstrate the metabolic stability of artificial α-helices. HPLC assay shows rapid proteolysis of the unconstrained peptide 9a in the presence of trypsin (FIG. 15A), while the HBS α-helix 10a degrades at a 30-fold slower rate (FIG. 15B). Tryptophan (500 μM) was used as an internal control for the HPLC studies. Comparison of the initial velocities for the proteolysis of 9a, 10a, and 10b (FIG. 15C) shows that 10b is 60-fold more stable than 9a toward proteolytic degradation.

The binding affinities of the unconstrained Bak peptide 9a and artificial Bak α-helices 10a and 10b for Bcl-xL were assessed by a previously described fluorescence polarization assay using fluoresceine-labeled 16mer Bak peptide (fl-Bak). The binding affinity of the fl-Bak for Bcl-xL was determined to be 264±23 nM, which is consistent with the previously reported values. Competitive inhibition of the 30-fold slower than the unconstrained Bak peptide analog 9a, as shown in FIGS. 15A–C. As expected, an increase in the helicity of the constrained peptide results in a further decrease in the initial velocity of trypsin cleavage. Thus, the HBS helix 10b is roughly two-fold more stable than 10a and 60-fold more stable than 9a toward proteolysis by trypsin. The proteolytic stabilities observed for 10a–b are similar to that reported for a side-chain crosslinked α-helix (Schafmeister & Verdine, *J. Am. Chem. Soc.* 122:5891 (2005), which is hereby incorporated by reference in its entirety).

This Example demonstrates that artificial α-helices prepared by the replacement of a hydrogen bond between the i and i+4 residues at the N-terminus of a short peptide with a carbon-carbon bond can stabilize biologically relevant peptides in helical conformations. These HBS α-helices can bind their expected protein receptor with high affinity, and resist proteolytic degradation. Analogs of the Bak peptide are being developed to further increase the helicity and affinity of the HBS-derived Bak helices for the target protein.

Materials and Methods

Commercial-grade reagents and solvents were used without further purification except as indicated. $CH_2Cl_2$, THF, and DMF were dried prior to use by percolation through anhydrous $Al_2O_3$ as described by Grubbs and coworkers (Pangborn et al., *Organometallics*, 15:1518–1520 (1996), which is hereby incorporated by reference in its entirety). All reactions were stirred magnetically; moisture-sensitive reactions were performed under argon in flame-dried glassware. Thin-layer chromatography (TLC), usually using either ethyl acetate/hexane or ethyl acetate/$CH_2Cl_2$ as the solvent system, was used to monitor reactions. Visualization was accomplished by either ultraviolet light or by immersing the plate in a 1% aqueous solution of potassium permanganate and heating. Flash chromatography with silica gel was performed following the conditions described by Still and coworkers (Still et al., *J. Org. Chem.*, 43:2923–2925 (1978), which is hereby incorporated by reference in its entirety). Solvents were removed by rotary evaporation under reduced pressure; where appropriate, the residue was further dried using a vacuum pump. Reverse-phase HPLC experiments were conducted with 4.6×150 mm (analytical scale) or 21.4×150 mm (preparative scale) Waters $C_{18}$ reverse phase columns using a Beckman Coulter HPLC equipped with a System Gold 168 Diode array detector. The typical flow rates for analytical and preparative HPLC were 1 mL/min and 8 mL/min, respectively. In all cases, 0.1% aqueous trifluoroacetic acid and acetonitrile buffers were used. Proton NMR spectra were obtained on a Bruker AV-400 (400 MHz). Carbon NMR spectra were obtained on a Bruker (100.5 MHz) spectrometer. Proton chemical shifts are reported as d values relative to tetramethylsilane (0.00 ppm) or to the particular solvent used in the experiment ($CDCl_3$: 7.26 ppm). Carbon chemical shifts are reported as d values relative to the particular solvent used in the experiment ($CDCl_3$:77.0 ppm). Data is reported as follows: chemical shift, multiplicity (s=singlet, d=doublet, t=triplet, q=quartet, m=multiplet, dd=doublet of doublet, br=broad), coupling constant, and integration. Infrared (IR) spectra were obtained with a Thermo Nicolet Avatar 360 FTIR. High-resolution mass spectra (HRMS) were obtained on a LC/MSD TOF (Agilent Technologies). LCMS data was obtained on an Agilent 1100 series LC/MSD (XCT) electrospray trap.

Synthesis of Peptide 11

Fmoc-Val-N(allyl)-Gly-OH 11 was synthesized as shown in Scheme 10.

Scheme 10

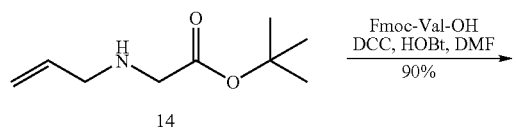

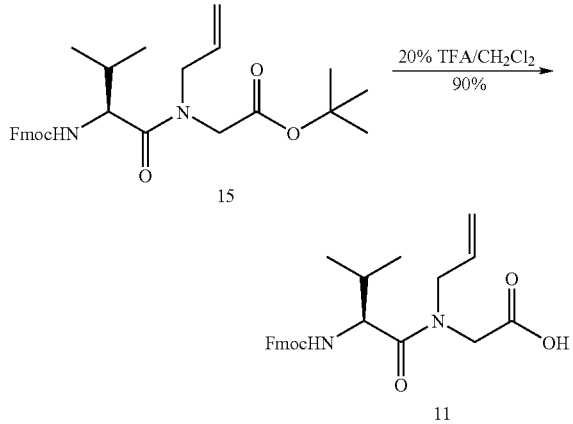

A solution of N,N-dicyclohexylcarbodiimide (DCC, 2.62 g, 12.7 mmol), 1-hydroxybenzotriazole (HOBt, 1.72 g, 12.7 mmol), FmocVal-OH (4.32 g, 12.7 mmol) and 40 mL of DMF was stirred for 15 minutes. N-Allyl-glycine-t-butyl ester 14 (1.67 g, 9.78 mmol) was then added to the flask and the reaction mixture was stirred at room temperature. After 13 hours, the reaction mixture was poured into 40 mL of water and extracted with ether (3×40 mL). The combined ether layers were washed with water (3×40 mL) and dried with anhydrous magnesium sulfate, filtered and concentrated by rotary evaporation. The residue was purified with flash chromatography (95:5, dichloromethane: ethyl acetate) to afford 4.33 grams of the dipeptide t-butyl ester 15 (90%) as a colorless oil ($^1$H NMR (400 MHz, $CDCl_3$) δ 7.75 (d, J=7.5 Hz, 2H), 7.60 (d, J=7.4 Hz, 2H), 7.39 (t, J=7.4 Hz, 2H), 7.30 (tt, J=7.4 Hz, 1.0 Hz, 2H), 5.88–5.70 (m, 1H), 5.60 (d, J=9.2 Hz, 1H), 5.26–5.13 (m, 2H), 4.56 (dd, J=11.0, 6.2 Hz, 1H), 4.42–4.36 (m, 1H), 4.35–4.31 (m, 1H), 4.29–4.18 (m, 2H), 4.14–4.08 (m, 1H), 4.04–3.97 (m, 1H), 3.67 (d, J=17.0 Hz, 1H), 2.12–1.99 (m, 1H), 1.45 (s, 9H), 1.05 (d, J=6.7 Hz, 3H), 0.95 (d, J=6.9 Hz, 3H); $^{13}$C NMR (100 MHz) δ 172.34, 167.98, 156.28, 143.92, 141.26, 132.40, 127.65, 127.05, 125.18, 119.93, 118.45, 81.81, 66.98, 55.50, 51.35, 47.88, 47.18, 31.72, 28.02, 19.68, 17.32; IR (film) 2974, 1734, 1717, 1652, 1647 cm$^{-1}$; HRMS m/z for $C_{29}H_{37}N_2O_5$ [M+H]$^+$ calcd 493.2702, found 493.2699).

A solution of dipeptide t-butyl ester 15 (2.37 g, 4.81 mmol), 80 mL of dichloromethane, 20 mL of trifluoroacetic acid (TFA) was stirred for 4 hours, and then concentrated under vacuum. The residue was redissolved in 80 mL of dichloromethane and washed with water (3×40 mL). The organic layer was dried over anhydrous magnesium sulfate, filtered, and concentrated. The residue was purified by flash chromatography (1:1, hexane:ethyl acetate) to afford 1.89 grams of peptide 11 (90%) as a white foam ($^1$H NMR (400 MHz, $CDCl_3$) δ 7.68 (d, J=7.4 Hz, 2H), 7.52 (d, J=7.5 Hz, 2H), 7.32 (t, J=7.4 Hz, 2H), 7.24 (t, J=7.4 Hz, 2H), 5.80–5.71 (m, 1H), 5.60 (d, J=8.8 Hz, 1H), 5.21–5.08 (m, 2H), 4.48 (dd, J=9.0 Hz, 6.5 Hz, 1H), 4.35–4.22 (m, 4H), 4.16–4.09 (m, 2H), 4.06–3.97 (m, 2H), 3.79 (d, J=17.3 Hz, 1H), 2.02–1.91 (m, 1H), 0.93 (d, J=6.7 Hz, 3H), 0.87 (d, J=6.4 Hz, 3H); $^{13}$C NMR (100 MHz) δ 173.30, 172.57, 156.46, 143.80, 141.27, 132.00, 127.72, 127.06, 125.17, 119.96, 119.01, 67.11, 55.66, 51.64, 49.47, 47.14, 31.59, 19.48, 17.36; IR (film) 1722, 1711, 1657, 1642 cm$^{-1}$; HRMS m/z for $C_{25}H_{29}N_2O_5$ [M+H]$^+$ calcd 437.2076, found 437.2067).

Synthesis of Bak $BH3_{72-87}$ Peptide 9a and 9b

Bak $BH3_{72-87}$ peptide 9a and 9b have the following structures:

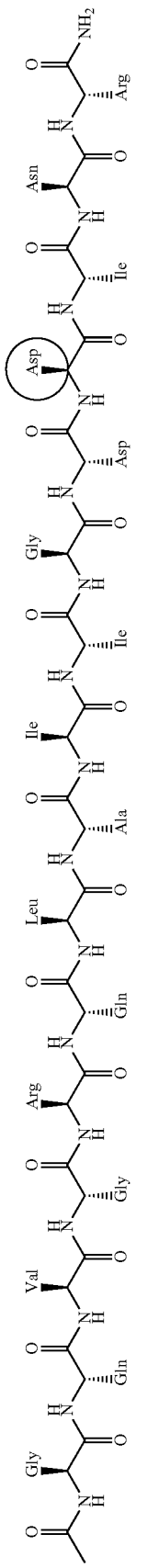
BakBH3₇₂₋₈₇ peptide 9a
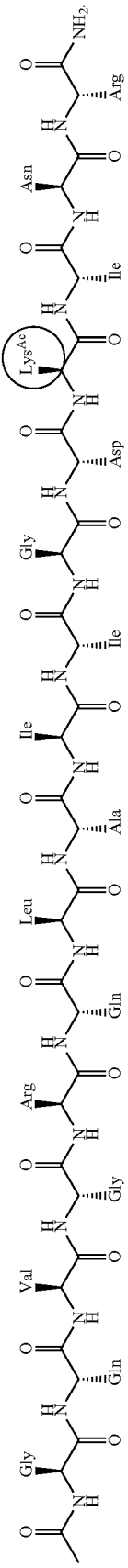
BakBH3₇₂₋₈₇ peptide 9b

They were synthesized as shown in Scheme 11.

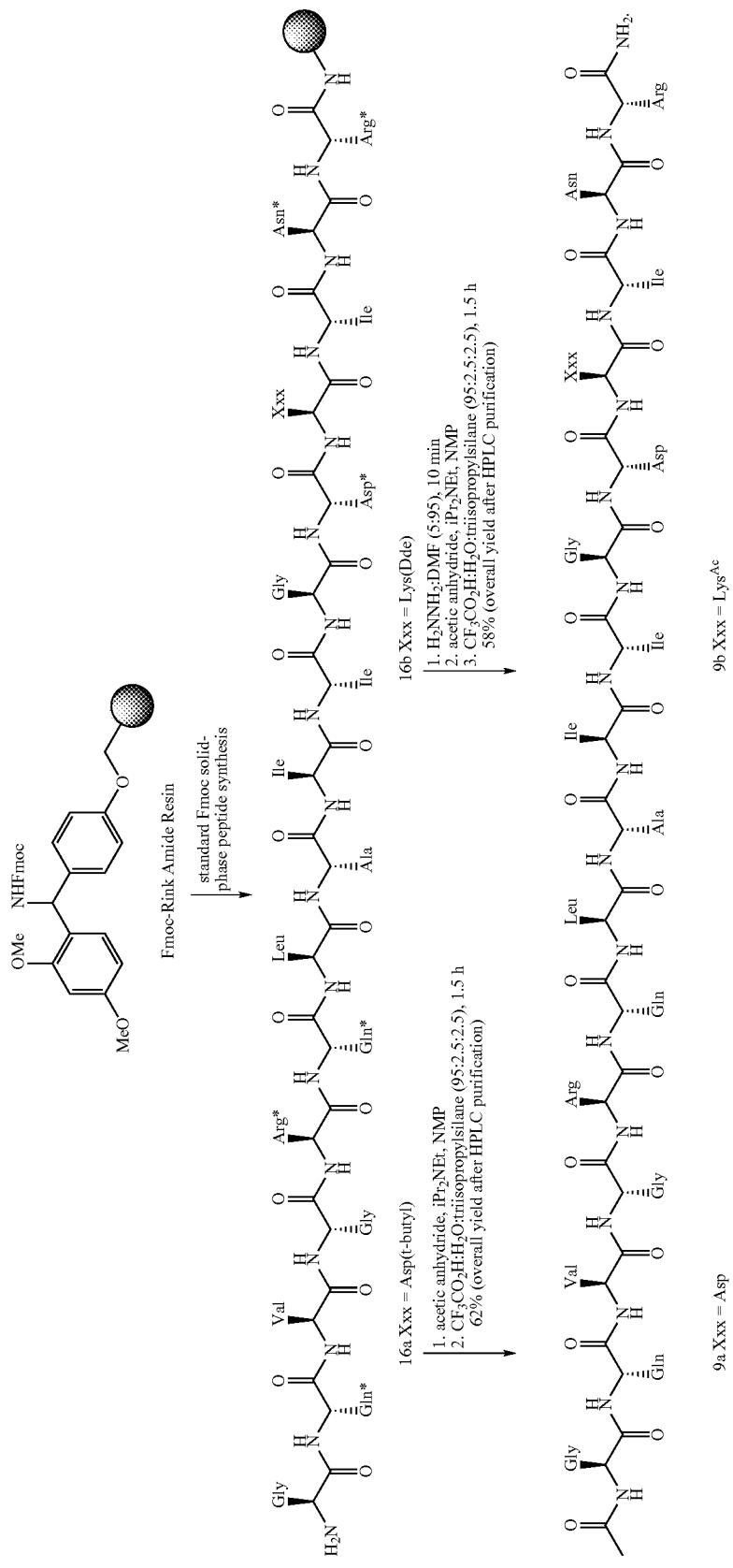

Scheme 11

16a Xxx = Asp(t-butyl)
1. acetic anhydride, iPr₂NEt, NMP
2. CF₃CO₂H:H₂O:triisopropylsilane (95:2.5:2.5), 1.5 h
62% (overall yield after HPLC purification)

16b Xxx = Lys(Dde)
1. H₂NNH₂:DMF (5:95), 10 min
2. acetic anhydride, iPr₂NEt, NMP
3. CF₃CO₂H:H₂O:triisopropylsilane (95:2.5:2.5), 1.5 h
58% (overall yield after HPLC purification)

9a Xxx = Asp

9b Xxx = Lys^Ac

Arg*: Pbf protected Arg; Gln*: trityl protected Gln; Asn*: t-butyl protected Asn; Asp*: t-butyl protected Asp; Dde: N-α-1-(4,4-dimethyl-2,6-dioxocyclohex-1-yldene)ethyl group; NMP = N-methylpyrrolidinone; Pbf = 2,2,4,6,7-pentamethyldihydrobenzofuran-5-sulfonyl.

The Bak BH3 peptide 9a was synthesized by conventional Fmoc solid phase chemistry on Rink amide resin (NovaBiochem). The Fmoc group was removed from Rink amide resin (125 mg, 0.08 mmol) by treatment with 1.0 mL of 20% peperidine in NMP (2×20 min). The resin was then washed with DMF (2×), dichloromethane (2×) and MeOH (3×). The free amine was treated with preactivated Fmoc-Asn (Trt)-OBt, which was prepared from Fmoc-Arg (Pfp)-OH (166 mg, 0.256 mmol), HBTU (88 mg, 0.230 mmol) and 1.2 mL of 5% DIPEA/NMP. After 45 minutes of shaking, the resin was washed with DMF (2×), dichloromethane (2×) and MeOH (3×). This procedure was repeated for the introduction of the remaining amino acids to afford resin-bound peptide 16a, which was acetylated with acetic anhydride (0.4 mL) in DMF (3.2 mL). The resin was treated with the cleavage cocktail ($CF_3CO_2H$:$H_2O$:triisopropylsilane, 95:2.5:2.5) for 1.5 hours and then concentrated by rotary evaporation. The residue was purified by reversed-phase HPLC to yield 1 (88 mg, 62%) as a white solid after lyophilization (ESIMS m/z for $C_{74}H_{128}N_{26}O_{24}$ $[M+H]^+$ calcd 1766.0, found 1766.8).

The mutated Bak BH3 peptide 9b was synthesized on Rink amide resin similar to 9a with appropriate substitution with Fmoc-Lys(Dde)-OH. The N-a-1-(4,4-dimethyl-2,6-dioxocyclohex-1-yldene)ethyl (Dde) protecting group in lysine residue was removed by treatment with 5% hydrazine DMF solution, and the lysine side chain was acetylated with acetic anhydride. Peptide 9b was then cleaved from resin by treatment with the cleavage cocktail (TFA:$H_2O$:triisopropylsilane, 95:2.5:2.5) in 58% yield (ESIMS m/z for $C_{78}H_{138}N_{27}O_{23}$ $[M+H]^+$ calcd 1821.0, found 1821.7).

Synthesis of α-Helices 10a and 10b

The HBS constrained α-helices 10a and 10b were synthesized on the solid phase as shown in Scheme 12.

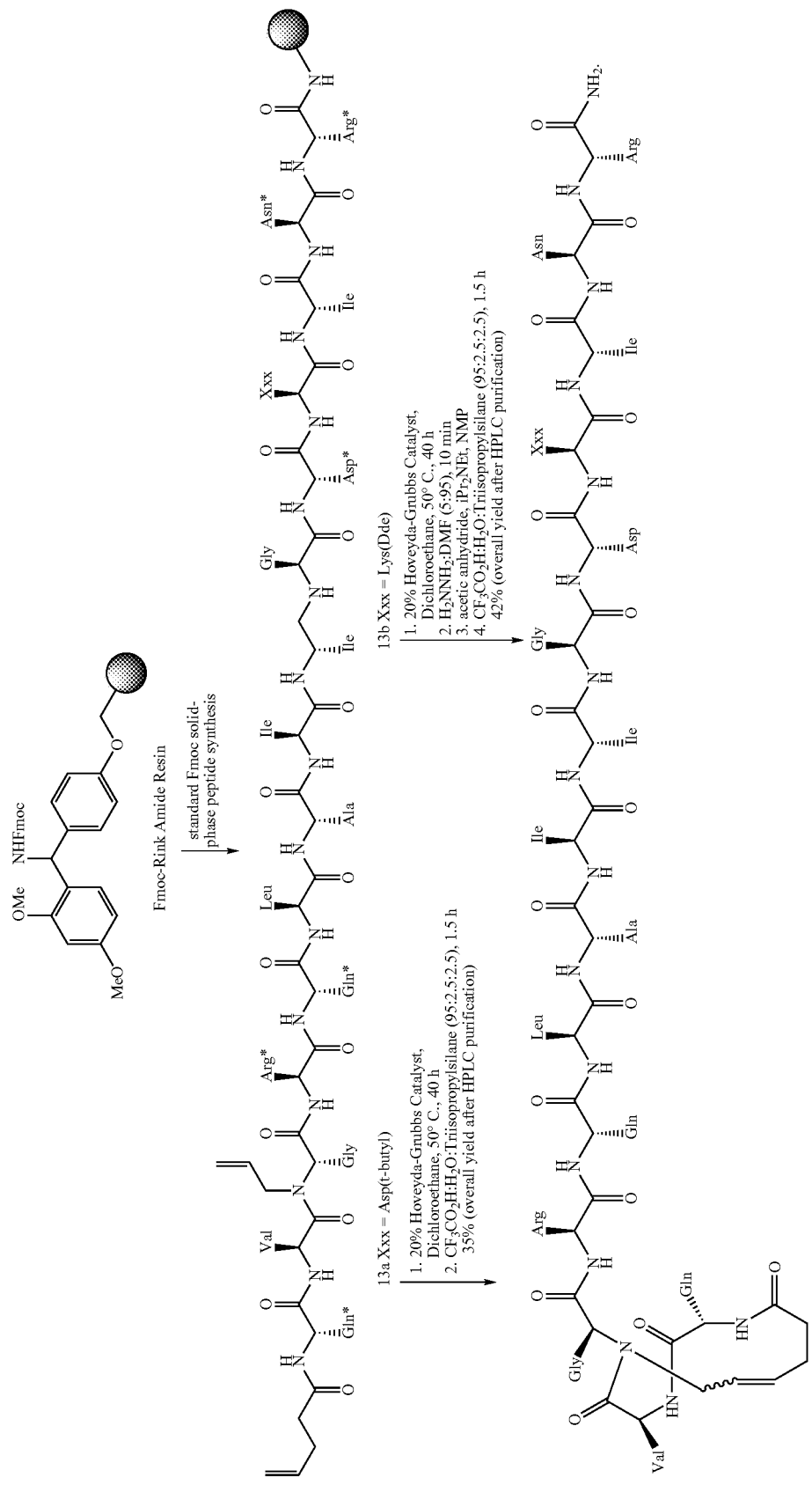

Bis-olefin resin bound peptide 13a was synthesized by conventional Fmoc solid phase chemistry (as described earlier for the synthesis of peptide 9a) on Rink amide resin (250 mg, 0.16 mmol) with appropriate substitutions with dipeptide 11 and pentenoic acid. The resin bound peptide 13a was dried under vacuum overnight and then swelled in 1.5 mL of anhydrous 1,2-dichloroethane (DCE) in a dried flask under an argon atmosphere for 30 minutes. The Hoveyda-Grubbs catalyst (20 mg, 0.032 mmol) in 1.5 mL of DCE was added to the flask and the mixture was stirred at 50° C. After 40 hours, the resin was washed with dichloromethane (3×), 10% 1,3-bis (diphenylphosphino) propane in dichloromethane solution (1×), dichloromethane (3×) and methanol (3×). The washed peptide was cleaved from the resin by treatment with 30 mL of the cleavage cocktail ($CF_3CO_2H:H_2O$:triisopropylsilane, 95:2.5:2.5) for 1.5 hours. The reaction mixture was concentrated and purified by reversed-phase HPLC to yield peptide 10a (99 mg, 35% overall yield) (ESIMS for $C_{76}H_{129}N_{25}O_{23}$ $[M+H]^+$, calcd 1761.0, found 1762.0).

The HBS α-helix 10b was synthesized from Rink amide resin similar to HBS α-helix 10a with appropriate substitution with Fmoc-Lys(Dde)-OH. The Dde protecting group in lysine residue was removed by treatment with 5% hydrazine DMF solution, and the lysine side chain was consequently acetylated by acetic anhydride. Peptide 10b was then cleaved from the resin by treatment with the cleavage cocktail (TFA:$H_2O$:triisopropylsilane, 95:2.5:2.5) in 42% yield (ESIMS m/z for $C_{80}H_{139}N_{26}O_{22}$ $[M+H]^+$ calcd 1816.0, found 1816.5).

Synthesis of Bak $BH3_{72-87}$ Peptide fl-Bak Peptide 17

The fluoresceine-labeled Bak (fl-Bak) peptide 17 was synthesized from the Wang resin-bound peptide 18 by treatment with 5-carboxylfluorescein succinimidyl ester (5-FAMSE, Molecular Probes), followed by cleavage (TFA:$H_2O$:triisopropylsilane, 95:2.5:2.5) from the Wang resin as a carboxylic acid in 67% yield (ESIMS m/z for $C_{93}H_{136}N_{25}O_{30}$ $[M+H]^+$ calcd 2084.2, found 2084.0), as shown in Scheme 13.

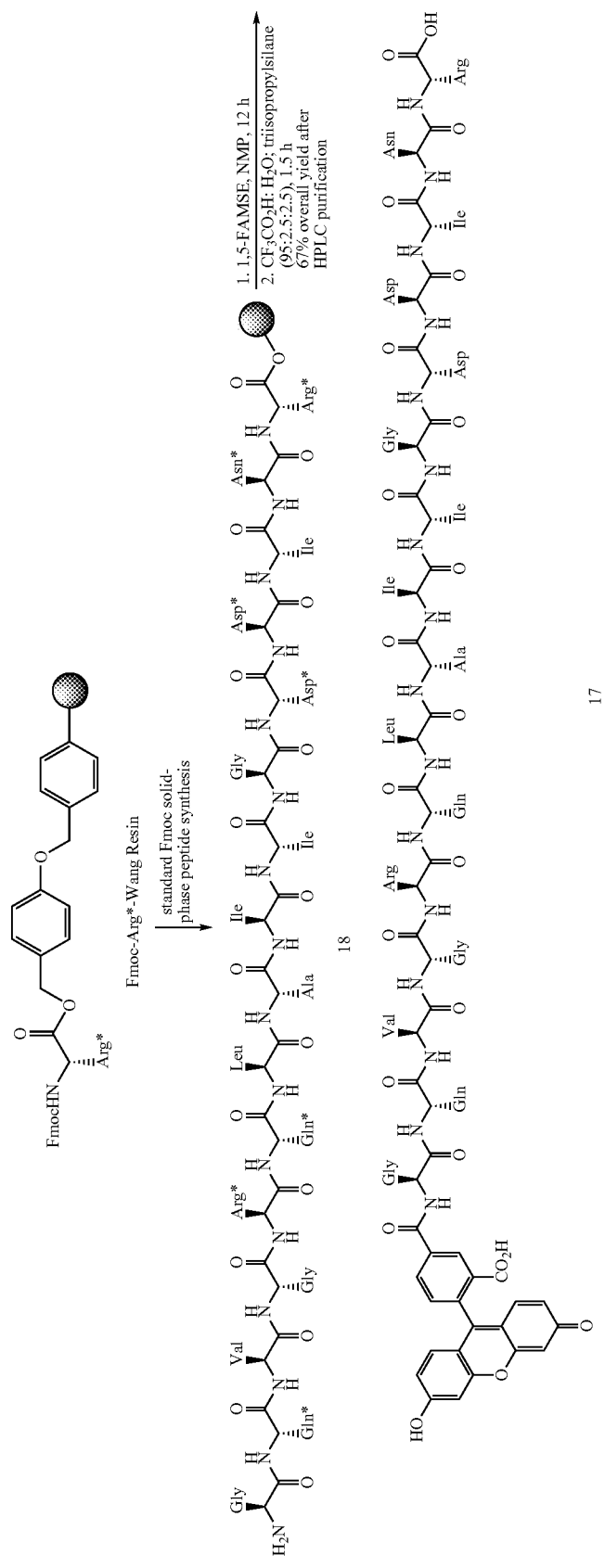

Circular Dichroism Spectra

CD spectra were recorded on AVIV 202SF CD spectrometer equipped with a temperature controller using 1 mm length cells and a scan speed of 5 nm/min at 25° C. The spectra were averaged over 10 scans with the baseline subtracted from analogous conditions as that for the samples. The samples were prepared in 10 mM phosphate buffered saline containing 20% trifluoroethanol, with the final peptide concentration of 50 μM. The helix content of each peptide was determined from the mean residue CD at 222 nm, $[\theta]_{222}$ (deg cm$^2$ dmol$^{-1}$) corrected for the number of amide bonds (Chen et al., *Biochemistry* 111:4120431 (1972), which is hereby incorporated by reference in its entirety). Percent helicity was calculated from ratio $[\theta]_{222}/[\theta]_{max}$, where $[\theta]_{max}=-39500\times[1-(2.57/n)]$. The $[\theta]_{max}$ for HBS α-helices is calculated to be −33155 for n=16 (number of amide bonds in the peptide).

Bcl-xL Binding Assay

The relative affinity of each peptide for His$_6$-tagged human Bcl-xL (obtained from ProteinX Lab, San Diego, Calif.) was determined using fluorescence polarization-based competitive binding assay with fluoresceine-labeled Bak peptide (fl-Bak) 17. The anisotropy experiments were performed with a DTX 880 Multimode Detector (Beckman) at 4° C., with excitation and emission wavelengths of 485 and 525 nm, respectively. All the titration samples were prepared in a 96 well plate in the presence of 4% DMSO and 0.1% pluronic acid. The binding affinity ($K_D$ or IC$_{50}$) values reported for each peptide are the averages of 3~5 individual measurements, and were determined by fitting the experimental data to a sigmoidal dose-response nonlinear regression model on GraphPad Prism 4.0. The concentration of the Bcl-xL protein stock solution used in these experiments was determined with the BCA protein assay kit (Pierce).

Figure 16:
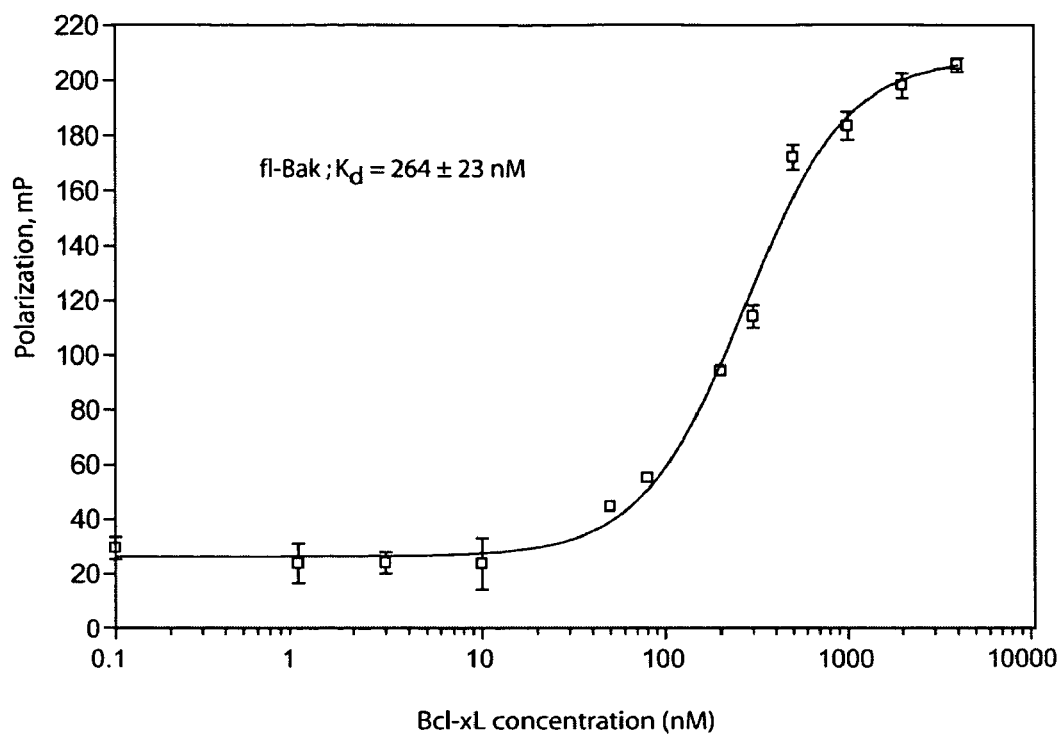
FIG. 16 is a graph showing the saturation binding curve of fl-Bak 17 to Bcl-xL.

Prior to the competition experiments, the affinity of fl-Bak 17 for Bcl-xL was determined by monitoring polarization of the fluorescent probe upon addition of Bcl-xL. Addition of an increasing concentration (0 nM to 4 μM) of the Bcl-xL protein to a 15 nM solution of fl-Bak 17 in PBS buffer at 4° C. afforded a saturation binding curve, shown in FIG. 16 (Zhang, *Anal. Biochem.* 307:70–75 (2002), which is hereby incorporated by reference in its entirety). The IC$_{50}$ value gotten from this binding curve was fit into the following equation (a) to calculate the dissociation constant ($K_{D1}$) for the fl-Bak 17 and Bcl-xL complex (Roehrl et al., *Biochemistry*, 43:16056–16066 (2004); Roehrl et al., *Biochemistry* 43:16067–16075 (2004), which are hereby incorporated by reference in their entirety).

$$a: K_{D1}=(R_T*(1-F_{BS})+L_{ST}*F_{SB}^2)/F_{BS}-L_{ST}$$

$K_{D1}$: $K_D$ of fluoresceine probe 17
$R_T$: Total concentration of Bcl-xL;
$L_{ST}$: Total concentration of fl-Bak;
$F_{SB}$: Fraction of bound fl-Bak.

This $K_{D1}$ value was used to calculate the optimum concentrations of the probe (15 nM fl-Bak) and the protein (500 nM Bcl-xL) needed for the competition binding anisotropy assays. These concentrations were chosen to develop a highly sensitive fluorescence polarization assay. The sensitivity and usability of a polarization assay largely depends on two important considerations: (a) concentration of the complex should be chosen so that the polarized probe affords an observable signal (beyond experimental error) over background, and (b) the concentration of the protein should be lower than that needed for saturation of the probe because excess protein concentrations would lead to inaccurately high IC$_{50}$ values. Based on the $K_{D1}$ of fl-Bak and Bcl-xL complex, at 500 nM Bcl-xL and 15 nM fl-Bak, 82% of the fluorescent probe should be bound to the protein while a measurable change in polarization signal (~90–100 mP) is expected upon inhibition of the fl-Bak/Bcl-xL complex by the antagonist (9a, 9b, 10a or 10b).

Competition Polarization Assay

Appropriate concentrations (10 nM to 10 μM) of the antagonists (9a, 9b, 10a or 10b) were added to a solution of 500 nM Bcl-xL and 15 nM fl-Bak 3, and the resulting mixtures were incubated at 4° C. After 1 hour, the value of the dissociated fluorescent probe 17 was determined by the fluorescence polarizer. The dissociated constant (IC$_{50}$) was fit into the following equation (b) to calculate the $K_{D2}$ value of the antagonist (9a, 9b, 10a or 10b) (Roehrl et al., *Biochemistry*, 43:16056–16066 (2004); Roehrl et al., *Biochemistry* 43:16067–16075 (2004), which are hereby incorporated by reference in their entirety).

$$b: K_{D2}=K_{D1}*F_{SB}*\left(\frac{L_T}{L_{ST}*F_{SB}^2-(K_{D1}+L_{ST}+R_T)*F_{SB}+R_T}-\frac{1}{1-F_{SB}}\right)$$

$K_{D1}$: $K_D$ of floresceine probe 17
$K_{D2}$: $K_D$ of antagonist peptide (9a, 9b, 10a or 10b);
$R_T$: Total concentration of Bcl-xL;
$L_{ST}$: Total concentration of fl-Bak;
$F_{SB}$: Fraction of bound fl-Bak.
$L_T$: Total concentration of antagonist (9a, 9b, 10a or 10b)

Trypsin Cleavage Assay

A solution containing 500 μM of tryptophan, 1 ng/μL of trypsin and 0.5 mM of peptide (9a, 9b, 10a or 10b) in phosphate buffer saline (PBS) was incubated at 4° C. At different time intervals, 100 μL of the above solution was taken out, quenched with 100 μL of 2% TFA aqueous solution, and then injected into reversed-phase HPLC to analyze the change in the area of the peptide peak compared to the area of internal control (tryptophan).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of preparing a compound of Formula II:

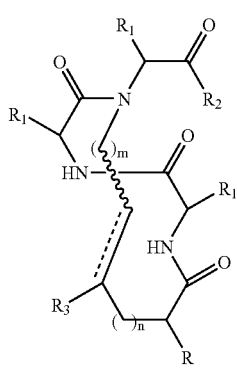

II wherein
R is hydrogen, an amino acid side chain, an alkyl group, or an aryl group;
$R_1$ is an amino acid side chain, an alkyl group, or an aryl group;
$R_2$ is an amino acid, peptide, OR, $CH_2NH_2$, an alkyl group, an aryl group, or a group of formula:

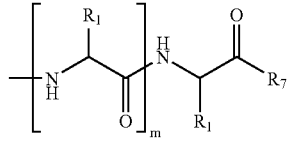

wherein $R_7$ is an amino acid, peptide, OR, $CH_2NH_2$, an alkyl group, or an aryl group; $R_3$ is an amino acid, peptide, OR, $CH_9Mi_2$, an alkyl group, an aryl group, hydrogen, or a group of formula

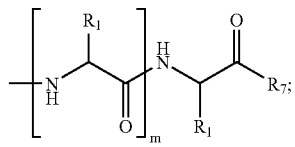

----- is a single or double carbon-carbon bond; ⁓ is a single bond and is cis or trans when ----- is a double bond; n is 1 or 2; and m is any number, said method comprising:

providing a compound of Formula I:

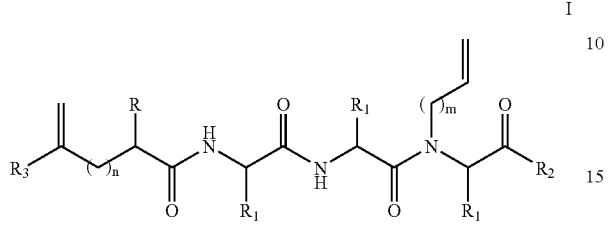

I and reacting said compound of Formula I under conditions effective to produce a compound of Formula II; wherein said reacting comprises a ring-closing metathesis reaction.

2. The method according to claim 1, wherein said metathesis reaction is performed with a metathesis catalyst of the formula:

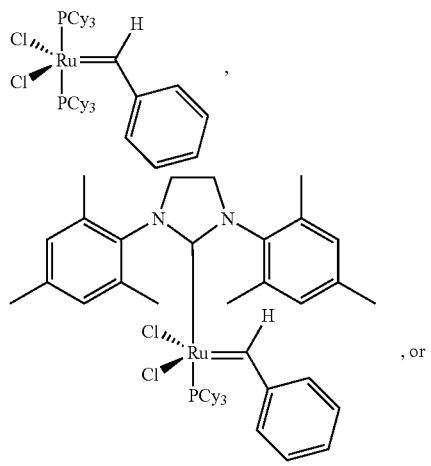

, or

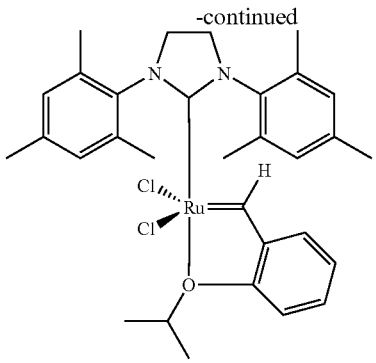

3. The method according to claim 2, wherein said metathesis catalyst is of the formula:

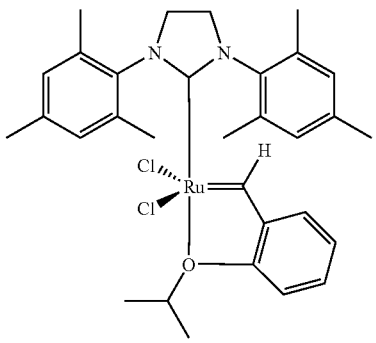

4. The method according to claim 1, wherein said metathesis reaction is performed at a temperature between about 25° C. and 110° C.

5. The method according to claim 1, wherein said metathesis reaction is performed with an organic solvent.

6. The method according to claim 5, wherein said organic solvent is selected from the group consisting of dichloromethane, dichloroethane, trichloroethane, and toluene.

7. The method according to claim 6, wherein said organic solvent comprises dichloroethane.

8. The method according to claim 1, wherein said reacting is carried out on a solid support.

* * * * *